US012797482B2

(12) United States Patent
Acharya et al.

(10) Patent No.: US 12,797,482 B2
(45) Date of Patent: Nov. 17, 2026

(54) METABOLITE-BASED POLYMERS, MICROPARTICLES, AND NANOPARTICLES FOR IMMUNOTHERAPY AND METHODS OF TREATING A DISEASE OR DISORDER

(71) Applicant: Arizona Board of Regents on behalf of Arizona State University, Scottsdale, AZ (US)

(72) Inventors: Abhinav Acharya, Tempe, AZ (US); Sahil H. Inamdar, Tempe, AZ (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 1132 days.

(21) Appl. No.: 17/758,482

(22) PCT Filed: Jan. 8, 2021

(86) PCT No.: PCT/US2021/012691
§ 371 (c)(1),
(2) Date: Jul. 7, 2022

(87) PCT Pub. No.: WO2021/142254
PCT Pub. Date: Jul. 15, 2021

(65) Prior Publication Data

US 2023/0058160 A1 Feb. 23, 2023

Related U.S. Application Data

(60) Provisional application No. 62/958,465, filed on Jan. 8, 2020.

(51) Int. Cl.
*A61K 47/69* (2017.01)
*A61K 39/00* (2006.01)
(Continued)

(52) U.S. Cl.
CPC .......... *A61K 47/6929* (2017.08); *A61K 39/39* (2013.01); *A61K 45/06* (2013.01);
(Continued)

(58) Field of Classification Search
None
See application file for complete search history.

(56) References Cited

U.S. PATENT DOCUMENTS

| | | | | |
|---|---|---|---|---|
| 2013/0287729 A1* | 10/2013 | Keselowsky | ...... | A61K 47/6937 424/85.4 |
| 2017/0066901 A1 | 3/2017 | Yang | | |

(Continued)

FOREIGN PATENT DOCUMENTS

| | | |
|---|---|---|
| WO | 2020232357 | 11/2020 |
| WO | 2021050812 | 3/2021 |

OTHER PUBLICATIONS

Brunner et al., Colloids and Surfaces B: Biointerfaces, 84, 408-507 (Year: 2011).*

(Continued)

*Primary Examiner* — Clinton A Brooks
*Assistant Examiner* — Jason M. Nolan
(74) *Attorney, Agent, or Firm* — Riverside Law LLP

(57) ABSTRACT

The present invention provides polymers, microparticles, nanoparticles, and compositions thereof for inducing an immune response and preventing or treating a metabolic inhibition in a subject. The present invention additionally provides kits that find use in the practice of the methods of the invention.

14 Claims, 40 Drawing Sheets

Specification includes a Sequence Listing.

(51) Int. Cl.
*A61K 39/39* (2006.01)
*A61K 45/06* (2006.01)
*A61P 35/00* (2006.01)

(52) U.S. Cl.
CPC ...... *A61P 35/00* (2018.01); *A61K 2039/5154* (2013.01); *A61K 2039/55555* (2013.01); *A61K 2039/55561* (2013.01)

(56) References Cited

U.S. PATENT DOCUMENTS

| | | | | |
|---|---|---|---|---|
| 2018/0318349 A1 | 11/2018 | Thompson | | |
| 2020/0016264 A1* | 1/2020 | Hoerr | ..................... | A61K 39/39 |
| 2020/0054741 A1* | 2/2020 | Lynn | ..................... | A61K 39/12 |

OTHER PUBLICATIONS

Zhang et al., J. Mater. Chem. B, 5, 4470-4477 (Year: 2017).*
A Phase I Trial of AZD3965 in Patients With Advanced Cancer—ClinicalTrials.gov Identifier: NCT01791595, 15 pages.
Acharya et al. 2017, "Localized Multi-Component Delivery Platform Generates Local and Systemic Anti-Tumor Immunity", Adv. Funct. Mater., 27:1604366.
Ashrafian et al., 2007, "Perhexiline", Cardiovascular Drug Reviews, 25:76-97.
Balint et al., 2015, "Extended evaluation of a phase 1/2 trial on dosing, safety, immunogenicity, and overall survival after immunizations with an advanced-generation Ad5 [E1-, E2b-]-CEA(6D) vaccine in late-stage colorectal cancer", Cancer Immunol. Immunother., 64:977-987.
Bendell et al., 2012, "Phase I, dose-escalation study of BKM120, an oral pan-Class I PI3K inhibitor, in patients with advanced solid tumors", J. Clin. Oncol., 30:282-290.
Bertrand et al., 2015, "Blocking tumor necrosis factor α enhances CD8 T-cell-dependent immunity in experimental melanoma", Cancer Res., 75:2619-2628.
Boon et al., 2006, "Human T cell responses against melanoma", Annu. Rev. Immunol., 24:175-208.
Buck et al., 2016 "Mitochondrial Dynamics Controls T Cell Fate through Metabolic Programming", Cell, 166:63-76.
Camarda et al., 2016, "Inhibition of fatty acid oxidation as a therapy for MYC-overexpressing triple-negative breast cancer" Nat. Med., 22:427-432.
Chang et al., 2015, "Metabolic Competition in the Tumor Microenvironment is a Driver of Cancer Progression", Cell, 162:1229-1241.
Clem et al., 2013, "Targeting 6-Phosphofructo-2-Kinase (PFKFB3) as a Therapeutic Strategy against Cancer", Mol. Cancer Ther., 12:1461-1470.
Denko et al., 2014, "Hypoxic regulation of metabolism offers new opportunities for anticancer therapy", Expert Review of Anticancer Therapy, 14:979-981.
Dichloroacetate (DCA) in Patients With Previously Treated Metastatic Breast or Non-Small Cell Lung Cancer (NSCL)—ClinicalTrials.gov Identifier: NCT01029925, 8 pages.
Effect of Metformin on Breast Cancer Metabolism—ClinicalTrials.gov Identifier: NCT01266486, 7 pages.
Eriksson et al., 2016, "Gemcitabine reduces MDSCs, tregs and TGFβ-1 while restoring the teff/treg ratio in patients with pancreatic cancer", J. Transl. Med., 14:282.
Gardner et al., 2013, "Biomaterials-based modulation of the immune system" BioMed Research International, 2013:732182.
Gustafsson et al., 2018, "Targeting PFKFB3 radiosensitizes cancer cells and suppresses homologous recombination", Nat. Commun., 9:3872.
Hernadez-Davies et al., 2015, "Vemurafenib resistance reprograms melanoma cells towards glutamine dependence", J. Transl. Med., 13:210.
Hossain et al., 2015, "Inhibition of Fatty Acid Oxidation Modulates Immunosuppressive Functions of Myeloid-Derived Suppressor Cells and Enhances Cancer Therapies", Cancer Immunol. Res., 3:1236-1247.
Jacobs et al., 2012, "Regulatory T cells in melanoma: The final hurdle towards effective immunotherapy?", The Lancet Oncology, 13:e32-42.
Klein Geltink et al., 2017, "Mitochondrial Priming by CD28", Cell, 171:385-397.e11.
Kouidhi et al., 2018, "Targeting tumor metabolism: a new challenge to improve immunotherapy", Frontiers in immunology, 9:336488.
Koyama et al. 2008, "Reciprocal CD4+ T-cell balance of effector CD62Llow CD4+ and CD62LhighCD25+ CD4+ regulatory T cells in small cell lung cancer reflects disease stage", Clin. Cancer Res., 14:6770-6779.
Krejcik et al., 2016, "Daratumumab depletes CD38+immune regulatory cells, promotes T-cell expansion, and skews T-cell repertoire in multiple myeloma", Blood, 128:384-394.
Liu et al., 2012, "Sticky nanoparticles: a platform for siRNA delivery by a bis (zinc (II) dipicolylamine)-functionalized, self-assembled nanoconjugate", Angewandte Chemie (International ed. in English), 51:445-449.
Liu et al., 2018, "T cell mediated immunity after combination therapy with intralesional PV-10 and blockade of the PD-1/PD-L1 pathway in a murine melanoma model", PLoS One, 13:e0196033.
Long et al., 2017, "Ibrutinib treatment improves T cell number and function in CLL patients", J. Clin. Invest., 127:3052-3064.
Lu et al., 2017, "The molecular basis of targeting PFKFB3 as a therapeutic strategy against cancer", Oncotarget, 8:62793-62802.
McClements et al., 2018, "Encapsulation, protection, and delivery of bioactive proteins and peptides using nanoparticle and microparticle systems: A review", Advances in colloid and interface science, 253:1-22.
Meeth et al., 2016, "The YUMM lines: a series of congenic mouse melanoma cell lines with defined genetic alterations", Pigment Cell Melanoma Res., 29:590-597.
O'Sullivan et al., 2014 "Memory CD8+ T Cells Use Cell-Intrinsic Lipolysis to Support the Metabolic Programming Necessary for Development", Immunity, 41:75-88.
Palao-Suay et al., 2017, "Photothermal and photodynamic activity of polymeric nanoparticles based 2 on alpha-tocopheryl succinate-RAFT block copolymers conjugated to IR-780", Acta Biomater. 57:70-84.
Perret et al., 2013, "Adjuvants that improve the ratio of antigen-specific effector to regulatory T cells enhance tumor immunity", Cancer Res., 73:6597-6608.
Rothschild et al., 2015, "Subverting subversion: A review on the breast cancer microenvironment and therapeutic opportunities supplementary issue: Targeted therapies in breast cancer treatment", Breast Cancer Basic Clin. Res., 9:7-15.
Sakaguchi et al., 2013, "The plasticity and stability of regulatory T cells", Nature Reviews Immunology, 13:461-467.
Selby et al., 2013, "Anti-CTLA-4 Antibodies of IgG2a Isotype Enhance Antitumor Activity through Reduction of Intratumoral Regulatory T Cells", Cancer Immunol. Res., 1:32-42.
Siska et al., 2017, "Mitochondrial dysregulation and glycolytic insufficiency functionally impair CD8 T cells infiltrating human renal cell carcinoma", JCI Insight 2:e93411.
Smith et al., 2016, "Targeting metabolic reprogramming as a potential therapeutic strategy in melanoma", Pharmacological Research, 107:42-47.
Spranger et al., 2013, "Up-regulation of PD-L1, IDO, and Tregs in the melanoma tumor microenvironment is driven by CD8+ T cells", Science Translational Medicine, 5:200ra116.
Stacpoole et al., 2017, "Therapeutic Targeting of the Pyruvate Dehydrogenase Complex/Pyruvate Dehydrogenase Kinase (PDC/PDK) Axis in Cancer", Journal of the National Cancer Institute, 109:djx071.
Sukumar et al., 2013, "Inhibiting glycolytic metabolism enhances CD8+T cell memory and antitumor function", J. Clin. Invest., 123:4479-4488.
Tannahill et al. 2013, "Succinate is an inflammatory signal that induces IL-1β through HIF-1α", Nature, 496:238-242.

(56) References Cited

OTHER PUBLICATIONS

Thompson et al., 2017, "Glutaminase inhibitor CB-839 synergizes with carfilzomib in resistant multiple myeloma cells", Oncotarget, 8:35863-35876.
Wang et al., 2015, "Phase 1 Study of CB-839, a First-in-Class, Orally Administered Small Molecule Inhibitor of Glutaminase in Patients with Relapsed/Refractory Leukemia", Blood, 126:2566.
Warmoes et al., 2014, "Heterogeneity of glycolysis in cancers and therapeutic opportunities", Biochemical pharmacology, 92:12-21.
Weiss et al., 2014, "Regulatory T Cells and Myeloid-Derived Suppressor Cells in the Tumor Microenvironment Undergo Fas-Dependent Cell Death during IL-2/ CD40 Therapy", J. Immunol., 192:5821-5829.
Wellenstein et al., 2018, "Cancer-Cell-Intrinsic Mechanisms Shaping the Tumor Immune Landscape", Immunity, 48:399-416.
Zhou et al., 2010, "Warburg effect in chemosensitivity: Targeting lactate dehydrogenase-A re-sensitizes Taxol-resistant cancer cells to Taxol", Mol. Cancer, 9:33.

* cited by examiner

| | R5P | PEP | F6P | F16BP |
|---|---|---|---|---|
| Average (nm) | 3576 | 2247 | 3179 | 2343 |
| Std Dev (nm) | 408 | 205 | 519 | 363 |

Succinate

Ethylene Glycol

OR

Alkane Diols n = 4, 6, 8, 10

Polyethylene glycol succinate (PEGS)

OR

Poly succinate (1,n) diol [PS(1,n)D]

Polydecanesuccinate (PSA)

% RORγt+ of CD4
0
10
20
30
40
CB-839
CB-839+TRP2
CB-839+PSA
CB-839+PSA(TRP2)
CB-839+PEGS(TRP2)

% GATA3+ of CD4
0
2
4
6
CB-839
CB-839+TRP2
CB-839+PSA
CB-839+PSA(TRP2)
CB-839+PEGS(TRP2)
*

% RORγt+ of CD8
0
2
4
6
8
CB-839
CB-839+TRP2
CB-839+PSA
CB-839+PSA(TRP2)
CB-839+PEGS(TRP2)

SEQUENCE LISTING

```
<160> NUMBER OF SEQ ID NOS: 1

<210> SEQ ID NO 1
<211> LENGTH: 9
<212> TYPE: PRT
```

-continued

```
<213> ORGANISM: Artificial Sequence
<220> FEATURE:
<223> OTHER INFORMATION: Phosphorylated TRP2 peptide

<400> SEQUENCE: 1

Ser Val Tyr Asp Phe Phe Val Trp Leu
1               5
```

*

METABOLITE-BASED POLYMERS, MICROPARTICLES, AND NANOPARTICLES FOR IMMUNOTHERAPY AND METHODS OF TREATING A DISEASE OR DISORDER

CROSS-REFERENCE TO RELATED APPLICATIONS

This application is the U.S. national phase application filed under 35 U.S.C. § 371 claiming benefit to International Patent Application No. PCT/US2021/012691, filed Jan. 8, 2021, which is entitled to priority of U.S. Provisional Application Ser. No. 62/958,465, filed Jan. 8, 2020, the disclosures of which are incorporated by reference herein in their entireties.

REFERENCE TO SEQUENCE LISTING SUBMITTED ELECTRONICALLY

This application contains a sequence listing, which is submitted electronically via EFS-Web as an ASCII formatted sequence listing with a file name "206339-0014-00US_Sequence Listing_ST25.txt", created on Jul. 7, 2022, file size of 688 bytes. Except for changes to the bibliographic information and this Sequence Listing is identical to an ASCII formatted sequence listing with a file name "206339-0014-00WO_Sequence Listing_ST25.txt", created on Jan. 6, 2021, file size of 688 bytes. The sequence listing submitted via EFS-Web is part of the specification and is herein incorporated by reference in its entirety.

BACKGROUND OF THE INVENTION

Inhibition of glycolysis or glutaminase pathway is an effective strategy to prevent cancer cell growth in vitro and in vivo. However, these pathways are also utilized by immune cells to mount responses against cancer cells, and therefore, utilizing immunotherapies in the presence of such inhibitors is challenging.

Thus, there is a need in the art for methods and technologies that can restart metabolic pathways of immune cells (e.g. Dendritic cells (DCs) and T cells) in the presence of metabolic inhibitors and improved methods of treating a disease or disorder by combining immunotherapy with metabolic inhibition. The present invention satisfies this unmet need.

BRIEF SUMMARY OF THE INVENTION

In various embodiments, the present invention relates, in part, to composition comprising a particle that comprises a compound having the structure of Formula (I)

Formula (I)

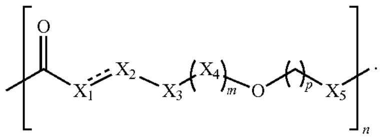

In some embodiments, each occurrence of $X_1$ and $X_2$ is independently $C{=}R_1$, $CR_2$, or $CR_3R_4$.

In some embodiments, each occurrence of $X_3$ and $X_4$ is independently $C{=}R_1$ or $CR_3R_4$.

In some embodiments, each occurrence of $X_5$ is independently O, S, $C{=}R_1$, $CR_3R_4$, $NR_2$, $PR_2$, or $P({=}R_1)(R_2)$.

In some embodiments, the bond between $X_1$ and $X_2$ is a single bond or a double bond.

In one embodiment, when the bond between $X_1$ and $X_2$ is a single bond then $X_1$ and $X_2$ are each independently $C{=}R_1$ or $CR_3R_4$. In another embodiment, when the bond between $X_1$ and $X_2$ is a double bond then $X_1$ and $X_2$ are each $CR_2$.

In some embodiments, each occurrence of $R_1$ is independently O, NH, or S.

In some embodiments, each occurrence of $R_2$, $R_3$, and $R_4$ is independently hydrogen, hydroxyl, carboxyl, alkyl, cycloalkyl, heterocycloalkyl, aryl, or heteroaryl.

In some embodiments, each occurrence of m is independently an integer represented by 0, 1, 2, or 5.

In some embodiments, each occurrence of p is independently an integer from 1 to 50. In some embodiments, each occurrence of p is independently an integer from 1 to 15.

In some embodiments, each occurrence of n is independently an integer from 1 to 1000.

In one embodiment, the compound having the structure of Formula (I) is a compound having the structure of Formula (II)

Formula (II)

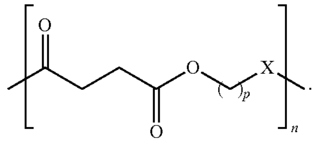

In some embodiments, each occurrence of X is independently O, S, $C{=}R_1$, $CR_3R_4$, $NR_2$, $PR_2$, or $P({=}R_1)(R_2)$.

In various embodiments, the composition further comprises an amino acid sequence. In some embodiments, the amino acid sequence comprises two or more amino acids.

In one embodiment, the amino acid sequence is operably linked to the compound having the structure of Formula (I).

In some embodiments, the composition further comprises an adjuvant. In some embodiments, the adjuvant is operably linked to the compound having the structure of Formula (I), the amino acid sequence, or both.

In another aspect, the present invention relates, in part, to a composition comprising a particle that comprises a compound having the structure of Formula (IV)

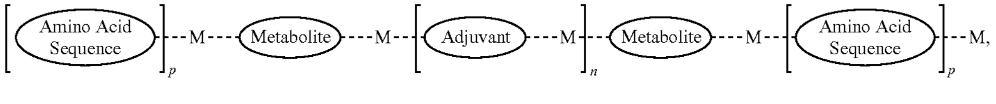

-continued

Formula (V)

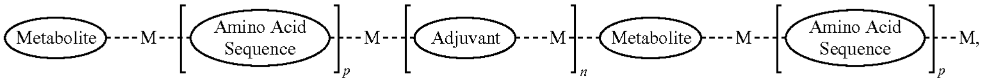

Formula (VI)

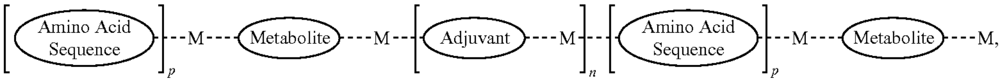

or

Formula (VII)

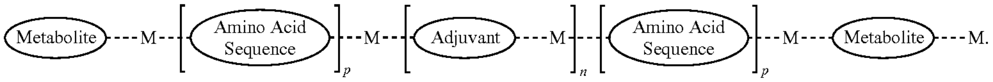

In some embodiments, each occurrence of M is independently Ca, Mg, Na, K, Sr, Zn, Fe, Co, or Cu. In some embodiments, each occurrence of n is independently an integer from 1 to 1000. In some embodiments, each occurrence of p is independently an integer represented by 0 or 1.

In some embodiments, each occurrence of metabolite is independently a metabolite or derivative thereof.

In some embodiments, the amino acid sequence is an isolated protein or fragment thereof, isolated peptide or fragment thereof, antigen or a fragment thereof, tyrosinase-related protein or fragment thereof, tyrosinase-related protein 1 (TRP1) or fragment thereof, tyrosinase-related protein 2 (TRP2) or fragment thereof, phosphorylated tyrosinase-related protein or fragment thereof, phosphorylated TRP1 or fragment thereof, phosphorylated TRP2 or fragment thereof, or any combination thereof.

In some embodiments, the metabolite or derivative thereof is phosphoenolpyruvate, glucono-lactone-6-phosphate, gluconate-6-phosphase, sedoheptulose-7-phosphate, ribulose, ribulose-5-phosphate, xylulose, xylulose-5-phosphate, fructose-1,6-biphosphate, fructose-2,6-biphosphate, glycerate-2-phosphate, glucerate-3-phosphate, malate, fumarate, succinate, isocitrate, citrate, cis-aconitate, malonyl-CoA, acetyl CoA, 3-methylbutyryl CoA, 2-methylbutyryl CoA, 3-ketoacyl CoA, 3-hydroxyacyl CoA, enoyl CoA, 3-ketoacyl functionalized metabolite, 3-hydroxyacyl functionalized metabolite, enoyl functionalized metabolite, fatty acids, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, or any combination thereof.

In some embodiments, the adjuvant is polyinosinic: polycytidylic acid (poly(I:C)) or analog thereof, muramyl dipeptide derivatives (MDP) or analog thereof, Alum and Emulsions, complete Freund's adjuvant (CFA), incomplete Freund's adjuvant (IFA), pattern recognition receptor (PRR) ligands, cyclic guanosine monophosphate-adenosine monophosphate (2'3'-cGAMP), bis-(3'-5')-cyclic dimeric adenosine monophosphate (c-di-AMP), Rp,Rp-isomer of the 2'3'-bisphosphorothioate analog of 3'3'-cyclic adenosine monophosphate (2'3'-c-di-AM(PS)2 (Rp,Rp)), cyclic diguanylate monophosphate-stimulator of interferon genes (c-di-GMP STING)-based vaccine adjuvant, CL401, CL413, CL429, Flagellin, Imiquimod, lipopolysaccharide (LPS) from the gram-negative bacteria *E. coli* 0111:B4 (LPS-EB), monophosphoryl lipid A from *Salmonella minnesota* R595 lipopolysaccharide (MPLA-SM), synthetic monophosphoryl lipid A (MPLA), oligodeoxynucleotides (ODN) 1585, ODN 1826, ODN 2006, ODN 2395, Pam3CSK4, Resiquimod (R848), trehalose-6,6-dibehenate (TDB), or any combination thereof.

In some embodiments, the compound having the structure of Formula (IV) is a compound having the structure of Formula (VIII)

Formula (VIII)
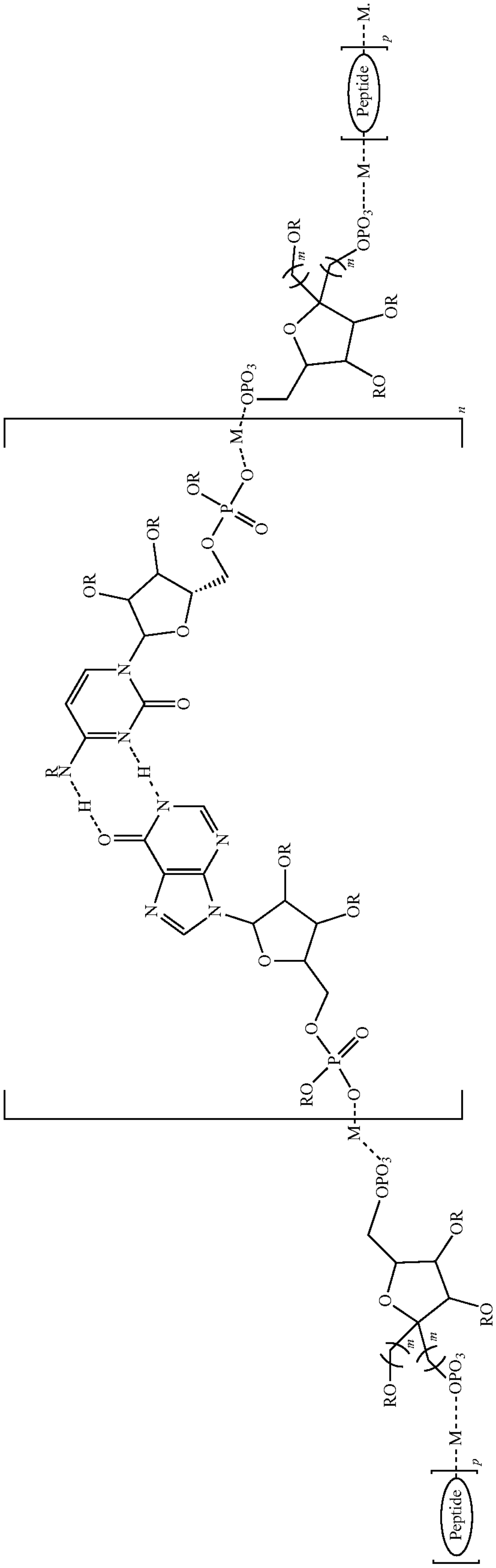

In some embodiments, each occurrence of R is independently hydrogen, hydroxyl, carboxyl, alkyl, cycloalkyl, heterocycloalkyl, aryl, or heteroaryl. In some embodiments, each occurrence of m is independently an integer represented by 0 or 1.

In one embodiment, the particle is a nanoparticle. In another embodiment, the particle is a microparticle.

In some embodiments, the composition further comprises a therapeutic agent.

In one aspect, the present invention relates, in part, to a method of inducing an immune response in a subject. In another aspect, the present invention relates, in part, to a method of preventing or treating a metabolic inhibition of at least one cell in a subject in need thereof. In one embodiment, the at least one cells is an immune cell. In various embodiments, the method comprises administering a therapeutically effective amount of one or more compositions of the present invention to the subject.

In some embodiments, the method further comprises administering a metabolic inhibitor to the subject prior to, simultaneously, or after administering the therapeutically effective amount of the composition to the subject.

In some embodiments, the composition induces at least one glycolysis, tricarboxylic acid (TCA) cycle, pentose phosphate pathway (PPP), activation of the at least one cell, extracellular acidification rate (ECAR), oxygen consumption rate (OCR), mitochondrial respiration, release of a metabolite, pro-inflammatory response, BRAF inhibitors, cancer cell suppression, or any combination thereof.

In some embodiments, the composition decreases the level of at least one immune suppressive cell; increases the level of at least one T cell, type 1 CD8+ T cell (Tc1), type 2 CD8+ T cell (Tc2), IL-17-producing CD8+ T cell (Tc17). T helper cell (Th), Th1, Th17, or effector T cell (Teff); or any combination thereof.

In one embodiment, the composition reduces a cancer cell proliferation.

In one embodiment, the composition reduces a tumor growth. In one embodiment, the composition inhibits (e.g., suppresses, retards, prevents, shrinks, stops, delays, or reverses) a tumor growth. In one embodiment, the composition inhibits a tumor growth in vivo.

In one embodiment, the composition stops a tumor growth.

In one embodiment, the composition stops at least one cancer cell from metastasizing.

In some embodiments, the composition is administered to the subject orally, topically, parenterally, intravenously, intraarterially, intramuscularly, interstitially, subcutaneously, transdermally, intradermally, intrasternally, peritoneally, or any combination thereof.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 1, comprising FIG. 1A depicts a schematic representation of local rescue of immune system from metabolic-inhibition and systemic inhibition of glycolysis or glutaminolysis. FIG. 1B depicts a schematic representation of succinate delivering PEGS microparticles that are phagocytosed by dendritic cell, thereby getting activated and priming T cells to mount an inflammatory immune response against B16F10 melanoma tumor in vivo.

FIG. 5, comprising FIG. 5A depicts a schematic representation of the polymer containing polyinosinic: polycytidylic acid (poly(I:C)) adjuvant, F16BP metabolites, and phosphorylated TRP2 peptide. FIG. 5B depicts a representative scanning electron microscope image of particles. FIG. 5C depicts representative dynamic light scattering data showing the size of the particles on an average less than 10 μm. FIG. 5D depicts representative dynamic light scattering shows that the average size of particles is 2 f 0.3 mm (n=6±stdev). FIG. 5E depicts representative results demonstrating F16BP nanoparticle dynamic light scattering size average size of particles is 220±10 nm (representative of n=3±stdev).

FIG. 6, comprising FIG. 6A depicts representative results demonstrating that DC activation markers (MHCII and MHCII+CD86+) were downregulated upon addition of PFK-15 inhibitor (n=6). FIG. 6B depicts representative MTT assay indicating the IC50 of YUMM1.1 melanoma cells using PFK-15 (IC50=5 PM) (n=6). FIG. 6C depicts representative results demonstrating that F16BP particles rescue ECAR of DCs in the presence of PFK15 glycolysis inhibitor PFK-15. N=3±std. error, *=p<0.05. FIG. 6D depicts representative results demonstrating the ECAR of DCs as determined by seahorse assay (n=10).

FIG. 7, comprising FIG. 7A depicts a schematic representation of the study design for long-term survival in vivo experiments. FIG. 7B depicts a representative results demonstrating the release kinetics of Poly(I:C) from F16BP microparticles. FIG. 7C depicts representative results demonstrating that tumor burden in mice given F16BP particles with PFK15 (gray line) was significantly lowered when compared to PFK15 alone and no treatment. PFK15 by itself also led to significant improvements in tumor burden in mice as compared to no treatment. FIG. 7D depicts representative results demonstrating that the treatment groups do not induce systemic toxicity as there was no significant differences in weights. N=5±std. error; *=p<0.05.

FIG. 8, comprising FIG. 8A depicts representative flow plots. FIG. 8B depicts representative results demonstrating quantification of percentage of T cells in different organs. dLN=draining lymph nodes, ndLN=non-draining contralateral lymph node. Y-axis label on top of each graph. N=5±std. error; *=p<0.05.

FIG. 12, comprising FIG. 12A depicts a schematic representation of representative reaction synthesis of succinate-based polymers and a schematic representation of the structure of PSA polymer. FIG. 12B depicts representative results demonstrating the release kinetics of polymeric microparticles (μg/mg) over 4 days indicating higher release of succinate in PEGS microparticles. Data shown as mean±SEM (n=3). FIG. 12C depicts representative scanning electron microscopy (SEM) images of polymeric microparticles indicating their spherical morphology. FIG. 12D depicts representative size of PEGS particles average diameter=1 μm and representative electron microscope image. FIG. 12E depicts a representative nuclear magnetic resonance of PEGS, showing that succinate is released in sustained manner. FIG. 12F depicts that DCs are able to phagocytose PEGS particles in vitro. Red—rhodamine encapsulated PEGS, blue—nucleus, green—cytosol.

FIG. 13, comprising FIG. 13A depicts representative results demonstrating that PEGS particles rescue DC metabolism in the presence of 30 or 240 nM CB-839 as observed by the ECAR values. FIG. 13B depicts representative results demonstrating that PEGS particles rescue OCR of DCs in the presence of glutaminase inhibitor CB-839. N=10±std. error; *=p<0.05 compared to 30 nM CB839.

FIG. 15, comprising FIG. 15A depicts representative results demonstrating that Th17 populations are upregulated in PSA(TRP2) and PEGS(TRP2) formulations. FIG. 15B depicts representative results demonstrating that there is a significant decrease in Th2 populations in PEGS(TRP2). FIG. 15C depicts representative results demonstrating that PEGS(TRP2) formulation dramatically increases Tc17 population in the tumor. N=5±std. error; *=p<0.05.

FIG. 16, comprising FIG. 16A depicts representative image of PEGS microparticles associated with DCs in vitro. Green: Cytosol; Blue: Nucleus; Red: rhodamine encapsulated PEGS microparticles. FIG. 16B depicts representative confocal microscopy image indicating presence of the same PEGS microparticle in x-y, y-z and x-z planes inside DC. FIG. 16C depicts representative results demonstrating the modulation of DC pathways with PEGS microparticles (n=3). FIG. 16D depicts representative results demonstrating the modulation of intracellular metabolites post treatment with PEGS microparticles (n=3). FIG. 16E depicts representative results demonstrating the extracellular acidification rate of DCs upon treatment with PEGS microparticles (n=10). FIG. 16F depicts representative results demonstrating the maximal respiration of DCs upon treatment with PEGS microparticles (n=10). FIG. 16G depicts representative analyses of modulation of DC function using flow cytometry. FIG. 16H depicts representative results demonstration the modulation of intracellular DC IL-10 (n=6). FIG. 16i depicts representative results demonstration the modulation of intracellular DC IL-12p70 (n=6). FIG. 16J depicts representative results demonstration the modulation of intracellular DC TNFa (n=6). FIG. 16K depicts representative results demonstrating extracellular production of TNFa from DC post treatment with PEGS microparticles (n=5).

FIG. 18, comprising FIG. 18A depicts a schematic representation of experimental design of in vivo experiments. FIG. 18B depicts representative results demonstrating the Kaplan Meir survival curve (n=5). FIG. 18C depicts representative images of B16F10 tumors at day 16. FIG. 18D depicts representative results demonstrating the individual mouse tumors ($mm^2$) of mice in survival study for all treatment groups.

FIG. 19A depicts representative results demonstrating the modulation of DCs in murine lymph nodes treated with different treatment groups (n=5). FIG. 19B depicts representative results demonstrating the modulation of T cells in murine lymph nodes treated with different treatment groups (n=5). FIG. 19C depicts representative image of Trp2 expression in cancer cells in mice and human tumors (n=5). Red=TRP2 expression. Blue=nucleus. Scale bar=100 mm. FIG. 19D depicts representative results demonstrating the modulation of tumor infiltrating lymphocytes (TILs) in mice treated with different treatment groups in vivo (n=5).

DETAILED DESCRIPTION

Figure 1A:
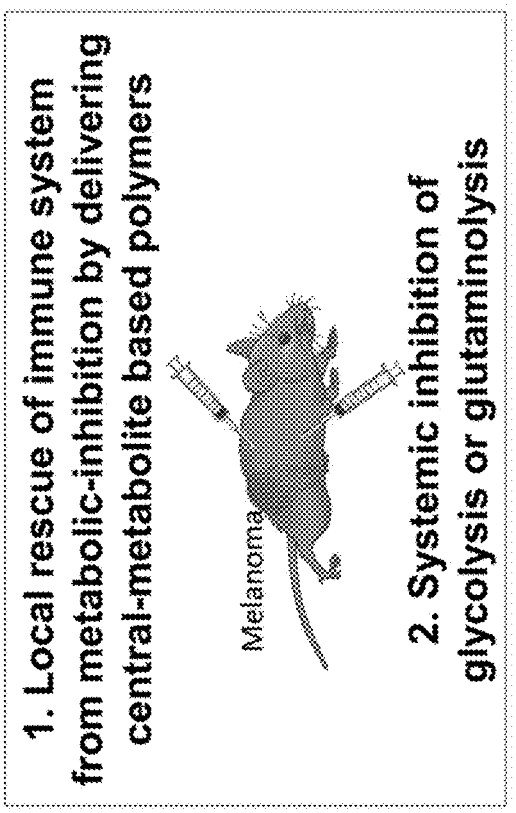
FIG. 1A and FIG. 1B, depicts a schematic representation how particles made of polymers of central-carbon metabolites (targeting Dendritic cells (DCs) via phagocytosis) restart glycolysis/tricarboxylic acid (TCA) cycle in DCs in the presence of metabolic inhibitors and also induce robust vaccine anti-tumor responses in immunocompetent mice.

The present invention provides compounds, microparticles, nanoparticles, and compositions that induce an immune response and prevent or treat a metabolic inhibition in the presence of one or more metabolic inhibitors. The present invention further relates to methods relating to said compounds, microparticles, nanoparticles, and compositions for inducing glycolysis, tricarboxylic acid (TCA) cycle, pentose phosphate pathway (PPP), activation of at least one cell (e.g., immune cell), extracellular acidification rate (ECAR), oxygen consumption rate (OCR), mitochondrial respiration, release of a metabolite, pro-inflammatory response, BRAF inhibitors, cancer cell suppression, and/or increase in the level of immune cells in the presence of one or more metabolic inhibitors. The present invention further relates to methods relating to said compounds, microparticles, nanoparticles, and compositions for reducing cancer cell proliferation in the presence of one or more metabolic inhibitors. The present invention also provides methods of treating a disease or disorder by combining immunotherapy with metabolic inhibition. The present invention additionally provides kits that find use in the practice of the methods of the invention.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent depending on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. The term "alkyl," unless otherwise noted, is also meant to include those derivatives of alkyl defined in more detail below, such as "heteroalkyl", "haloalkyl" and "homoalkyl".

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, Si, P, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: $—O—CH_2—CH_2—CH$, $—CH_2—CH_2—CH_2—OH$, $—CH_2—CH_2—NH—CH_3$, $—CH_2—S—CH_2—CH_3$, and $—CH_2CH_2—S(=O)—CH_3$. Up to two heteroatoms may be consecutive, such as, for example, $—CH_2—NH—OCH_3$, or $—CH_2—CH_2—S—S—CH_3$.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "aromatic" refers to a carbocycle or heterocycle with one or more polyunsaturated rings and having aromatic character, i.e., having (4n+2) delocalized n (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic (e.g., heteroaryl) or non-aromatic (e.g., heterocycloalkyl) in nature. In one embodiment, the heterocycle is a heteroaryl. In one embodiment, the heterocycle is a heterocycloalkyl.

As used herein, the term "heteroaryl" or "heteroaromatic" refers to aryl groups which contain at least one heteroatom selected from N. O, Si, P, and S; wherein the nitrogen and sulfur atoms may be optionally oxidized, and the nitrogen atom(s) may be optionally quaternized. Heteroaryl groups may be substituted or unsubstituted. A heteroaryl group may be attached to the remainder of the molecule through a heteroatom. A polycyclic heteroaryl may include one or more rings that are partially saturated. Examples include tetrahydroquinoline, 2,3-dihydrobenzofuryl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group. For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

The term "derivative" refers to a small molecule that differs in structure from the reference molecule, but retains the essential properties of the reference molecule. A derivative may change its interaction with certain other molecules relative to the reference molecule. A derivative molecule may also include a salt, an adduct, tautomer, isomer, or other variant of the reference molecule.

The term "tautomers" are constitutional isomers of organic compounds that readily interconvert by a chemical process (tautomerization).

The term "isomers" or "stereoisomers" refer to compounds, which have identical chemical constitution, but differ with regard to the arrangement of the atoms or groups in space.

As used herein, the term "polymer" refers to a molecule composed of repeating structural units typically connected by covalent chemical bonds. The term "polymer" is also meant to include the terms copolymer and oligomers. In one embodiment, a polymer comprises a backbone (i.e., the chemical connectivity that defines the central chain of the polymer, including chemical linkages among the various polymerized monomeric units) and a side chain (i.e., the chemical connectivity that extends away from the backbone).

As used herein, the term "nanoparticle" refers to particles having a particle size on the micrometer scale, less than 2,000 nanometers (nm). For example, the nanoparticle may have a particle size up to about 50 nm. In another example, the nanoparticle may have a particle size up to about 10 nm. In another example, the nanoparticle may have a particle size up to about 6 nm. In another example, the nanoparticle may have a particle size up to about 1 nm. In another example, the nanoparticle may have a particle size up to about 0.1 nm. As used herein, "nanoparticle" refers to a number of nanoparticles, including, but not limited to, nanoparticle clusters, nanovesicles, nanocapsule, ectosomes, micellar nanoparticles, lamellae shaped nanoparticles, polymersome nanoparticles, and other nano-size particles of various other small fabrications that are known to those in the art. The shapes and compositions of nanoparticles may be guided during condensation of atoms by selectively favoring growth of particular crystal facets to produce spheres, rods, wires, discs, cages, core-shell structures and many other shapes. The definitions and understandings of the entities falling within the scope of nanocapsule are known to those of skill in the art. However, the following discussion is useful as a further understanding of some of these terms.

For example, a "micellar nanoparticles" or "micelle", a useful article in the employment of a general aspect of the present invention, can generally be thought of as a small —on the order of usually nanometers in diameter—aggregate of amphiphilic linear molecules having a polar, or hydrophilic end and an opposite non-polar, or hydrophobic end. These linear molecules can be comprised of simple molecules, or polymeric chains. A micellar nanoparticles or micelle can also be referred to as an aggregate of surfactant molecules dispersed in a liquid colloid. A typical micellar nanoparticles or micelle in aqueous solution can form an aggregate with the hydrophilic "head" regions in contact with surrounding solvent, and the sequestering of the hydrophobic tail regions in the micelle center. Other and similar definitions, descriptions and understandings of micelles are also known to those of skill in the art.

"Lamella" is a term whose definitions, descriptions and understandings are also known to those of skill in the art. In a very general sense, lamella or lamellae refers to plate-like, gill-shaped or other layered structures.

The definitions, descriptions and understandings of "nanovesicle" are well known to those of skill in the art. For example, "nanovesicle" can refer to a variety of small sac, sac-like or globular structures capable of containing fluid or other material therein "Pharmaceutically acceptable" refers to those properties and/or substances which are acceptable to the subject from a pharmacological/toxicological point of view and to the manufacturing pharmaceutical chemist from a physical/chemical point of view regarding composition, formulation, stability, subject acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar, buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art.

The term "pharmaceutically acceptable salt" refers to any pharmaceutically acceptable salt, which upon administration to the subject is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methane sulphonate, and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine, and basic amino acids salts. However, it will be appreciated that non-pharmaceutically acceptable salts also fall within the scope of the invention since those may be useful in the preparation of pharmaceutically acceptable salts. Procedures for salt formation are conventional in the art.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

As used herein, the terms "therapeutic compound", "therapeutic agent", "drug", "active pharmaceutical", and "active pharmaceutical ingredient" are used interchangeably to refer to chemical entities that display certain pharmacological effects in a body and are administered for such purpose. Non-limiting examples of therapeutic agents include, but are not limited to, antibiotics, analgesics, vaccines, anticonvulsants; anti-diabetic agents, antifungal agents, antineoplastic agents, anti-parkinsonian agents, antirheumatic agents, appetite suppressants, biological response modifiers, cardiovascular agents, central nervous system stimulants, contraceptive agents, dietary supplements, vitamins, minerals, lipids, saccharides, metals, metabolites, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents. In certain embodiments, the one or more therapeutic agents are water-soluble, poorly water-soluble drug or a drug with a low, medium or high melting point. The therapeutic agents may be provided with or without a stabilizing salt or salts.

Some examples of active ingredients suitable for use in the pharmaceutical formulations and methods of the present invention include: hydrophilic, lipophilic, amphiphilic or hydrophobic, and that can be solubilized, dispersed, or partially solubilized and dispersed, on or about the nanoparticle cluster. The active agent-nanoparticle cluster combination may be coated further to encapsulate the agent-nanoparticle cluster combination and may be directed to a target by functionalizing the nanoparticle cluster with, e.g., aptamers and/or antibodies. Alternatively, an active ingredient may also be provided separately from the solid pharmaceutical composition, such as for co-administration. Such active ingredients can be any compound or mixture of compounds having therapeutic or other value when administered to an animal, particularly to a mammal, such as drugs, nutrients, cosmeceuticals, nutraceuticals, diagnostic agents, nutritional agents, and the like. The active agents described herein may be found in their native state, however, they will generally be provided in the form of a salt. The active agents described herein include their isomers, analogs and derivatives.

The term "antibody", as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, multiple chain antibodies, intact immunoglobulins, synthetic antibodies, recombinant antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to at least one portion of an intact antibody, or recombinant variants thereof, and refers to the antigen binding domain, e.g., an antigenic determining variable region of an intact antibody, that is sufficient to confer recognition and specific binding of the antibody fragment to a target, such as an antigen.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

A "chimeric antibody" refers to a type of engineered antibody which contains a naturally-occurring variable region (light chain and heavy chains) derived from a donor antibody in association with light and heavy chain constant regions derived from an acceptor antibody.

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

By the term "recombinant antibody" as used herein, is meant an antibody which is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

An "antibody heavy chain," as used herein, refers to the larger of the two types of polypeptide chains present in antibody molecules in their naturally occurring conformations, and which normally determines the class to which the antibody belongs.

An "antibody light chain," as used herein, refers to the smaller of the two types of polypeptide chains present in antibody molecules in their naturally occurring conformations. Kappa (κ) and lambda (λ) light chains refer to the two major antibody light chain isotypes.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein, the term "stabilizers" refers to either, or both, primary particle and/or secondary stabilizers, which may be polymers or other small molecules. Non-limiting examples of primary particle and/or secondary stabilizers for use with the present invention include, e.g., starch, modified starch, and starch derivatives, gums, including but not limited to polymers, polypeptides, albumin, amino acids, thiols, amines, carboxylic acid and combinations or derivatives thereof. Other examples include xanthan gum, alginic acid, other alginates, benitoniite, veegum, agar, guar, locust bean gum, gum arabic, quince *psyllium*, flax seed, okra gum, arabinoglactin, pectin, tragacanth, scleroglucan, dextran, amylose, amylopectin, dextrin, etc., cross-linked polyvinylpyrrolidone, ion-exchange resins, potassium polymethacrylate, carrageenan (and derivatives), gum karaya and biosynthetic gum. Other examples of useful primary particle and/or secondary stabilizers include polymers such as: polycarbonates (linear polyesters of carbonic acid); microporous materials (bisphenol, a microporous poly(vinylchloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(mides), poly(benzimidazoles), collodion, regenerated proteins, semi-solid cross-linked poly (vinylpyrrolidone).

As used herein, the terms "targeting domain", "targeting moiety", or "targeting group" are used interchangeably and refer to all molecules capable of specifically binding to a particular target molecule and forming a bound complex as described above. Thus, the ligand and its corresponding target molecule form a specific binding pair.

As used herein, the term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

The term "specifically binds", as used herein with respect to an antibody, is meant for an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "associated" as used herein, or "operably linked" refers to a juxtaposition between a regulatory and a coding sequence, wherein the components so described are in a relationship permitting them to function in their intended manner. A regulatory sequence "operably linked" to a coding sequence is ligated in such a way that expression of the coding sequence is achieved under conditions compatible with the control sequences. In case the regulatory sequence is a promoter, it would be known to a skilled person that a double-stranded nucleic acid is preferable. The associated nucleic acid encompasses heterologous nucleic acids. Heterologous nucleic acids refer to nucleic acids derived from a separate genetic source, for example nucleic acids that originate from within the cell but that are not naturally located in the cell, or that are located in a different chromosomal site of the cell. Heterologous nucleic acids may also be derived from other species and may be introduced as a transgene, for example, by transformation. This transgene may be substantially modified from its native form in composition and/or genomic environment through deliberate human manipulation. The term "operably linked" also refers to the juxtaposition between two or more molecules. For example, an amino acid sequence is operably linked to one or more compounds of the present invention. As such, the term "operably linked" refers to one or more covalent bonds, non-covalent bonds, ionic bonds, and/or van der Waal force between two or more molecules.

As used herein, the terms "peptide", "polypeptide", and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or any combination thereof.

As used herein, the terms "amino acid", "amino acidic monomer", or "amino acid residue" refer to any of the twenty naturally occurring amino acids, synthetic amino acids with unnatural side chains, and including both D and L optical isomers.

"Isolated" means altered or removed from the natural state. For example, a peptide naturally present in a living animal is not "isolated," but the same peptide partially or completely separated from the coexisting materials of its natural state is "isolated." An isolated protein can exist in substantially purified form, or can exist in a non-native environment such as, for example, a host cell.

As used herein, the term "fragment," as applied to a nucleic acid, refers to a subsequence of a larger nucleic acid. As used herein, the term "fragment," as applied to a protein or peptide, refers to a subsequence of a larger protein or peptide.

The term "functionally equivalent" as used herein refers to a polypeptide according to the invention that preferably retains at least one biological function or activity of the specific amino acid sequence of either the first or second peptide.

As used herein, the term "immune response" includes T cell mediated and/or B cell mediated immune responses that are influenced by modulation of T cell co-stimulation. The term immune response further includes immune responses that are indirectly effected by T cell activation such as antibody production (humoral responses) and the activation of cytokine responsive cells such as macrophages.

The terms "cells" and "population of cells" are used interchangeably and refer to a plurality of cells, i.e., more than one cell. The population may be a pure population comprising one cell type. Alternatively, the population may comprise more than one cell type. In the present invention, there is no limit on the number of cell types that a cell population may comprise.

As used herein, the term "immune cell" includes cells that are of haematopoietic origin and that play a role in the immune response. Immune cells include lymphocytes, such as B cells and T cells; natural killer cells; myeloid cells, such as monocytes, macrophages, dendritic cells, eosinophils, mast cells, basophils, and granulocytes.

As used herein, the term "T cell" refers to a lymphocyte (e.g., white blood cell) that functions in cell-mediated immunity. In some embodiments, the presence of a T cell receptor (TCR) on the cell surface distinguishes T cells from other lymphocytes. As is known in the art, T cells typically do not present antigens, and rely on other lymphocytes (e.g., natural killer cells and B cells) to aid in antigen presentation. Types of T cells include: T helper cells (TH cells), Memory T cells (Tcm, Tem, or Temra), Regulatory T cells (Treg), Cytotoxic T cells (CTLs), Natural killer T cells (NK cells), gamma delta T cells, and Mucosal associated invariant T cells (MAIT). As used herein, the term "T cell" includes CD4+ T cells and CD8+ T cells. The term T cell also includes both T helper 1 type T cells and T helper 2 type T cells and also Th-IL 17 cells.

As used herein, the term "dendritic cell" or "dendritic cells" (DC) refers to a dendritic cell or cells in its broadest context and includes any DC that is capable of antigen presentation. The term includes all DC that initiate an immune response and/or present an antigen to T lymphocytes and/or provide T-cells with any other activation signal required for stimulation of an immune response. Reference herein to "DC" should be read as including reference to cells exhibiting dendritic cell morphology, phenotype or functional activity and to mutants or variants thereof. The morphological features of dendritic cells may include, but are not limited to, long cytoplasmic processes or large cells with multiple fine dendrites. Phenotypic characteristics may include, but are not limited to, expression of one or more of MHC class I molecules, MHC class II molecules, CD11c, B220, CD8-alpha, CD1, CD4.

As used herein, the term "antigen-presenting cell" or "antigen-presenting cells" or its abbreviation "APC" or "APCs" refers to a cell or cells capable of endocytotic adsorption, processing and presenting of an antigen. The term includes professional antigen presenting cells for example; B lymphocytes, monocytes, dendritic cells (DCs) and Langerhans cells, as well as other antigen presenting cells such as keratinocytes, endothelial cells, glial cells, fibroblasts and oligodendrocytes. The term "antigen presenting" means the display of antigen as peptide fragments bound to MHC molecules, on the cell surface. Many different kinds of cells may function as APCs including, for example, macrophages, B cells, follicular dendritic cells and dendritic cells.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human. In various embodiments, the subject is a human subject, and may be of any race, ethnicity, sex, and age.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

A "therapeutically effective amount" refers to that amount which provides a therapeutic effect for a given condition and administration regimen. In particular, "therapeutically effective amount" means an amount that is effective to prevent, alleviate or ameliorate symptoms of the disease or prolong the survival of the subject being treated, which may be a human or non-human animal. Determination of a therapeutically effective amount is within the skill of the person skilled in the art.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a subject.

As used herein, a "prophylactic" or "preventive" treatment is a treatment administered to a subject who does not exhibit the signs or symptoms of a disease or disorder or exhibits only early signs or symptoms of the disease or disorder for the purpose of decreasing the risk of developing additional or more severe signs of symptoms associated with the disease or disorder.

A disease or disorder is "alleviated" if the severity of a sign or symptom of the disease or disorder, the frequency with which such a sign or symptom is experienced by a subject, or both, is reduced.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Cancer," as used herein, refers to the abnormal growth or division of cells. Generally, the growth and/or life span of a cancer cell exceeds, and is not coordinated with, that of the normal cells and tissues around it. Cancers may be benign, pre-malignant or malignant. Cancer occurs in a variety of cells and tissues, including, but not limited to, the oral cavity (e.g., mouth, tongue, pharynx, etc.), digestive system (e.g., esophagus, stomach, small intestine, colon, rectum, liver, bile duct, gall bladder, pancreas, etc.), respiratory system (e.g., larynx, lung, bronchus, etc.), bones, joints, skin (e.g., basal cell, squamous cell, meningioma, etc.), breast, genital system, (e.g., uterus, ovary, prostate, testis, etc.), urinary system (e.g., bladder, kidney, ureter, etc.), eye, nervous system (e.g., brain, etc.), endocrine system (e.g., thyroid, etc.), soft tissues (e.g., muscle, fat, etc.), and hematopoietic system (e.g., lymphoma, myeloma, leukemia, acute lymphocytic leukemia, chronic lymphocytic leukemia, acute myeloid leukemia, chronic myeloid leukemia, etc.).

The term "inhibit," as used herein, means to suppress or block an activity or function by at least about ten percent relative to a control value. In various embodiments, the activity is suppressed or blocked by at least about 50%, at least about 55%, at least about 60%, at least about 65%, at least about 70%, at least about 75%, at least about 80%, at least about 85%, at least about 90%, or at least about 95%, as compared with a comparator value.

"Instructional material", as that term is used herein, includes a publication, a recording, a diagram, or any other medium of expression which can be used to communicate the usefulness of the nanoparticles or compositions thereof of the present invention in the kit for modulating function of cells, modulating a metabolic inhibition of cells, modulating an immunoresponse, and/or preventing or treating the various diseases or disorders recited herein. Optionally, or alternately, the instructional material may describe one or more methods of for modulating function of cells, modulating a metabolic inhibition of cells, modulating an immunoresponse, and/or preventing or treating the various diseases or disorders in a cell or a tissue of a subject. The instructional material of the kit may, for example, be affixed to a container that contains one or more components of the invention or be shipped together with a container that contains the one or more components of the invention. Alternatively, the instructional material may be shipped separately from the container with the intention that the recipient uses the instructional material and the components cooperatively.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range, such as from 1 to 6, should be considered to have specifically disclosed subranges, such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides compounds, microparticles, nanoparticles, and compositions that induce an immune response and prevent or treat a metabolic inhibition in the presence of one or more metabolic inhibitors. The present invention further relates to methods relating to said compounds, microparticles, nanoparticles, and compositions for inducing glycolysis, tricarboxylic acid (TCA) cycle, pentose phosphate pathway (PPP), activation of at least one cell (e.g., immune cell), extracellular acidification rate (ECAR), oxygen consumption rate (OCR), mitochondrial respiration, release of a metabolite, pro-inflammatory response, BRAF inhibitors, cancer cell suppression, and/or increase in the level of immune cells in the presence of one or more metabolic inhibitors. The present invention further relates to methods relating to said compounds, microparticles, nanoparticles, and compositions for reducing cancer cell proliferation in the presence of one or more metabolic inhibitors. The present invention also provides methods of treating a disease or disorder by combining immunotherapy with metabolic inhibition. The present invention additionally provides kits that find use in the practice of the methods of the invention.

Polymers, Microparticles, and Nanoparticles

In one aspect, the invention provides polymers comprising a metabolite or derivative thereof. In one embodiment, the polymer modulates the function of an immune cell. In one embodiment, the polymer induces an immune response in a subject. In one embodiment, the polymer prevents a metabolic inhibition. In one embodiment, the polymer treats a metabolic inhibition. In one embodiment, the polymer induces an activation of a cell. In one embodiment, the polymer induces an activation of an immune cell. In one embodiment, the polymer induces an activation of a dendritic cell. In one embodiment, the polymer induces glycolysis. In one embodiment, the polymer induces a TCA cycle. In one embodiment, the polymer induces a PPP. In one embodiment, the polymer induces an ECAR. In one embodiment, the polymer induces an OCR. In one embodiment, the polymer induces a mitochondrial respiration. In one embodiment, the polymer induces a release of a metabolite. In one embodiment, the polymer induces a pro-inflammatory response. In one embodiment, the polymer induces one or more BRAF inhibitors. In one embodiment, the polymer induces a cancer cell suppression. In one embodiment, the polymer reduces a cancer cell proliferation. In some embodiments, the polymer increases the level of at least one T cell, type 1 CD8+ T cell (Tc1), type 2 CD8+ T cell (Tc2), IL-17-producing CD8+ T cell (Tc17), T helper cell (Th), Th1, Th17, or effector T cell (Teff). In some embodiments, the polymer decreases the level of at least one immune suppressive cell, Th2, regulatory T cell (Treg), Foxp3, Foxp3+ cell, GATA3, or GATA3+ cell.

In one embodiment, the polymer modulates the function of an immune cell in the presence of one or more metabolic inhibitors. In one embodiment, the polymer induces an immune response in a subject in the presence of one or more metabolic inhibitors. In one embodiment, the polymer prevents a metabolic inhibition in the presence of one or more metabolic inhibitors. In one embodiment, the polymer treats a metabolic inhibition in the presence of one or more metabolic inhibitors. In one embodiment, the polymer induces an activation of a cell in the presence of one or more metabolic inhibitors. In one embodiment, the polymer induces an activation of an immune cell in the presence of one or more metabolic inhibitors. In one embodiment, the polymer induces an activation of a dendritic cell in the presence of one or more metabolic inhibitors. In one embodiment, the polymer induces glycolysis in the presence of one or more metabolic inhibitors. In one embodiment, the polymer induces a TCA cycle in the presence of one or more metabolic inhibitors. In one embodiment, the polymer induces a PPP in the presence of one or more metabolic inhibitors. In one embodiment, the polymer induces an ECAR in the presence of one or more metabolic inhibitors. In one embodiment, the polymer induces an OCR in the presence of one or more metabolic inhibitors. In one embodiment, the polymer induces a mitochondrial respiration in the presence of one or more metabolic inhibitors. In one embodiment, the polymer induces a release of a metabolite in the presence of one or more metabolic inhibitors. In one embodiment, the polymer induces a pro-inflammatory response in the presence of one or more metabolic inhibitors. In one embodiment, the polymer induces one or more BRAF inhibitors in the presence of one or more metabolic inhibitors. In one embodiment, the polymer induces a cancer cell suppression in the presence of one or more metabolic inhibitors. In one embodiment, the polymer reduces a cancer cell proliferation in the presence of one or more metabolic inhibitors. In some embodiments, the polymer increases the level of at least one T cell, Tc1, Tc2, Tc17, Th, Th1, Th17, or Teff in the presence of one or more metabolic inhibitors. In some embodiments, the polymer decreases the level of at least one immune suppressive cell, Th2, Treg, Foxp3, Foxp3+ cell, GATA3, or GATA3+ cell in the presence of one or more metabolic inhibitors. Examples of metabolic inhibitors include, but are not limited to: glycolysis inhibitors, TCA cycle inhibitors, glutaminase inhibitors, CB-839, PFK15, inhibitors of hexokinase, inhibitors of phosphofructokinase, inhibitors of pyruvate kinase, inhibitors of lactate dehydrogenase, inhibitors of fatty acid oxidation (e.g., CPT1a) and fatty acid synthase, inhibitors of enzymes involved in TCA cycle, or any combination thereof.

In various embodiments, the polymer is analyzed using a flow cytometry, enzyme linked immunosorbent assay (ELISA), immunohistochemistry (IHC), immunofluorescence (IF), or any combination thereof. Thus, in various embodiments, the function of the polymer is determined using a flow cytometry, ELISA, IHC, IF, or any combination thereof.

In one embodiment, the metabolite is a carbon-center metabolite. In one embodiment, the metabolite or derivative thereof modulates the function of an immune cell. Examples of carbon-center metabolites include, but are not limited to: phosphoenolpyruvate, glucono-lactone-6-phosphate, gluconate-6-phosphase, sedoheptulose-7-phosphate, ribulose, ribulose-5-phosphate, xylulose, xylulose-5-phosphate, fructose-1,6-biphosphate, fructose-2,6-biphosphate, glycerate-2-phosphate, glucerate-3-phosphate, malate, fumarate, succinate, isocitrate, citrate, cis-aconitate, malonyl-CoA, acetyl CoA, 3-methylbutyryl CoA, 2-methylbutyryl CoA, 3-ketoacyl CoA, 3-hydroxyacyl CoA, enoyl CoA, 3-ketoacyl functionalized metabolite, 3-hydroxyacyl functionalized metabolite, enoyl functionalized metabolite, fatty acids (e.g., caprylic acid, capric acid, lauric acid, myristic acid, palmitic acid, stearic acid, arachidic acid, behenic acid, lignoceric acid, cerotic acid, myristoleic acid, palmitolcic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid), or any combination thereof.

In one aspect, the invention provides a polymer compound or salt thereof having the structure of Formula (I)

Formula (I)

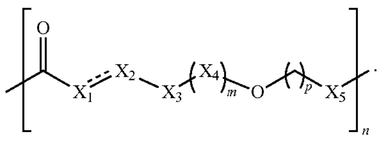

In one embodiment, each occurrence of $X_1$ is independently $C{=}R_1$, $CR_2$, or $CR_3R_4$. In one embodiment, each occurrence of $X_2$ is independently $C{=}R_1$, $CR_2$, or $CR_3R_4$. In one embodiment, each occurrence of $X_3$ is independently $C{=}R_1$ or $CR_3R_4$. In one embodiment, each occurrence of $X_4$ is independently $C{=}R_1$ or $CR_3R_4$. In one embodiment, each occurrence of $X_5$ is independently O, S, $C{=}R_1$, $CR_3R_4$, $NR_2$, $PR_2$, or $P({=}R_1)(R_2)$.

In some embodiments, the bond between $X_1$ and $X_2$ is a single bond or a double bond. In one embodiment, when the bond between $X_1$ and $X_2$ is a single bond, $X_1$ and $X_2$ are each independently $C{=}R_1$ or $CR_3R_4$. In one embodiment, when the bond between $X_1$ and $X_2$ is a double bond, $X_1$ and $X_2$ are each $C{-}R_2$.

In one embodiment, each occurrence of $R_1$ is independently O, NH, or S. In one embodiment $R_1$ is O.

In one embodiment, each occurrence of $R_2$ is independently hydrogen, hydroxyl, carboxyl, alkyl, cycloalkyl, heterocycloalkyl, aryl, or heteroaryl. In one embodiment, $R_2$ is hydrogen. In one embodiment, $R_2$ is hydroxyl.

In one embodiment, each occurrence of $R_3$ is independently hydrogen, hydroxyl, carboxyl, alkyl, cycloalkyl, heterocycloalkyl, aryl, or heteroaryl. In one embodiment, $R_3$ is hydrogen. In one embodiment, $R_3$ is hydroxyl. In one embodiment, $R_3$ is carboxyl.

In one embodiment, each occurrence of $R_4$ is independently hydrogen, hydroxyl, carboxyl, alkyl, cycloalkyl, heterocycloalkyl, aryl, or heteroaryl. In one embodiment, $R_4$ is hydrogen. In one embodiment, $R_4$ is hydroxyl. In one embodiment, $R_4$ is carboxyl.

In one embodiment, each occurrence of m is independently an integer represented by 0, 1, 2, or 5.

In one embodiment, each occurrence of p is independently an integer from 1 to 50. In one embodiment, each occurrence of p is independently an integer from 1 to 15. In one embodiment, each occurrence of p is independently an integer from 1 to 10. In one embodiment, p is 9. In one embodiment, p is 10.

In one embodiment, n is an integer from 1 to 1000.

In various embodiments, the polymer compound or salt thereof having the structure of Formula (I) is a compound having the structure of Formula (II)

Formula (II)

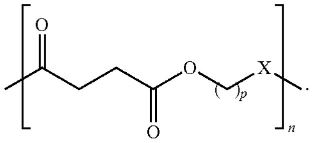

In one embodiment, each occurrence of X is independently O, S, $C{=}R_1$, $CR_3R_4$, $NR_2$, $PR_2$, or $P({=}R_1)(R_2)$. In one embodiment, each occurrence of X is O. Thus, in various embodiments, the polymer compound or salt thereof having the structure of Formula (II) is a compound having the structure of Formula (III)

Formula (III)

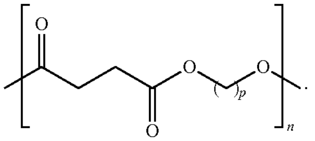

In one embodiment, each occurrence of p is independently an integer from 1 to 50. In one embodiment, each occurrence of p is independently an integer from 1 to 15. In one embodiment, each occurrence of p is independently an integer from 1 to 10. In one embodiment, each occurrence of p is an integer represented by 2. In another embodiment, each occurrence of p is an integer represented by 9. In another embodiment, each occurrence of p is an integer represented by 10. Thus, in one embodiment, the compound having the structure of Formula (III) is polyethylenesuccinate (PEGS). In another embodiment, the compound having the structure of Formula (III) is polydecanesuccinate (PSA).

In one embodiment, n is an integer from 1 to 1000.

In various aspects, the polymer further comprises at least one amino acid. In one embodiment, the amino acid is encapsulated by the polymer. In one embodiment, the amino acid is operably linked to the metabolite or derivative thereof. In one embodiment, the amino acid is a phosphorylated amino acid.

In various aspects, the polymer further comprises an amino acid sequence. In one embodiment, the amino acid sequence is encapsulated by the polymer. In one embodiment, the amino acid sequence is operably linked to the metabolite or derivative thereof. In one embodiment, the amino acid sequence is operably linked to the compound having the structure of Formula (I). In one embodiment, the amino acid sequence is operably linked to the compound having the structure of Formula (II). In one embodiment, the amino acid sequence is operably linked to the compound having the structure of Formula (III).

In various embodiments, the amino acid sequence comprises two or more amino acids. In some embodiments, the amino acid sequence is a peptide or fragment thereof, protein or fragment thereof, or any combination thereof. In various embodiments, the amino acid sequence is a phosphorylated amino acid sequence. Thus, in some embodiments, the amino acid sequence is a phosphorylated peptide or phosphorylated fragment thereof, phosphorylated protein or phosphorylated fragment thereof, or any combination thereof. Examples of amino acid sequences include, but are not limited to: an isolated protein or fragment thereof, isolated peptide or fragment thereof, tyrosinase-related protein or fragment thereof, tyrosinase-related protein 1 (TRP1) or fragment thereof, tyrosinase-related protein 2 (TRP2) or fragment thereof, phosphorylated tyrosinase-related protein or fragment thereof, phosphorylated TRP1 or fragment thereof, phosphorylated TRP2 or fragment thereof, phosphorylated TRP2 peptide as set forth in SEQ ID NO: 1, melanocyte lineage/differentiation antigens, tyrosinase, human homologue of the mouse albino locus, glycoprotein 75 (gp 75), human homologue of the mouse brown locus, glycoprotein 100 (gp100), Pmel17, target for monoclonal antibody HMB45, human homologue of the mouse silver locus, Melan A/MART-1, oncofetal/cancer-testis antigens, melanoma antigen gene (MAGE) family proteins, B melanoma antigen (BAGE) peptides family, GAGE family antigens, esophageal squamous cell carcinoma-1 (NY-ESO-1), cancer-testis antigen 1B(CTAG1B), tumor-specific antigens, peptides with subtle mutations of normal cellular proteins (e.g., coding region mutations), cyclin-dependent kinase 4 or cell division protein kinase 4 (CDK4), β-catenin, mutated peptides activated as a result of cellular transformation, mutated introns, N-acetylglucosaminyltransferase V gene product, MUM-1, p15, antigens identified by monoclonal antibodies, gangliosides (e.g., GM2, GD2, GM3, and GD3), high molecular weight chondroitin sulfate proteoglycan, p97 melanotransferrin, SEREX antigens, D-1, synovial sarcoma/X breakpoint 2 (SSX-2), ovarian cancer antigens, surviving or baculoviral inhibitor of apoptosis repeat-containing 5 (BIRC5), cancer antigen 125 (CA125), carcinoembryonic antigen (CEA), DEAD-box helicase 43 (DDX43), epithelial cell adhesion molecule (EPCAM), folate Receptor Alpha (FOLR1), human epidermal growth factor receptor 2 (Her-2)/neu, melanoma-associated antigen 1 (MAGE-A1), melanoma-associated antigen 2 (M AGE-A2), melanoma-associated antigen 3 (MAGE-A3), melanoma-associated antigen 4 (MAGE-A4), melanoma-associated antigen 6 (MAGE-A6), melanoma-associated antigen 10 (MAGE-A10), melanoma-associated antigen 12 (MAGE-A12), mucin 1 (MUC-1), preferentially expressed antigen in melanoma (PRAME), tumor protein p53 (p53), trophoblast glycoprotein (TPBG), TRT, Wilms tumor protein (WT1), cancer/testis antigen 45 (CT45), breast cancer antigens, telomerase reverse transcriptase (hTERT), Sialyn-Tn, Wilms' Tumor Gene, antigens associated with cancers (e.g., acute lymphoblastic leukemia (ALL), acute myeloid leukemia (AML), cancer in adolescents, adrenocortical carcinoma, acquired immunodeficiency syndrome (AIDS)-related cancers, kaposi sarcoma, lymphoma, AIDS-related lymphoma, primary central nervous system (CNS) lymphoma, anal cancer, appendix cancer, gastrointestinal carcinoid tumors, astrocytomas, childhood astrocytomas, brain cancer, atypical teratoid/rhabdoid tumor, childhood atypical teratoid/rhabdoid tumor, CNS atypical teratoid/rhabdoid tumor, basal cell carcinoma of the skin, skin cancer, bile duct cancer, bladder cancer, childhood bladder cancer, bone cancer (includes Ewing sarcoma and osteosarcoma and malignant fibrous histiocytoma), brain tumors, breast cancer, bronchial tumors, Burkitt lymphoma, non-Hodgkin lymphoma, carcinoid tumor (gastrointestinal), childhood carcinoid tumors, carcinoma of unknown primary, childhood carcinoma of unknown primary, cardiac (heart) tumors, childhood cardiac (heart) tumors, medulloblastoma and other CNS embryonal tumors, childhood brain cancer, germ cell tumor, primary CNS lymphoma, cervical cancer, childhood cervical cancer, childhood cancers, unusual cancers of childhood, cholangiocarcinoma, chordoma, childhood chordoma, chronic lymphocytic leukemia (CLL), chronic myelogenous leukemia (CML), chronic myeloproliferative neoplasms, colorectal cancer, craniopharyngioma, childhood craniopharyngioma, mycosis fungoides and Sézary syndrome, ductal carcinoma in situ (DCIS), embryonal tumors, medulloblastoma and other childhood CNS brain cancers, endometrial cancer, ependymoma, childhood ependymoma, esophageal cancer, esthesioneuroblastoma, Ewing sarcoma, extracranial germ cell tumor, childhood extracranial germ cell tumor, extragonadal germ cell tumor, eye cancer, retinoblastoma, fallopian tube cancer, fibrous histiocytoma of bone, malignant fibrous histiocytoma of bone, osteosarcoma fibrous histiocytoma of bone, gallbladder cancer, gastric (stomach) cancer, gastrointestinal carcinoid tumor, gastrointestinal stromal tumors (GIST), soft tissue sarcoma, germ cell tumors, childhood CNS germ cell tumors, ovarian germ cell tumors, gestational trophoblastic disease, hairy cell leukemia, head and neck cancer, heart tumors, childhood heart tumors, hepatocellular (liver) cancer, histiocytosis, langerhans cell histiocytosis, Hodgkin lymphoma, hypopharyngeal cancer, Islet cell tumors, pancreatic neuroendocrine tumors, kidney (renal cell) cancer, Langerhans cell histiocytosis, Laryngeal cancer, leukemia, lip and oral cavity cancer, liver cancer, lung cancer, such as non-small cell, small cell, pleuropulmonary blastoma, and tracheobronchial tumor, male breast cancer, melanoma, childhood melanoma, intraocular (eye) melanoma, childhood intraocular melanoma, Merkel cell carcinoma, mesothelioma, malignant mesothelioma, metastatic cancer, metastatic squamous neck cancer with occult primary, midline tract carcinoma with NUT gene changes, mouth cancer, multiple endocrine neoplasia syndromes, multiple myeloma/plasma cell neoplasms, mycosis fungoides, myelodysplastic syndromes, myelodysplastic/myeloproliferative neoplasms, myelogenous leukemia, chronic myeloproliferative neoplasms, nasal cavity and paranasal sinus cancer, nasopharyngeal cancer, neuroblastoma, non-small cell lung cancer, oral cancer, lip and oral cavity cancer and oropharyngeal cancer, oropharyngeal cancer, ovarian cancer, childhood ovarian cancer, pancreatic cancer, pancreatic neuroendocrine tumors, papillomatosis, childhood laryngeal, paraganglioma, childhood paraganglioma, paranasal sinus and nasal cavity cancer, parathyroid cancer, penile cancer, pharyngeal cancer, pheochromocytoma, childhood pheochromocytoma, pituitary tumor, plasma cell neoplasm/multiple myeloma, pleuropulmonary blastoma, pregnancy and breast cancer, primary CNS lymphoma, primary peritoneal cancer, prostate cancer, rectal cancer, recurrent cancer, rhabdomyosarcoma, childhood rhabdomyosarcoma, childhood soft tissue sarcoma, salivary gland cancer, sarcoma, childhood vascular tumors, osteosarcoma, uterine sarcoma, Sézary syndrome, childhood skin cancer, small cell lung cancer, small intestine cancer, squamous cell carcinoma of the skin, squamous neck cancer with occult primary, metastatic squamous neck cancer with occult primary, stomach (gastric) cancer, T-cell lymphoma, cutaneous T-cell lymphoma, testicular cancer, childhood testicular cancer, throat cancer, nasopharyngeal cancer, thymoma and thymic carcinoma, thyroid cancer, tracheobronchial tumors, transitional cell cancer of the renal pelvis and ureter, urethral cancer, uterine cancer, endometrial uterine cancer, vaginal cancer, childhood vaginal cancer, vascular tumors, vulvar cancer, Wilms tumor and other childhood kidney tumors, and cancers in young adults), or any combination thereof.

In some embodiments, the polymer further comprises an adjuvant. In one embodiment, the adjuvant is encapsulated by the polymer. In one embodiment, the adjuvant is operably linked to the metabolite or derivative thereof. In one embodiment, the adjuvant is operably linked to the amino acid. In one embodiment, the adjuvant is operably linked to the amino acid sequence. In one embodiment, the adjuvant is operably linked to the metabolite or derivative thereof and the amino acid. In one embodiment, the adjuvant is operably linked to the metabolite or derivative thereof and the amino acid. In one embodiment, the adjuvant is operably linked to the compound having the structure of Formula (I), the amino acid sequence, or both. In one embodiment, the adjuvant is operably linked to the compound having the structure of Formula (II), the amino acid sequence, or both. In one embodiment, the adjuvant is operably linked to the compound having the structure of Formula (111), the amino acid sequence, or both. Examples of adjuvants include, but are not limited to: polyinosinic:polycytidylic adic (poly(I:C)) or analog thereof, muramyl dipeptide derivatives (MDP) or analog thereof, Alum and Emulsions, complete Freund's adjuvant (CFA), incomplete Freund's adjuvant (IFA), pattern recognition receptor (PRR) ligands, cyclic guanosine monophosphate-adenosine monophosphate (2'3'-cGAMP), bis-(3'-5')-cyclic dimeric adenosine monophosphate (c-di-AMP), Rp,Rp-isomer of the 2'3'-bisphosphorothioate analog of 3'3'-cyclic adenosine monophosphate (2'3'-c-di-AM(PS)2 (Rp,Rp)), cyclic diguanylate monophosphate-stimulator of interferon genes (c-di-GMP STING)-based vaccine adjuvant, CL401, CL413, CL429, Flagellin, Imiquimod, lipopolysaccharide (LPS) from the gram-negative bacteria *E. coli* 0111:B4 (LPS-EB), monophosphoryl lipid A from *Salmonella minnesota* R595 lipopolysaccharide (MPLA-SM), synthetic monophosphoryl lipid A (MPLA), oligodeoxynucleotides (ODN) 1585, ODN 1826, ODN 2006, ODN 2395, Pam3CSK4, Resiquimod (R848), trehalose-6,6-dibehenate (TDB), or any combination thereof.

Thus, in one aspect, the invention provides a polymer compound or salt thereof comprising at least one amino acid sequence, at least one metabolite, at least one adjuvant, at least one metal, or any combination thereof. In one embodiment, the invention provides a polymer compound or salt thereof comprising at least one amino acid sequence, at least one metabolite, at least one adjuvant, at least one metal, or any combination thereof that are operably linked to each other in any order. For example, in one aspect, the invention provides a polymer compound or salt thereof having the structure of Formula (IV)

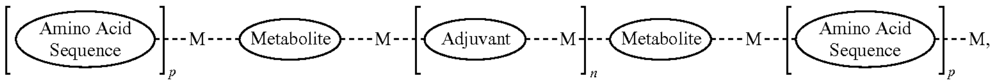

Formula (V)

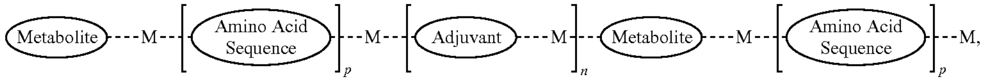

Formula (VI)

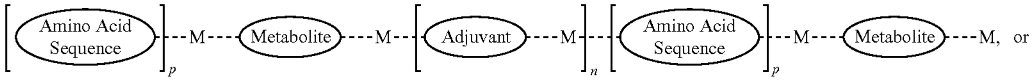

or

Formula (VII)

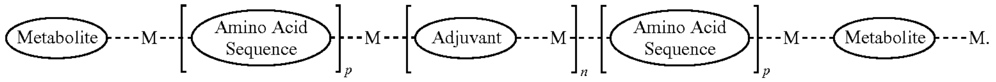

In some embodiments, each occurrence of M is independently Ca, Mg, Na, K, Sr, Zn, Fe, Co, or Cu.

In some embodiments, each occurrence of metabolite is independently a metabolite or derivative thereof.

In some embodiments, each occurrence of n is independently an integer from 1 to 1000.

In some embodiments, each occurrence of p is independently an integer represented by 0 or 1.

In various embodiments, the polymer compound or salt thereof having the structure of Formula (IV) is a compound having the structure of Formula (VIII)

Formula (VIII)
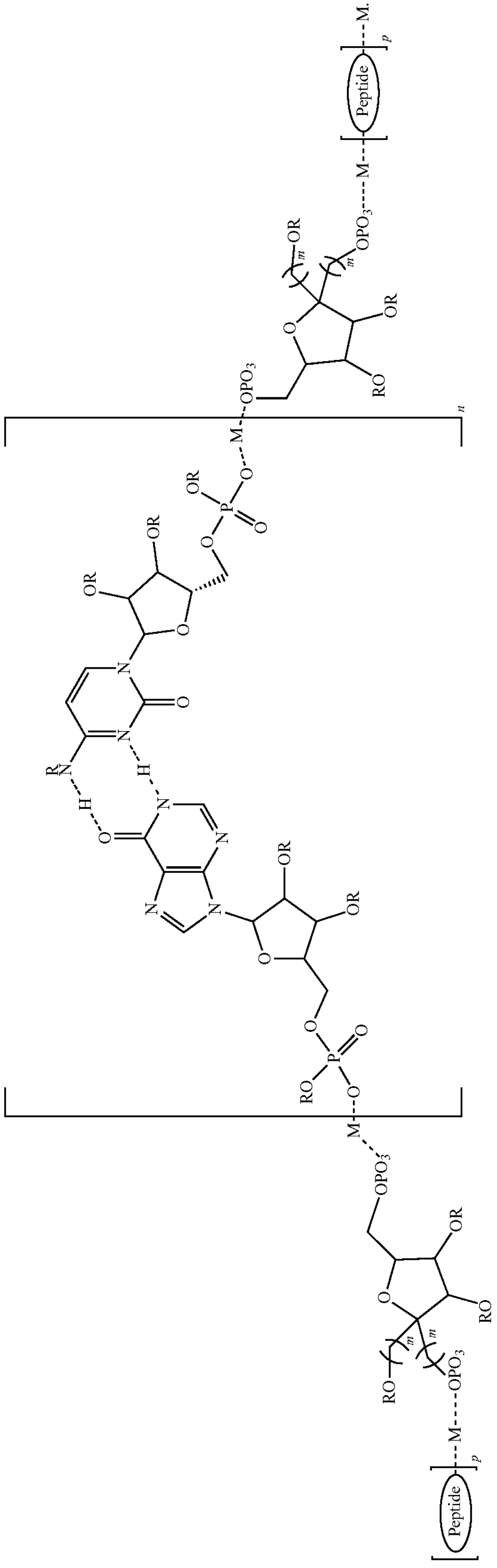

In some embodiments, each occurrence of M is independently Ca, Mg, Na, K, Sr, Zn, Fe, Co, or Cu.

In some embodiments, each occurrence of R is independently hydrogen, hydroxyl, carboxyl, alkyl, cycloalkyl, heterocycloalkyl, aryl, or heteroaryl.

In some embodiments, each occurrence of m is independently an integer represented by 0 or 1.

In some embodiments, each occurrence of n is independently an integer from 1 to 1000.

In some embodiments, each occurrence of p is independently an integer represented by 0 or 1.

In one embodiment, the peptide is phosphorylated TRP2 peptide, each occurrence of M is Ca, each occurrence of R is hydrogen, and each occurrence of p is an integer represented by 1. In one embodiment, the phosphorylated TRP2 peptide comprises an amino acid sequence as set forth in SEQ ID NO: 1. Thus, in one embodiment, the compound having the structure of Formula (IV) is a compound having the structure of Formula (IX)

Formula (IX)
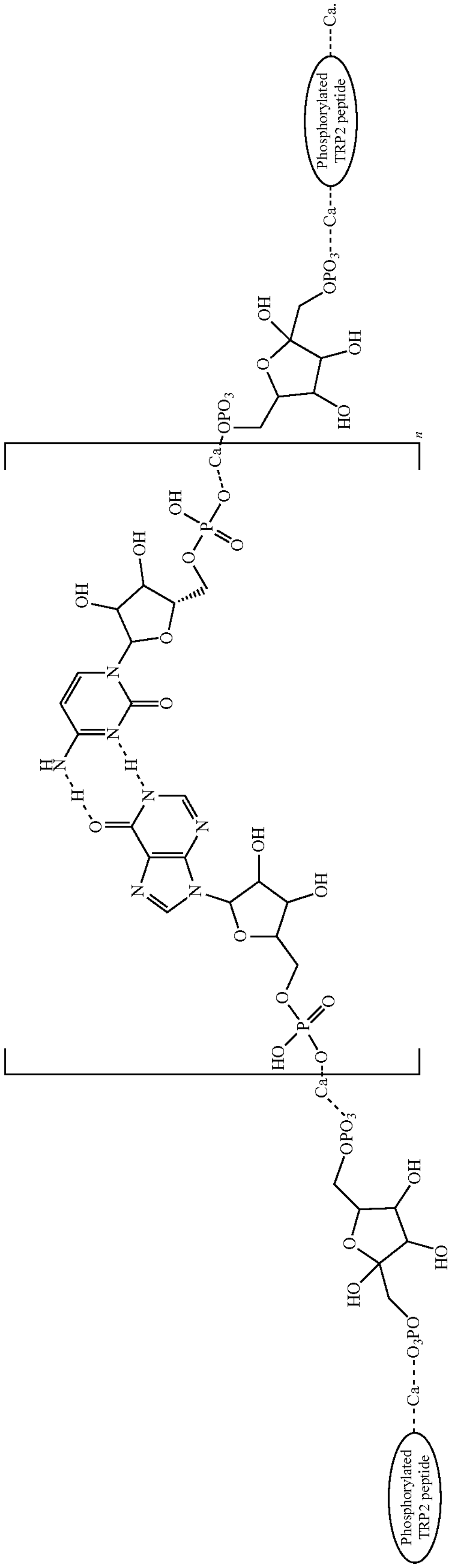

In some embodiments, the polymer is phagocytosed by a cell. Examples of such cells include, but are not limited to, antigen-presenting cells (APC), accessory cell, dendritic cells, T cells, B cells, and macrophages.

In one aspect, the present invention also provides a particle comprising at least one polymer described herein. In one embodiment, the particle is a microparticle. In one embodiment, the particle is a nanoparticle. For example, in one embodiment, one or more compounds having the structure of Formula (I) form the nanoparticle. Thus, in various embodiments, the present invention discloses a nanoparticle comprising at least one compound or salt thereof having the structure of Formula (I). In another embodiment, one or more compounds having the structure of Formula (II) form the nanoparticle. Thus, in various embodiments, the present invention discloses a nanoparticle comprising at least one compound or salt thereof having the structure of Formula (II). In another embodiment, one or more compounds having the structure of Formula (III) form the nanoparticle. Thus, in various embodiments, the present invention discloses a nanoparticle comprising at least one compound or salt thereof having the structure of Formula (III). In another embodiment, one or more compounds having the structure of Formula (IV) form the nanoparticle. Thus, in various embodiments, the present invention discloses a nanoparticle comprising at least one compound or salt thereof having the structure of Formula (IV). In another embodiment, one or more compounds having the structure of Formula (V) form the nanoparticle. Thus, in various embodiments, the present invention discloses a nanoparticle comprising at least one compound or salt thereof having the structure of Formula (V). In another embodiment, one or more compounds having the structure of Formula (VI) form the nanoparticle. Thus, in various embodiments, the present invention discloses a nanoparticle comprising at least one compound or salt thereof having the structure of Formula (VI). In another embodiment, one or more compounds having the structure of Formula (VII) form the nanoparticle. Thus, in various embodiments, the present invention discloses a nanoparticle comprising at least one compound or salt thereof having the structure of Formula (VII). In another embodiment, one or more compounds having the structure of Formula (VIII) form the nanoparticle. Thus, in various embodiments, the present invention discloses a nanoparticle comprising at least one compound or salt thereof having the structure of Formula (VIII). In another embodiment, one or more compounds having the structure of Formula (IX) form the nanoparticle. Thus, in various embodiments, the present invention discloses a nanoparticle comprising at least one compound or salt thereof having the structure of Formula (IX).

In some embodiments, the nanoparticle has an average size (i.e., average diameter of the nanoparticle) of about 0.01 nm to about 10000 nm. For example, in one embodiment, the nanoparticle has an average size (i.e., average diameter of the nanoparticle) of about 0.01 nm. In another embodiment, the nanoparticle has an average size (i.e., average diameter of the nanoparticle) of about 10 nm.

In some embodiments, the nanoparticle is a microparticle. In some embodiments, the microparticle has an average size (i.e., average diameter of the microparticle) of about 0.01 μm to about 1000 μm. For example, in one embodiment, the microparticle has an average size (i.e., average diameter of the microparticle) of about 0.01 μm. In another embodiment, the microparticle has an average size (i.e., average diameter of the microparticle) of about 10 μm.

In some embodiments, the nanoparticle is any type of nanoparticle, including, but not limited to, a nanoparticle cluster, nanovesicle, nanocarrier, microcapsule, ectosomes, micellar nanoparticles, lamellae shaped nanoparticles, polymersome nanoparticles, polymer vesicle, and micro-size particles of various other small fabrications that are known to those in the art.

In some embodiments, the nanoparticle is a biodegradable nanoparticle. For example, in one embodiment, the nanoparticle is biodegradable nanocapsule. In another embodiment, the nanoparticle is a biodegradable polymer vesicle.

In some embodiments, the nanoparticle is phagocytosed by a cell (e.g., immune cell).

In various embodiments, the nanoparticle is analyzed using a flow cytometry, ELISA, IHC, IF, or any combination thereof. Thus, in various embodiments, the function of the nanoparticle is determined using a flow cytometry, ELISA, IHC, IF, or any combination thereof.

In one embodiment, the nanoparticle modulates the function of a cell (e.g., immune cell). In one embodiment, the nanoparticle prevents a metabolic inhibition in a cell (e.g., immune cell). In one embodiment, the nanoparticle treats a metabolic inhibition in a cell (e.g., immune cell). In one embodiment, the nanoparticle induces an activation of a cell (e.g., immune cell). In one embodiment, the nanoparticle induces glycolysis in a cell (e.g., immune cell). In one embodiment, the nanoparticle induces a TCA cycle in a cell (e.g., immune cell). In one embodiment, the nanoparticle induces a PPP in a cell (e.g., immune cell). In one embodiment, the nanoparticle induces an ECAR in a cell (e.g., immune cell). In one embodiment, the nanoparticle induces an OCR in a cell (e.g., immune cell). In one embodiment, the nanoparticle induces a mitochondrial respiration in a cell (e.g., immune cell). In one embodiment, the nanoparticle induces a release of a metabolite in a cell (e.g., immune cell). In one embodiment, the nanoparticle induces a pro-inflammatory response in a cell (e.g., immune cell). In one embodiment, the nanoparticle induces one or more BRAF inhibitors in a cell (e.g., immune cell). In one embodiment, the nanoparticle induces a cancer cell suppression. In one embodiment, the nanoparticle reduces a cancer cell proliferation. In some embodiments, the nanoparticle increases the level of at least one T cell, Tc1, Tc2, Tc17, Th, Th1, Th17, or Teff in a cell. In some embodiments, the nanoparticle decreases the level of at least one immune suppressive cell, Th2, Treg, Foxp3+ cell, or GATA3+ cell. In some embodiments, the nanoparticle decreases the level of at least one Foxp3 or GATA3 in a cell.

In one embodiment, the nanoparticle modulates the function of an immune cell in the presence of one or more metabolic inhibitors. In one embodiment, the nanoparticle prevents a metabolic inhibition in a cell in the presence of one or more metabolic inhibitors. In one embodiment, the nanoparticle treats a metabolic inhibition in a cell in the presence of one or more metabolic inhibitors. In one embodiment, the nanoparticle induces an activation of a cell in the presence of one or more metabolic inhibitors. In one embodiment, the nanoparticle induces glycolysis in a cell in the presence of one or more metabolic inhibitors. In one embodiment, the nanoparticle induces a TCA cycle in a cell in the presence of one or more metabolic inhibitors. In one embodiment, the nanoparticle induces a PPP in a cell in the presence of one or more metabolic inhibitors. In one embodiment, the nanoparticle induces an ECAR in a cell in the presence of one or more metabolic inhibitors. In one embodiment, the nanoparticle induces an OCR in a cell in the presence of one or more metabolic inhibitors. In one embodiment, the nanoparticle induces a mitochondrial respiration in a cell in the presence of one or more metabolic inhibitors. In one embodiment, the nanoparticle induces a release of a metabolite in a cell in the presence of one or more metabolic inhibitors. In one embodiment, the nanoparticle induces a pro-inflammatory response in a cell in the presence of one or more metabolic inhibitors. In one embodiment, the nanoparticle induces one or more BRAF inhibitors in a cell in the presence of one or more metabolic inhibitors. In one embodiment, the nanoparticle induces a cancer cell suppression in the presence of one or more metabolic inhibitors. In one embodiment, the nanoparticle reduces a cancer cell proliferation in the presence of one or more metabolic inhibitors. In some embodiments, the nanoparticle increases the level of at least one T cell, Tc1, Tc2, Tc17, Th, Th1, Th17, or Teff in a cell in the presence of one or more metabolic inhibitors. In some embodiments, the nanoparticle decreases the level of at least one immune suppressive cell. Th2, Treg, Foxp3+ cell, or GATA3+ cell. In some embodiments, the nanoparticle decreases the level of at least one Foxp3 or GATA3 in a cell in the presence of one or more metabolic inhibitors.

Examples of such cells include, but are not limited to, immune cells, antigen-presenting cells (APC), accessory cell, dendritic cells, T cells, B cells, and macrophages.

In one aspect of the invention, the nanoparticle comprises at least one therapeutic agent. In one embodiment, the therapeutic agent is encapsulated by the nanoparticle. In one embodiment, the therapeutic agent is operably linked to the nanoparticle. In one embodiment, the therapeutic agent is encapsulated by the polymer. In one embodiment, the therapeutic agent is operably linked to the polymer.

In one embodiment, the nanoparticle releases at least one therapeutic agent. In one embodiment, the nanoparticle releases at least one therapeutic agent inside or outside the cell. In some embodiments, the nanoparticle decomposes or degrades to release at least one therapeutic agent. Examples of such therapeutic agents include, but are not limited to, one or more drugs, metabolites, metabolic inhibitors, proteins, amino acids, peptides, antibodies, medical imaging agents, therapeutic moieties, one or more non-therapeutic moieties or a combination to target cancer or atherosclerosis, selected from folic acid, peptides, proteins, aptamers, antibodies, siRNA, poorly water soluble drugs, anti-cancer drugs, antibiotics, analgesics, vaccines, anticonvulsants; anti-diabetic agents, antifungal agents, antineoplastic agents, anti-parkinsonian agents, anti-rheumatic agents, appetite suppressants, biological response modifiers, cardiovascular agents, central nervous system stimulants, contraceptive agents, dietary supplements, vitamins, minerals, lipids, saccharides, metals, amino acids (and precursors), nucleic acids and precursors, contrast agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents, or any combinations thereof.

The inhibitors of the invention can be administered alone or in combination with other anti-tumor agents, including cytotoxic/antineoplastic agents and anti-angiogenic agents. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

Other anti-cancer agents that can be used in combination with the disclosed compounds include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate;

methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor, bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor, carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclix-imab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; M1F inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor, platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras famesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor, stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor, translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment, the anti-cancer drug is 5-fluorouracil, taxol, or leucovorin.

In some embodiments, the anti-cancer agent may be a prodrug form of an anti-cancer agent. As used herein, the term "prodrug form" and its derivatives is used to refer to a drug that has been chemically modified to add and/or remove one or more substituents in such a manner that, upon introduction of the prodrug form into a subject, such a modification may be reversed by naturally occurring processes, thus reproducing the drug. The use of a prodrug form of an anti-cancer agent in the compositions, among other things, may increase the concentration of the anti-cancer agent in the compositions of the present disclosure. In certain embodiments, an anti-cancer agent may be chemically modified with an alkyl or acyl group or some form of lipid. The selection of such a chemical modification, including the substituent(s) to add and/or remove to create the prodrug, may depend upon a number of factors including, but not limited to, the particular drug and the desired properties of the prodrug. One of ordinary skill in the art, with the benefit of this disclosure, will recognize suitable chemical modifications.

In one embodiment, the therapeutic agent is one or more non-therapeutic moieties. In some embodiments, the nanoparticle comprises one or more therapeutic moieties, one or more non-therapeutic moieties, or any combination thereof. In some embodiments, the composition comprises folic acid, peptides, proteins, aptamers, antibodies, small RNA molecules, miRNA, shRNA, siRNA, poorly water-soluble therapeutic agents, anti-cancer agents, or any combinations thereof.

In another aspect of the invention, the nanoparticle releases at least one metabolite. In some embodiments, the nanoparticle decomposes or degrades to release at least one metabolite. Thus, in various embodiments, the therapeutic agent is a metabolite. In some embodiments, the metabolite is a carbon-center metabolite.

In one embodiment, the nanoparticle further comprises a targeting domain. In one aspect, the nanoparticle further comprises a targeting domain attached to the surface of the nanoparticle. In some embodiments, the targeting domain is bound to an exterior surface of the nanoparticle and recognizes a particular site of interest in a subject. In one embodiment, the targeting domain binds to at least one associated with a disease or a disorder. In various embodiments, the targeting domain is an antibody, an antibody fragment, a peptide sequence, aptamer, folate, a ligand, a gene component, or any combination thereof. Examples of targeting domains include, but are not limited to antibodies, lymphokines, cytokines, receptor proteins such as CD4 and CD8, solubilized receptor proteins such as soluble CD4, hormones, growth factors, peptidomimetics, synthetic ligands, and the like which specifically bind desired target cells, and nucleic acids which bind corresponding nucleic acids through base pair complementarity. Targeting domains of particular interest include peptidomimetics, peptides, antibodies (e.g., monoclonal antibodies, polyclonal antibodies, recombinant antibodies, human antibodies, humanized antibodies, etc.) and antibody fragments (e.g., the Fab' fragment).

Methods of making and using antibodies are well known in the art. For example, polyclonal antibodies useful in the present invention are generated by immunizing rabbits according to standard immunological techniques well-known in the art. Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alia, which bind to the specific antigens of interest.

One skilled in the art would appreciate, based upon the disclosure provided herein, that the antibody can specifically bind with any portion of an antigen target, which can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

The antibodies can be produced by immunizing an animal such as, but not limited to, a rabbit, a mouse or a camel, with an antigenic protein of the invention, or a portion thereof, by immunizing an animal using a protein comprising at least a portion of the antigen, or a fusion protein including a tag polypeptide portion comprising, for example, a maltose binding protein tag polypeptide portion, covalently linked with a portion comprising the appropriate amino acid residues. One skilled in the art would appreciate, based upon the disclosure provided herein, that smaller fragments of these proteins can also be used to produce antibodies that specifically bind the antigen of interest.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

Further, the skilled artisan, based upon the disclosure provided herein, would appreciate that using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of an antigen of interest can be used to produce antibodies that are specific only for that antigen and do not cross-react non-specifically with other proteins.

The invention encompasses monoclonal, synthetic antibodies, and the like. One skilled in the art would understand, based upon the disclosure provided herein, that the crucial feature of the antibody of the invention is that the antibody bind specifically with an antigen of interest. That is, the antibody of the invention recognizes an antigen of interest or a fragment thereof (e.g., an immunogenic portion or antigenic determinant thereof).

The skilled artisan would appreciate, based upon the disclosure provided herein, that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

In some embodiments, a non-human antibody is humanized, where specific sequences or regions of the antibody are modified to increase similarity to an antibody naturally produced in a human or fragment thereof. A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973), chain shuffling (see, e.g., U.S. Pat. No. 5,565,332), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994). Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323.)

In one embodiment, the antibody fragment provided herein is a single chain variable fragment (scFv). In various embodiments, the antibodies of the invention may exist in a variety of other forms including, for example, Fv, Fab, and (Fab') 2, as well as bi-functional (i.e. bi-specific) hybrid antibodies (e.g., Lanzavecchia et al., Eur. J. Immunol. 17, 105 (1987)). In some embodiments, the antibodies and fragments thereof of the invention bind a cell bearing antigen, TCR, and/or BCR with wild-type or enhanced affinity. In some embodiments, the antibodies and fragments thereof of the invention bind a T cell bearing TCR with wild-type or enhanced affinity. In some embodiments, the antibodies and fragments thereof of the invention bind a B cell bearing BCR with wild-type or enhanced affinity. In various embodiments, a human scFv may also be derived from a yeast display library.

ScFvs can be prepared according to method known in the art (see, for example, Bird et al., (1988) Science 242:423-426 and Huston et al., (1988) Proc. Natl. Acad. Sci. USA 85:5879-5883). ScFv molecules can be produced by linking VH and VL regions together using flexible polypeptide linkers. The scFv molecules comprise flexible polypeptide linker (e.g., a Ser-Gly linker) with an optimized length and/or amino acid composition. The flexible polypeptide linker length can greatly affect how the variable regions of an scFv fold and interact. In fact, if a short polypeptide linker is employed (e.g., between 5-10 amino acids, intrachain folding is prevented. Interchain folding is also required to bring the two variable regions together to form a functional epitope binding site. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715.

The scFv can comprise a polypeptide linker sequence of at least 1, 2, 3, 4, 5, 6, 7, 8, 9, 10, 11, 12, 13, 14, 15, 16, 17, 18, 19, 20, 25, 30, 35, 40, 45, 50, or more amino acid residues between its VL and VH regions. The flexible polypeptide linker sequence may comprise any naturally occurring amino acid. In some embodiments, the flexible polypeptide linker sequence comprises amino acids glycine and serine. In another embodiment, the flexible polypeptide linker sequence comprises sets of glycine and serine repeats such as (Gly4Ser)n, where n is a positive integer equal to or greater than 1. In one embodiment, the flexible polypeptide linkers include, but are not limited to, (Gly4Ser)4 or (Gly4Ser)3. Variation in the flexible polypeptide linker length may retain or enhance activity, giving rise to superior efficacy in activity studies.

In one embodiment, the targeting domain is bound directly to the nanoparticle. In one embodiment, the targeting domain is bound directly to the surface of the nanoparticle. In one embodiment, the targeting domain is bound to the nanoparticle using a linking molecule. In one embodiment, the targeting domain is bound to the surface of the nanoparticle using a linking molecule. The linking molecules useful in the compositions and methods of the present disclosure may be any molecule capable of binding to both the nanoparticle and the targeting domains used in the compositions and methods of the present disclosure. In certain embodiments, the linking molecule may be a hydrophilic polymer. Examples of linking molecules include, but are not limited to, poly(ethylene glycol) and its derivatives, dithiol compounds, dithiol compounds with hydrazide and/or carboxylic functionality, or single thiols and/or amines or their derivatives.

In certain embodiments, the linking molecule and the targeting domain may be bound by one or more covalent bonds. In certain embodiments, the linking molecule, in addition to linking the targeting domain and the nanoparticle, may impart certain benefits upon the compositions of the present disclosure, including, but not limited to, improved hydrophilicity and stability in solution, reduced immunogenic responses upon introduction of the compositions of the present disclosure into a subject, increased circulation time of the compositions of the present disclosure when introduced into the bloodstream of a subject. The choice of a linking molecule may depend upon, among other things, the targeting domain chosen and the subject into which the compositions of the present invention are to be introduced. One of ordinary skill in the art, with the benefit of this disclosure, will recognize additional suitable linking molecules. Such linking molecules are considered to be within the spirit of the present disclosure.

In certain embodiments, the targeting domain may recognize a particular ligand or receptor present in a desired cell and/or tissue type when introduced into a subject. In certain embodiments, the targeting domain may be an antibody that recognizes such a particular ligand or receptor. The use of antibody fragments may also be suitable in the compositions of the present disclosure. The choice of a targeting domain may depend upon, among other things, the cell and/or tissue type into which an at least partial increase in uptake of the compositions of the present disclosure is desired, as well as particular ligand(s) present in such cell and/or tissue types.

In certain embodiments, the targeting domain may be chosen, among other things, to at least partially increase the uptake of the nanoparticle of the present disclosure into a desired cell and/or tissue type when introduced into a subject.

In some embodiments, the suitable targeting domain may be a peptide sequence, DNA fragment, aptamer, RNA, folate, polymer, etc. One of ordinary skill in the art, with the benefit of this disclosure, will recognize other targeting domains that may be useful in the compositions of the present disclosure. Such targeting domains are considered to be within the spirit of the present disclosure.

To obtain additional selectivity, the nanoparticle may be passively or actively targeted to regions of interest, such as organs, vessels, sites of disease, wounds, or a specific organism in a subject. In active targeting, the nanoparticle may be attached to biological recognition agents to allow them to accumulate in or to be selectively retained by or to be slowly eliminated from certain parts of the body, such as specific organs, parts of organs, bodily structures and disease structures and lesions. Active targeting is defined as a modification of biodistribution using chemical groups that will associate with species present in the desired tissue or organism to effectively decrease the rate of loss of nanoparticle from the specific tissue or organism.

Active targeting of the nanoparticle can be considered as localization through modification of biodistribution of the nanoparticle by means of a targeting domain that is attached to or incorporated into the nanoparticle. The targeting domain can associate or bind with one or more receptor species present in the tissue or organism of interest. This binding will effectively decrease the rate of loss of nanoparticle from the specific tissue or organism of interest. In such cases, the nanoparticle can be modified synthetically to incorporate the targeting domain. Targeted nanoparticle can localize because of binding between the ligand and the targeted receptor. Alternatively, the nanoparticle can distribute by passive biodistribution, i.e., by passive targeting, into diseased tissues of interest such as wounds. Thus, even without synthetic manipulation to incorporate a targeting domain that can bind to a receptor site, passively targeted contrast agents can accumulate in a diseased tissue or in specific locations in the subject, such as the skin. The present invention comprises use of a nanoparticle that is linked to a targeting domain that has an affinity for binding to a receptor. Preferably the receptor is located on the surface of a diseased cell or wounded tissue in a human or animal subject.

In some embodiments, the nanoparticle further comprises a biocompatible metal. Examples of biocompatible metals include, but are not limited to, copper, iron oxide, cobalt and noble metals, such as gold and/or silver. One of ordinary skill in the art will be able to select a suitable type of nanoparticle taking into consideration at least the type of imaging and/or therapy to be performed.

Compositions

The present invention also provides various compositions comprising the polymers and/or nanoparticles of the present invention. In one embodiment, the composition is a biodegradable composition. In one embodiment, the composition is a medical biodegradable composition.

In various aspects, the composition comprises: one or more polymers of the present invention and one or more stabilizers. In other aspects, the composition comprises: one or more nanoparticles of the present invention and one or more stabilizers. In various embodiments, the stabilizer to nanoparticle weight ratio is less than 50%. In one embodiment, the stabilizer comprises a biocompatible polymer. Examples of stabilizers include, but are not limited to, biocompatible polymer, a biodegradable polymer, a multifunctional linker, starch, modified starch, and starch derivatives, gums, including but not limited to polymers, polypeptides, albumin, amino acids, thiols, amines, carboxylic acid and combinations or derivatives thereof, citric acid, xanthan gum, alginic acid, other alginates, benitoniite, veegum, agar, guar, locust bean gum, gum arabic, quince *psyllium*, flax seed, okra gum, arabinoglactin, pectin, tragacanth, scleroglucan, dextran, amylose, amylopectin, dextrin, etc., cross-linked polyvinylpyrrolidone, ion-exchange resins, potassium polymethacrylate, carrageenan (and derivatives), gum karaya and biosynthetic gum, polycarbonates (linear polyesters of carbonic acid); microporous materials (bisphenol, a microporous poly(vinylchloride), micro-porous polyamides, microporous modacrylic copolymers, microporous styrene-acrylic and its copolymers); porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly (urethane), cross-linked chain-extended poly(urethane), poly(imides), poly(benzimidazoles), collodion, regenerated proteins, semi-solid cross-linked poly(vinylpyrrolidone), monomeric, dimeric, oligomeric or long-chain, copolymers, block polymers, block co-polymers, polymers, PEG, dextran, modified dextran, polyvinylalcohol, polyvinylpyrollidone, polyacrylates, polymethacrylates, polyanhydrides, polypeptides, albumin, alginates, amino acids, thiols, amines, carboxylic acids, or combinations thereof.

In various embodiments, the composition further comprises nanoparticles dispersed in the organic liquid. In some embodiments, the composition comprises an organic liquid comprising a plurality of nanoparticles of the present invention dispersed therein, and a coating material disposed around the exterior surface of the organic liquid. In one embodiment, the composition comprises an organic liquid and nanoparticles dispersed in organic liquid. In some embodiments, the composition further comprises a coating, which surrounds the exterior surface of organic liquid. Examples of suitable coating materials may include, but are not limited to bovine serum albumin (BSA), lipids, polymers, and combinations thereof. Examples of organic liquids suitable for use in the nanoparticle cluster composition of the present disclosure may include, but are not limited to, perfluorocarbons, such as perfluorocarbons comprising about 5 to about 12 carbons, dodecafluoropentane (DDFP), commercially available from FluoroMed, L.P., Round Rock, Tex., and perfluororpentane.

The compositions are formulated in a pharmaceutically acceptable excipient, such as wetting agents, buffers, disintegrants, binders, fillers, flavoring agents and liquid carrier media such as sterile water, water/ethanol etc. The compositions should be suitable for administration either by topical administration or injection or inhalation or catheterization or instillation or transdermal introduction into any of the various body cavities including the alimentary canal, the vagina, the rectum, the bladder, the ureter, the urethra, the mouth, etc. For oral administration, the pH of the composition is preferably in the acid range (e.g., 2 to 7) and buffers or pH adjusting agents may be used. The contrast media may be formulated in conventional pharmaceutical administration forms, such as tablets, capsules, powders, solutions, dispersion, syrups, suppositories etc.

The compounds, nanoparticles, or compositions of the invention can be formulated and administered to a subject, as now described. The invention encompasses the preparation and use of pharmaceutical compositions comprising the compound, nanoparticle, and/or compositions of the invention useful for the delivery of a therapeutic agent, such as metabolite, to a cell (e.g., delivery of succinate to a dendritic cell). The invention also encompasses the preparation and use of pharmaceutical compositions comprising the compound, nanoparticle, and/or compositions of the invention useful for the treatment of a disease or disorder (e.g., any disease or disorder associated with increased level of a pro-inflammatory cytokine; decreased level of an anti-inflammatory cytokine; decreased level of a T regulatory cell; or any combination thereof). The invention also encompasses the preparation and use of pharmaceutical compositions comprising the compound, nanoparticle, and/or compositions of the invention useful for the growth or regeneration of biological tissue (e.g., wound healing).

Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The pharmaceutical compositions useful for practicing the invention may be administered to deliver a dose of between about 0.01 ng/kg/day and 500 mg/kg/day.

In various embodiments, the pharmaceutical compositions useful in the methods of the invention may be administered, by way of example, systemically, parenterally, or topically, such as, in oral formulations, inhaled formulations, including solid or aerosol, and by topical or other similar formulations. In addition to the appropriate therapeutic composition, such pharmaceutical compositions may contain pharmaceutically acceptable carriers and other ingredients known to enhance and facilitate drug administration. Other possible formulations, such as nanoparticles, liposomes, resealed erythrocytes, and immunologically based systems may also be used to administer an appropriate modulator thereof, according to the methods of the invention.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals, patients, and subjects of all sorts. Modification of pharmaceutical compositions suitable for administration to humans in order to render the compositions suitable for administration to various animals and patients is well understood, and the ordinarily skilled veterinary pharmacologist can design and perform such modification with merely ordinary, if any, experimentation.

Pharmaceutical compositions that are useful in the methods of the invention may be prepared, packaged, or sold in formulations suitable for oral, rectal, vaginal, parenteral, topical, pulmonary, intranasal, buccal, intravenous, ophthalmic, intrathecal and other known routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and U.S. Pat. No. 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent.

Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or *arachis* oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, cutaneous, subcutaneous, intraperitoneal, intravenous, intramuscular, intracisternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers.

Such a formulation is administered in the manner in which snuff is taken i.e. by rapid inhalation through the nasal passage from a container of the powder held close to the nares. Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, contain 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 nanomaters to about 2000 micrometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa.

Typically dosages of the compound of the invention which may be administered to an animal or patient, preferably a human, range in amount from about 0.01 mg to about 100 g per kilogram of body weight of the animal or patient. While the precise dosage administered will vary depending upon any number of factors, including, but not limited to, the type of animal and type of disease state being treated, the age of the animal or patient and the route of administration. Preferably, the dosage of the compound will vary from about 0.01 mg to about 500 mg per kilogram of body weight of the animal or patient. The compound can be administered to an animal or patient as frequently as several times daily, or it can be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, patient, etc.

Administration of the compounds of the present invention or the compositions thereof may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art.

One or more suitable unit dosage forms having the therapeutic agent(s) of the invention, which, as discussed below, may optionally be formulated for sustained release, can be administered by a variety of routes including parenteral, including by intravenous and intramuscular routes, as well as by direct injection into the diseased tissue. For example, the therapeutic agent may be directly injected into the muscle. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly(lactic acid) or ethylenevinylacetate copolymers. In addition to being incorporated, these agents can also be used to trap the compound in microcapsules.

Accordingly, the composition of the present invention may be delivered via various routes and to various sites in a mammal body to achieve a particular effect (see, e.g., Rosenfeld et al., 1991; Rosenfeld et al., 1991a. Jaffe et al., supra; Berkner, supra). One skilled in the art will recognize that although more than one route can be used for administration, a particular route can provide a more immediate and more effective reaction than another route. In one embodiment, the composition described above is administered to the subject by subretinal injection. In other embodiments, the composition is administered by intravitreal injection. Other forms of administration that may be useful in the methods described herein include, but are not limited to, direct delivery to a desired organ (e.g., the eye), oral, inhalation, intranasal, intratracheal, intravenous, intramuscular, subcutaneous, intradermal, and other parental routes of administration. Additionally, routes of administration may be combined, if desired. In another embodiments, route of administration is subretinal injection or intravitreal injection.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

Methods of Prevention, Treatment, and Immunotherapy

The polymers, nanoparticles, and/or compositions thereof of the present invention can be used to modulate the function of a cell (e.g., immune cell). Thus, in one embodiment, the present invention provides a method to induce an immune response. In one embodiment, the present invention provides a method to induce a metabolism of a cell (e.g., immune cell). In one embodiment, the present invention provides a method to induce an activation of a cell (e.g., immune cell). In one embodiment, the present invention provides a method to induce glycolysis. In one embodiment, the present invention provides a method to induce a TCA cycle. In one embodiment, the present invention provides a method to induce a PPP. In one embodiment, the present invention provides a method to induce an ECAR. In one embodiment, the present invention provides a method to induce an OCR. In one embodiment, the present invention provides a method to induce a mitochondrial respiration. In one embodiment, the present invention provides a method to induce a release of a metabolite in a cell (e.g., immune cell). In one embodiment, the present invention provides a method to induce a pro-inflammatory response. In one embodiment, the present invention provides a method to induce one or more BRAF inhibitors. In one embodiment, the present invention provides a method to induce a cancer cell suppression. In one embodiment, the present invention provides a method to reduce a cancer cell proliferation.

Thus, in various embodiments, the present invention provides a method of treating or preventing a disease or disorder associated with cell function, immune cell function, metabolic inhibition, immune response, activation of a cell, activation of an immune cell, glycolysis, TCA cycle, PPP, ECAR, OCR, mitochondrial respiration, level of a metabolite in a cell, pro-inflammatory response, a BRAF inhibitor, or any combination thereof in a subject in need thereof. In one embodiment, the present invention provides a method of preventing or treating a metabolic inhibition of a cell (e.g., immune cell) in a subject in need thereof. In one embodiment, the present invention provides a method of treating or preventing a disease or disorder in a subject in need thereof. In one embodiment, the disease or disorder is a disease or disorder associated with abnormal immune cell function in a subject in need thereof. In one embodiment, the present invention provides a method of treating or preventing a cancer in a subject in need thereof.

In some embodiments, the method comprises increasing the level of at least one T cell, Tc1, Tc2, Tc17, Th, Th1, Th17, or Teff. In some embodiments, the method comprises decreasing the level of at least one immune suppressive cell, Th2, Treg, Foxp3, Foxp3+ cell, GATA3, or GATA3+ cell. Thus, in one embodiment, the present invention provides a method of treating or preventing a disease or disorder associated with T cells, Tc1, Tc2, Tc17, Th. Th1, Th17, Teff, immune suppressive cell, Th2, Treg, Foxp3, Foxp3+ cell, GATA3, GATA3+ cell, or any combination thereof in a subject in need thereof.

In various aspects, the polymers, nanoparticles, and/or compositions thereof of the present invention can be used to modulate the function of a cell (e.g., immune cell) in the presence of one or more metabolic inhibitors. Thus, in one embodiment, the present invention provides a method to induce an immune response in the presence of one or more metabolic inhibitors. In one embodiment, the present invention provides a method to induce a metabolism of a cell (e.g., immune cell) in the presence of one or more metabolic inhibitors. In one embodiment, the present invention provides a method to induce an activation of a cell (e.g., immune cell) in the presence of one or more metabolic inhibitors. In one embodiment, the present invention provides a method to induce glycolysis in the presence of one or more metabolic inhibitors. In one embodiment, the present invention provides a method to induce a TCA cycle in the presence of one or more metabolic inhibitors. In one embodiment, the present invention provides a method to induce a PPP in the presence of one or more metabolic inhibitors. In one embodiment, the present invention provides a method to induce an ECAR in the presence of one or more metabolic inhibitors. In one embodiment, the present invention provides a method to induce an OCR in the presence of one or more metabolic inhibitors. In one embodiment, the present invention provides a method to induce a mitochondrial respiration in the presence of one or more metabolic inhibitors. In one embodiment, the present invention provides a method to induce a release of a metabolite in a cell (e.g., immune cell) in the presence of one or more metabolic inhibitors. In one embodiment, the present invention provides a method to induce a pro-inflammatory response in the presence of one or more metabolic inhibitors. In one embodiment, the present invention provides a method to induce one or more BRAF inhibitors in the presence of one or more metabolic inhibitors. In one embodiment, the present invention provides a method to induce a cancer cell suppression in the presence of one or more metabolic inhibitors. In one embodiment, the present invention provides a method to reduce a cancer cell proliferation in the presence of one or more metabolic inhibitors.

Thus, in various embodiments, the present invention provides a method of treating or preventing a disease or disorder associated with immune cell function, metabolic inhibition, immune response, activation of a cell, activation of an immune cell, glycolysis, TCA cycle, ECAR, OCR, PPP, ECAR, OCR, mitochondrial respiration, level of a metabolite in a cell (e.g., immune cell), pro-inflammatory response, a BRAF inhibitor, or any combination thereof in a subject in need thereof in the presence of one or more metabolic inhibitors. In one embodiment, the present invention provides a method of preventing or treating a metabolic inhibition of a cell (e.g., immune cell) in a subject in need thereof in the presence of one or more metabolic inhibitors. In one embodiment, the present invention provides a method of treating or preventing a disease or disorder in a subject in need thereof in the presence of one or more metabolic inhibitors. In one embodiment, the disease or disorder is a disease or disorder associated with abnormal immune cell function in a subject in need thereof in the presence of one or more metabolic inhibitors. In one embodiment, the present invention provides a method of treating or preventing a cancer in a subject in need thereof in the presence of one or more metabolic inhibitors.

In some embodiments, the method comprises increasing the level of at least one T cell, Tc1, Tc2, Tc17, Th, Th1, Th17, or Teff in the presence of one or more metabolic inhibitors. In some embodiments, the method comprises decreasing the level of at least one immune suppressive cell, Th2, Treg, Foxp3, Foxp3+ cell, GATA3, or GATA3+ cell in the presence of one or more metabolic inhibitors. Thus, in one embodiment, the present invention provides a method of treating or preventing a disease or disorder associated with T cells, Tc1, Tc2, Tc17, Th, Th1, Th17, Teff, immune suppressive cell, Th2, Treg, Foxp3, Foxp3+ cell, GATA3, or GATA3+ cell, or any combination thereof in a subject in need thereof in the presence of one or more metabolic inhibitors.

In one embodiment, the method comprises administering at least one polymer described herein to the subject. In one embodiment, the method comprises administering at least one nanoparticle described herein to the subject. In one embodiment, the method comprises administering at least one composition described herein to the subject. Thus, in some embodiments, the polymer, nanoparticle, or composition of the present invention activates at least one cell (e.g., immune cell, dendritic cell (DC)). In some embodiments, the polymer, nanoparticle, or composition induces an activation of DCs, function of DCs, immune response, activation of a cell, glycolysis, TCA cycle, ECAR, OCR, PPP, ECAR, OCR, mitochondrial respiration, level of a metabolite in a cell (e.g., immune cell), pro-inflammatory response, a BRAF inhibitor, release of a metabolite in DCs, cancer cell suppression, or any combination thereof. In one embodiment, the polymer, nanoparticle, or composition reduces a cancer cell proliferation. In some embodiments, the polymer, nanoparticle, or composition increases the level of at least one T cell, Tc1, Tc2, Tc17, Th, Th1, Th17, or Teff. In some embodiments, the polymer, nanoparticle, or composition decreases the level of at least one immune suppressive cell, Th2, Treg, Foxp3, Foxp3+ cell, GATA3, or GATA3+ cell.

In one embodiment, the method comprises administering a nanoparticle comprising a compound having the structure of Formula (I)-(IX) to a subject. In one embodiment, the nanoparticle releases the metabolite from the polymer. For example, in one embodiment, the method comprises administering a nanoparticle comprising a compound having the structure of Formula (III), wherein the nanoparticle releases succinate.

In one embodiment, the metabolite modulates the function of one or more cells. For example, in one embodiment, the metabolite activates immune cells. In one embodiment, the metabolite activates DCs.

The present invention also provides methods of treating a disease or disorder by combining immunotherapy with metabolic inhibition. Thus, in various aspects of the invention, the method further comprises administering a metabolic inhibitor to the subject prior to, simultaneously, or after administering the therapeutically effective amount of the composition to the subject. Thus, in various aspects of the invention, the method comprises administering at least one polymer described herein to the subject in the presence of one or more metabolic inhibitors. In one embodiment, the method comprises administering at least one nanoparticle described herein to the subject in the presence of one or more metabolic inhibitors. In one embodiment, the method comprises administering at least one composition described herein to the subject in the presence of one or more metabolic inhibitors.

Thus, in some embodiments, the polymer, nanoparticle, or composition of the present invention activates at least one cell (e.g., immune cell, DCs) in the presence of one or more metabolic inhibitors. In some embodiments, the polymer, nanoparticle, or composition induces an activation of DCs, function of DCs, immune response, activation of a cell, glycolysis, TCA cycle, ECAR, OCR, PPP, ECAR, OCR, mitochondrial respiration, level of a metabolite in a cell (e.g., immune cell), pro-inflammatory response, a BRAF inhibitor, release of a metabolite in DCs, cancer cell suppression, or any combination thereof in the presence of one or more metabolic inhibitors. In one embodiment, the polymer, nanoparticle, or composition reduces a cancer cell proliferation in the presence of one or more metabolic inhibitors. In some embodiments, the polymer, nanoparticle, or composition increases the level of at least one T cell, Tc1, Tc2, Tc17, Th, Th1, Th17, or Teff in the presence of one or more metabolic inhibitors. In some embodiments, the polymer, nanoparticle, or composition decreases the level of at least one immune suppressive cell, Th2, Treg, Foxp3, Foxp3+ cell, GATA3, or GATA3+ cell in the presence of one or more metabolic inhibitors.

In some embodiments, the nanoparticle delivers an additional therapeutic agent to the subject. For example, in one embodiment, the nanoparticle encapsulates an additional therapeutic agent and delivers the therapeutic agent to the subject. Thus, in one embodiment, the method of the invention delivers metabolite and an additional therapeutic agent to a subject in need thereof. In one embodiment, the therapeutic agent is any therapeutic agent described herein.

Any therapeutic agent or any combination of therapeutic agents disclosed herein may be administered to a subject to treat a disease or disorder. The therapeutic agents herein can be formulated in any number of ways, often according to various known formulations in the art or as disclosed or referenced herein.

In one embodiment, the invention provides a method for increasing the level of a metabolite in the subject. In one embodiment, the method comprises administering to the subject a nanoparticle of the invention. For example, in one embodiment, the method comprises administering a nanoparticle comprising a compound having the structure of Formula (I)-(IX), wherein the nanoparticle releases the metabolite from the polymer. Thus, in one embodiment, the method increases metabolites including, but not limited to, succinic acid, citric acid, isocitric acid, maleic acid, fumaric acid, or any combination thereof.

In some embodiments, the invention provides a method for increasing the level of Th, Th1, Th17, Tc1, Tc17, Teff, Teff to Treg ratio, RORγt, or any combination thereof. In some embodiments, the invention provides a method for decreasing the level of immune suppressive cell, Th2, Treg, Foxp3, Foxp3+ cell, GATA3, GATA3+ cell, or any combination thereof in the subject. Thus, in one embodiment, the present invention provides a method of treating or preventing a disease or disorder associated with decreased level of T cells, Tc1, Tc2, Tc17, Th, Th1, Th17, Teff, or any combination thereof in a subject in need thereof. In one embodiment, the present invention provides a method of treating or preventing a disease or disorder associated with increased level of immune suppressive cell, Th2, Treg, Foxp3, Foxp3+ cell, GATA3, GATA3+ cell, or any combination thereof in a subject in need thereof.

In certain embodiments, the method of treating a disease or disorder comprises a "triggered" functionality. In other words, the system may remain inert in the body until specifically triggered. In some embodiments, the polymer or nanoparticle is used advantageously in therapeutic applications such as to first target the polymer or nanoparticle to a specified location, and then trigger them into an activated state. Sometimes referred to as a "dual targeted delivery system," this feature may minimize the side effects of systemic therapeutic agents. For example, in some embodiments, upon delivering the polymer or nanoparticle to a specific cell, a reagent, such as water, proton, acid, or protonated water, may be applied to the cell thereby causing the release of a therapeutic agent from the polymer or nanoparticle. In some embodiments, this may provide a clinician the ability to control and visualize drug therapy noninvasively.

In some embodiments, the size (e.g., average diameter of the nanoparticle) of the compound, nanoparticle, or composition of the present invention allows for passive diffusion into cells. In some embodiments, where the compound, nanoparticle, or composition is on a smaller scale, the small size (e.g., average diameter of the nanoparticle) allows the compound, nanoparticle, or compositions to travel almost anywhere in the body where therapy may need to be performed. For example, in some embodiments, the method comprises compounds or nanoparticles that act as a hydrolysis triggered therapeutic agent delivery and therapeutic agent release systems.

In some embodiments, the compound, nanoparticle, or composition undergo uptake into cells. In some embodiments, the compound, nanoparticle, or composition undergo uptake into macrophage cells. In some embodiments, the compound, nanoparticle, or composition undergo uptake into dendritic cells. For example, in some embodiments, the compound, nanoparticle, or composition can be coated with dextran to target the macrophage cells, since macrophages have dextran receptors. In various embodiments, the method further comprises allowing the compound, nanoparticle, or composition to accumulate in a region of the biological tissue, wherein the targeting domain facilitated accumulation of the compound, nanoparticle, or composition in the region.

In various aspects, the compound, nanoparticle, or composition of the present invention can be used alone or in combination with a therapeutic agent to deliver a therapeutic agent payload to a target cell. Often, the therapeutic agent may be released based on the degradation of, e.g., a controlled release biodegradable matrix and/or polymer. However, it has been found that the compounds or nanoparticles of the present invention can also deliver their payload by hydrolysis disruption of the compounds or nanoparticles.

The preferred dosage of the compound or nanoparticle will vary according to a number of factors, such as the administration route, the age, weight and species of the subject, but in general containing in the order of from 1 μmol/kg to 1 mmol/kg bodyweight of the compound or nanoparticle.

Administration may be topical, parenteral (e.g., intravenously, intraarterially, intramuscularly, interstitially, subcutaneously, transdermally, or intrasternally), or into an externally voiding body cavity (e.g., the gastrointestinal tract, rectum, bladder, uterus, vagina, nose, ears or lungs), peritoneally, orally, intradermal, ocular, in an animate human or non-human (e.g., mammalian, reptilian or avian) body.

Kits

The present invention also pertains to kits useful in the methods of the invention. Such kits comprise various combinations of components useful in any of the methods described elsewhere herein, including for example, materials for modulating function of cells using the nanoparticles of the invention, materials for modulating a metabolic inhibition of cells using the nanoparticles of the invention, materials for modulating an immunoresponse using the nanoparticles of the invention, materials for treating a disease or disorder using the nanoparticles of the invention, and instructional material. For example, in one embodiment, the kit comprises components useful for the modulation of cell function in a subject. In a further embodiment, the kit comprises components useful for the modulation of a metabolic inhibition in a cell. In a further embodiment, the kit comprises components useful for the modulation of an immunoresponse in a subject. In a further embodiment, the kit comprises components useful for the treatment of a disease or disorder in a subject.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Figure 1B:
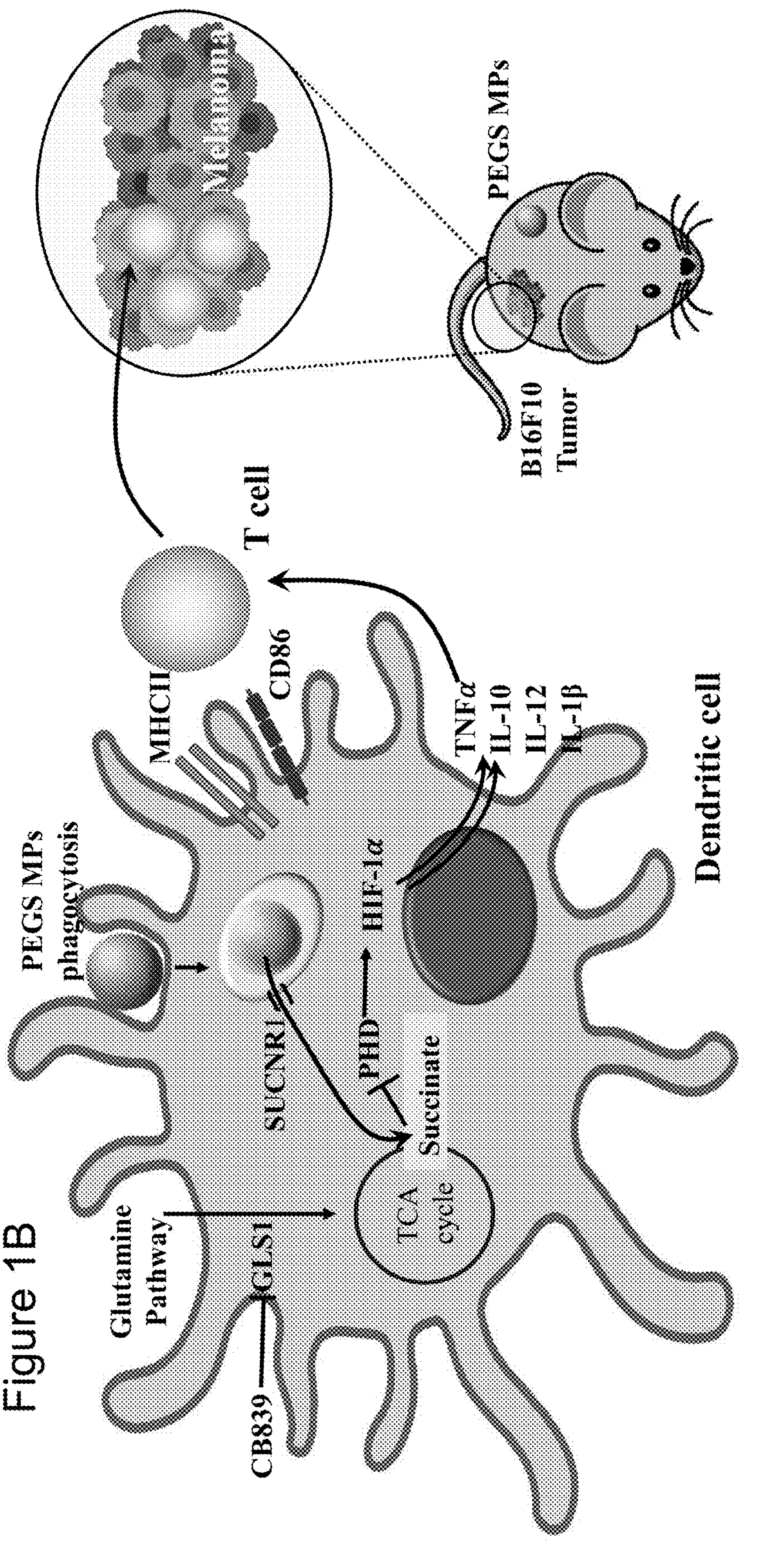

Example 1: Metabolic Rescue of Dendritic Cells (DCs) for Melanoma Immunotherapy The main goals of the study described herein was to (1) develop technologies that can restart metabolic pathways of immune cells (e.g., Dendritic cells (DCs) and T cells) in the presence of metabolic inhibitors and (2) develop treatment regimens combining immunotherapy with metabolic inhibition. Importantly, particles made of polymers of central-carbon metabolites (targeting DCs via phagocytosis) can restart glycolysis/TCA cycle in DCs in the presence of metabolic inhibitors and can also induce robust vaccine anti-tumor responses in immunocompetent mice (FIG. 1A and FIG. 1B).

The disclosed data demonstrated that novel particles can be generated with central-carbon metabolites as the backbone of polymers. Specifically, polymer of fructose, 1,6 biphosphate (F16BP), and poly(ethyleneglycolsuccinate) (PEGS) were utilized to generate particles. F16BP and PEGS based particles were able to rescue the metabolic inhibition, as observed by up-regulated extracellular acidification rate (ECAR) and oxygen consumption rate (OCR) in bone marrow derived DCs (BMDCs) in glycolysis stress test. Moreover, F16BP particles were able to rescue the activation and glycolysis of BMDCs from glycolysis inhibition (PFK15, a PFKFB3 inhibitor in glycolysis pathway) and PEGS particles were able to rescue activation of DCs, mitochondrial respiration and glycolytic capacity of BMDCs from glutaminase inhibition (CB-839, a glutaminase1—mitochondrial respiration inhibitor). When delivered subcutaneously, PEGS encapsulating TRP2 peptide (180-188 SVYDFFVWL) particles were able to reduce the growth of B16F10 (wild type BRAF) in the presence of CB-839 provided systemically. Moreover, F16BP particles encapsulating poly (I:C) as adjuvant and TRP2 peptide antigen were able to reduce YUMM1.1 (BRAFV600E mutant) tumors in immunocompetent C57BL/6j mice, in the presence of PFK15 provided systemically. Both F16BP and PEGS particle-based vaccines were able to induce robust cancer vaccine responses in mice. Notably, PEGS particles were able to induce vaccine responses even in the absence of adjuvants. Moreover, the reduction in tumor burden in mice was correlated with increase in T helper 1 (Th1), Th17, Tc1 and Tc17 cells, and reduced exhausted CD8+ T cells in tumors and draining lymph nodes, and led to significant improvement in survival of mice (nearly 2-fold).

Cancer Immunotherapies Target T Cells in the Tumor Microenvironment (TME)

Success of tumor immunotherapy is strongly influenced by the ratio of pro-inflammatory cells (T effector-Teff cells involved in killing cancer cells) to immunosuppressive cells (regulatory T cells-Treg). Numerous studies have demonstrated that elevated Teff/Tregs ratios are associated with clearance of tumors in mice, while low Teff/Tregs ratios are associated with aggressive, fast-growing tumors and poor prognoses.

Tregs are a subset of CD4+ T cells that release IL-10 cytokines to induce immunosuppression in the tumor microenvironment. Moreover, Tregs suppress immune reaction against cancer cells and promote cellular reproduction. Therefore, decreasing Treg population in the TME is beneficial for immunotherapies.

Teff cells are a group of cells that induce a pro-inflammatory response against the tumor. Teff comprise of IFNγ+ CD8+Tc1, IFN-γ+CD4+Th1, CD8+RORgt+Tc17 cells and IL-17+CD4+ Th17 cells. These cells contribute to prevention of cancer cell proliferation and increase in their population is beneficial for tumor treatment. Thus, increasing Teff/Tregs ratios is important to generate a potent immune response against tumors, which can be accomplished by either enhancing Teff populations and/or depleting Tregs.

Anti-Tumor DCs, Cytolytic T Cells and Cancer Cells Utilize Glycolysis and Glutaminase for Energy Pre-clinical therapies that target cancer cell glycolysis (Warburg effect) and glutaminase pathways show promise in melanoma treatment. However, these can also have a direct effect on effector T cell population, which also utilizes glycolysis for energy. In fact, activated DCs and cytolytic CD8+ T cells utilize glycolysis. Therefore, inhibiting the glycolysis/glutaminase pathway can be beneficial for developing robust melanoma growth suppression, but may sacrifice the function of immunotherapy.

Succinate Activate Immune Cells, and PFKFB3 is Critical and Rate Limiting Step for Glycolysis Succinate modulates innate immune responses by stabilizing HIF1α, succinylation of several proteins and generation of pro-inflammatory IL-1α in macrophages. Moreover, succinate levels are increased in immune cells via upregulation of glutaminase in the presence of LPS, and thus, glutaminase-succinate pathway is an important target for activation of immune cells.

The rate limiting step in glycolysis is phosphofructokinase, which is activated by fructose 2,6-biphosphate. Notably, PFKFB3 enzymes are responsible for maintaining the levels of fructose 2,6-biphosphate, and thus are important target for cancer treatment as well.

Figure 2:
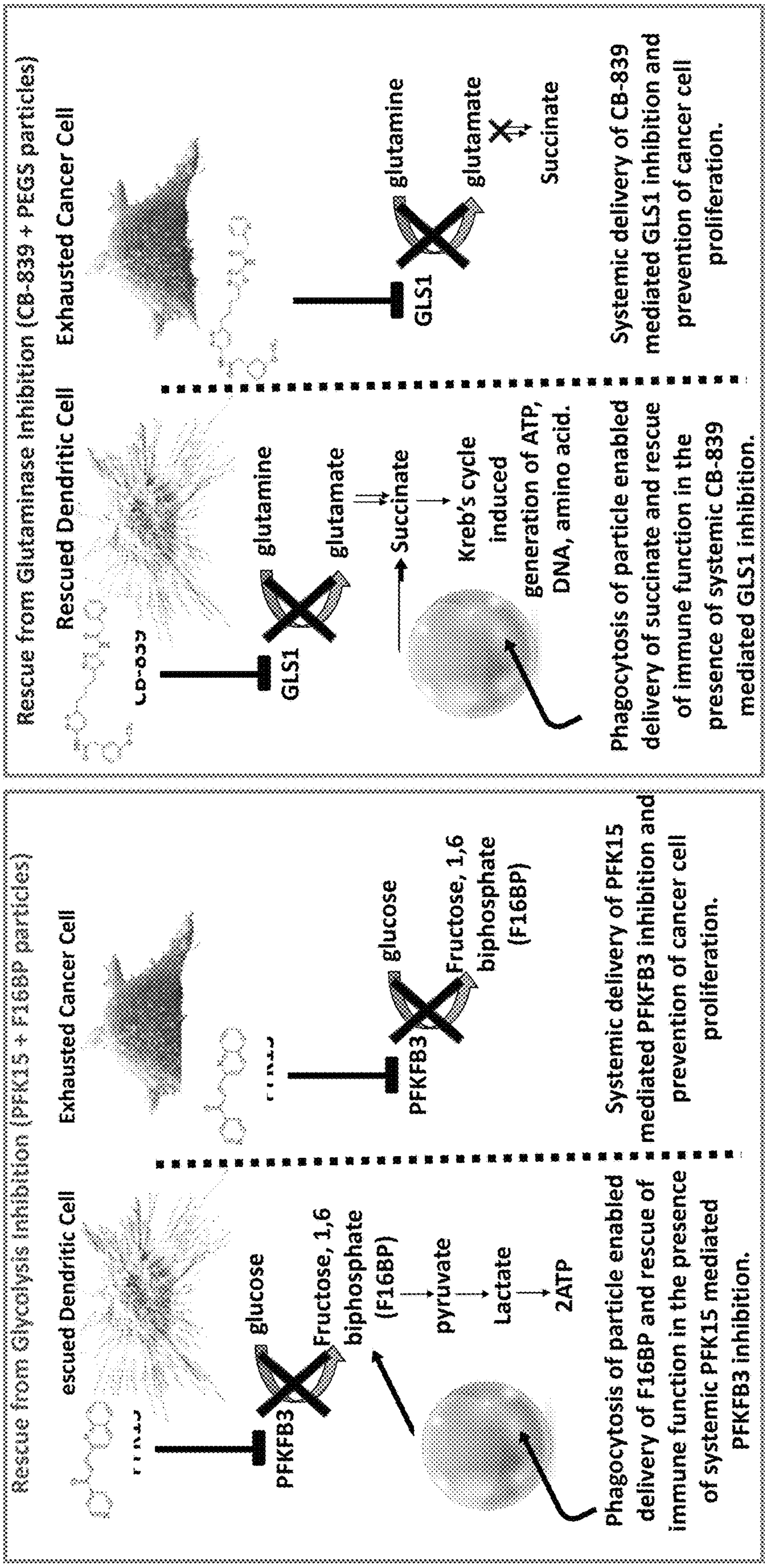
FIG. 2 depicts the general mechanism by which immunometabolism modulating particles function to rescue DCs from glycolysis inhibition (left) and glutaminase inhibition (right).
Figure 17:
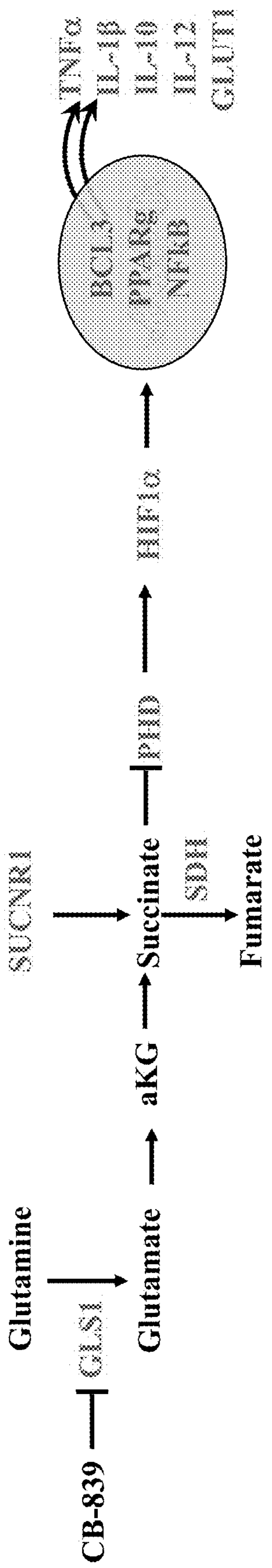
FIG. 17 depicts a schematic representation of the intracellular DC pathway showing genes modified by treatment with PEGS microparticles leading to DC activation.
Figure 18A:
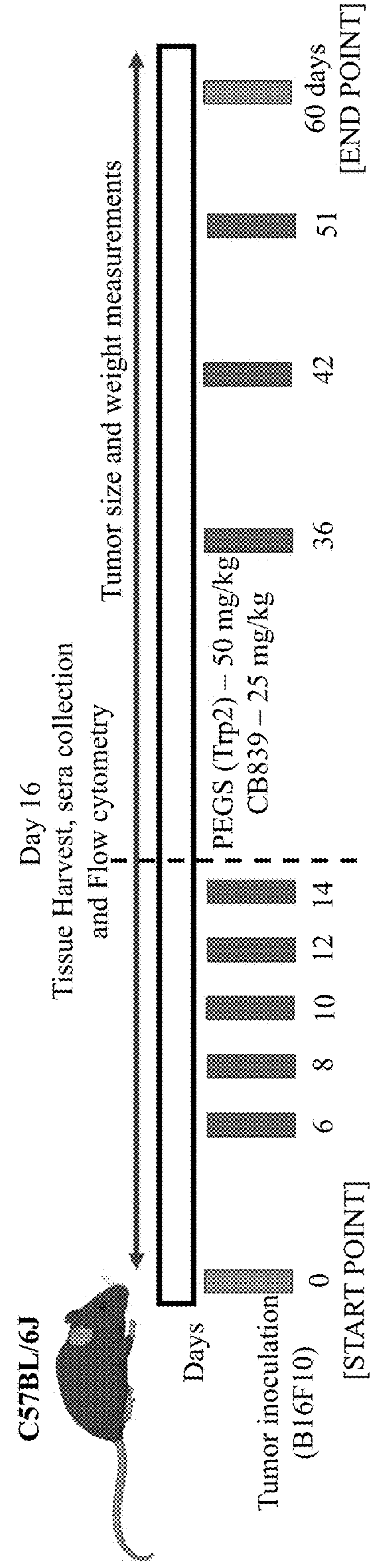
FIG. 18A through FIG. 18D, depicts representative results demonstrating that PEGS microparticles delay tumor growth in mice.
Figure 18C:
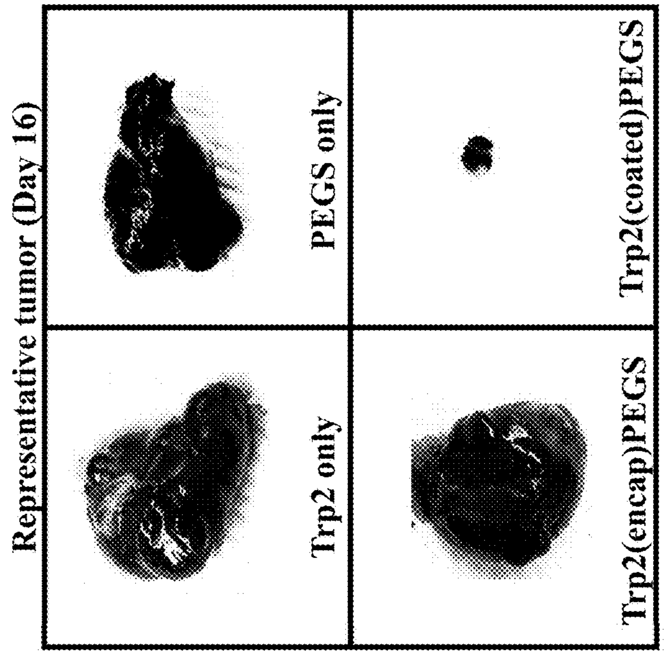
Figure 18B:
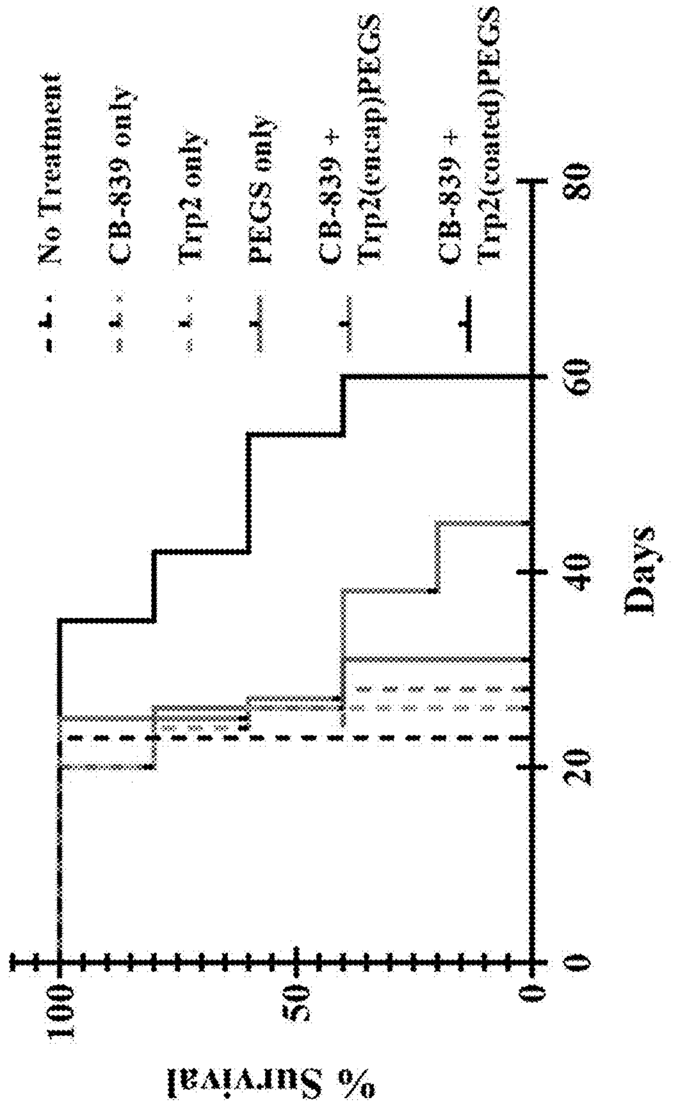
Figure 18D:
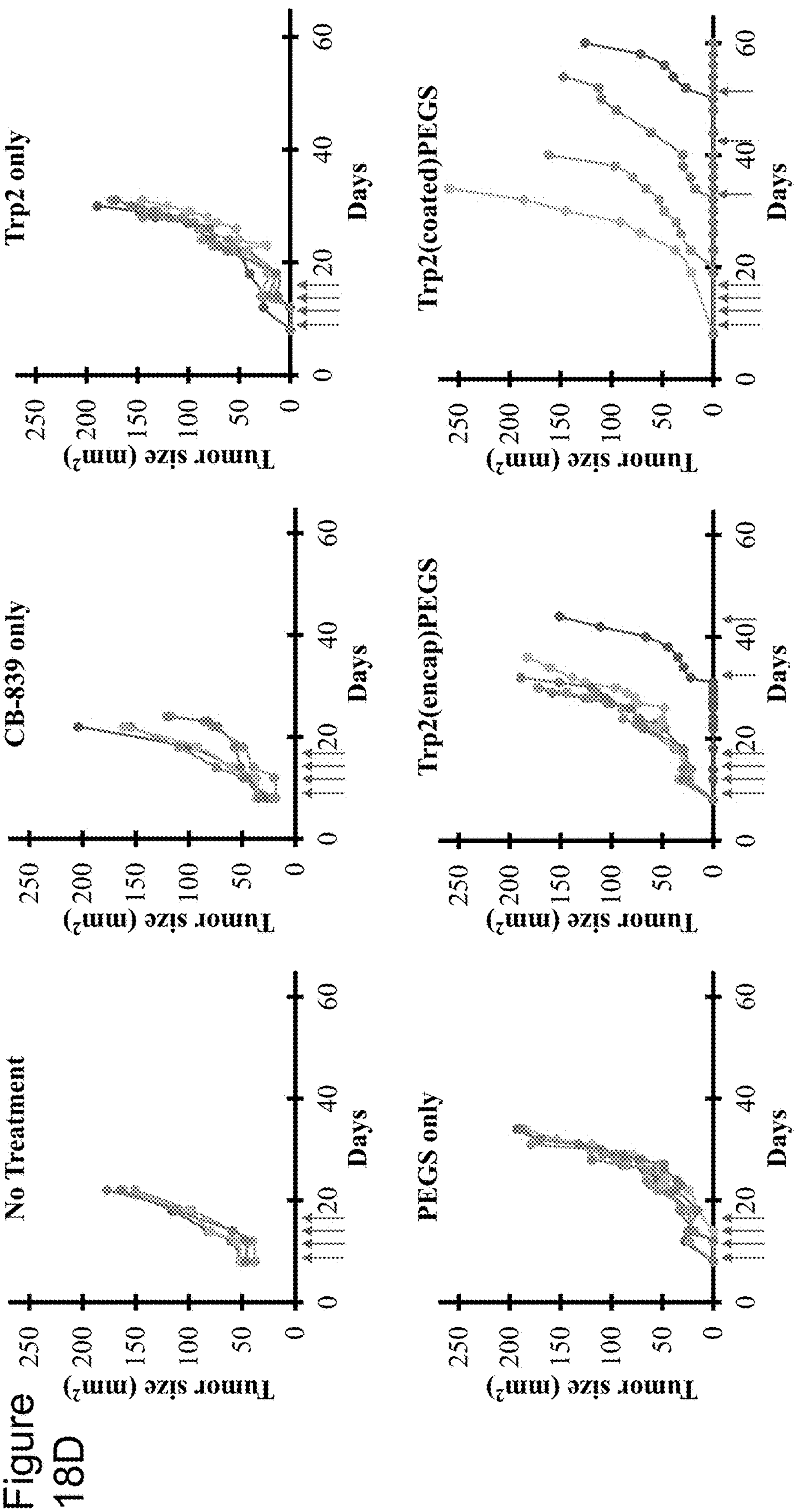
Figure 19:
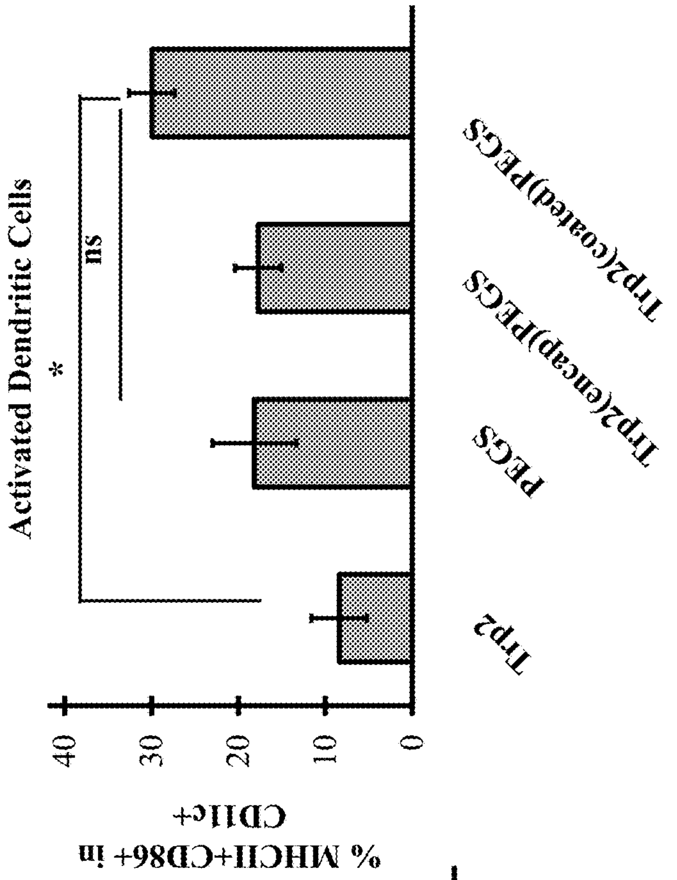
FIG. 19, comprising
Figure 19A:
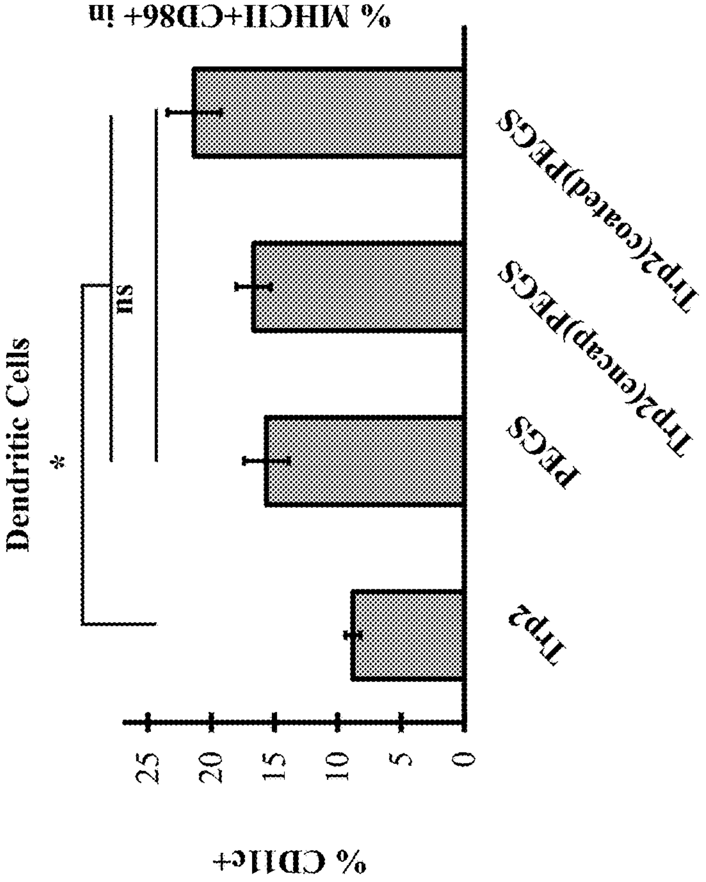
FIG. 19A through FIG. 19D, depicts representative results demonstrating succinate based microparticles modulate DC and T cell function in vivo. Data shown as mean t SEM.
Figure 19B:
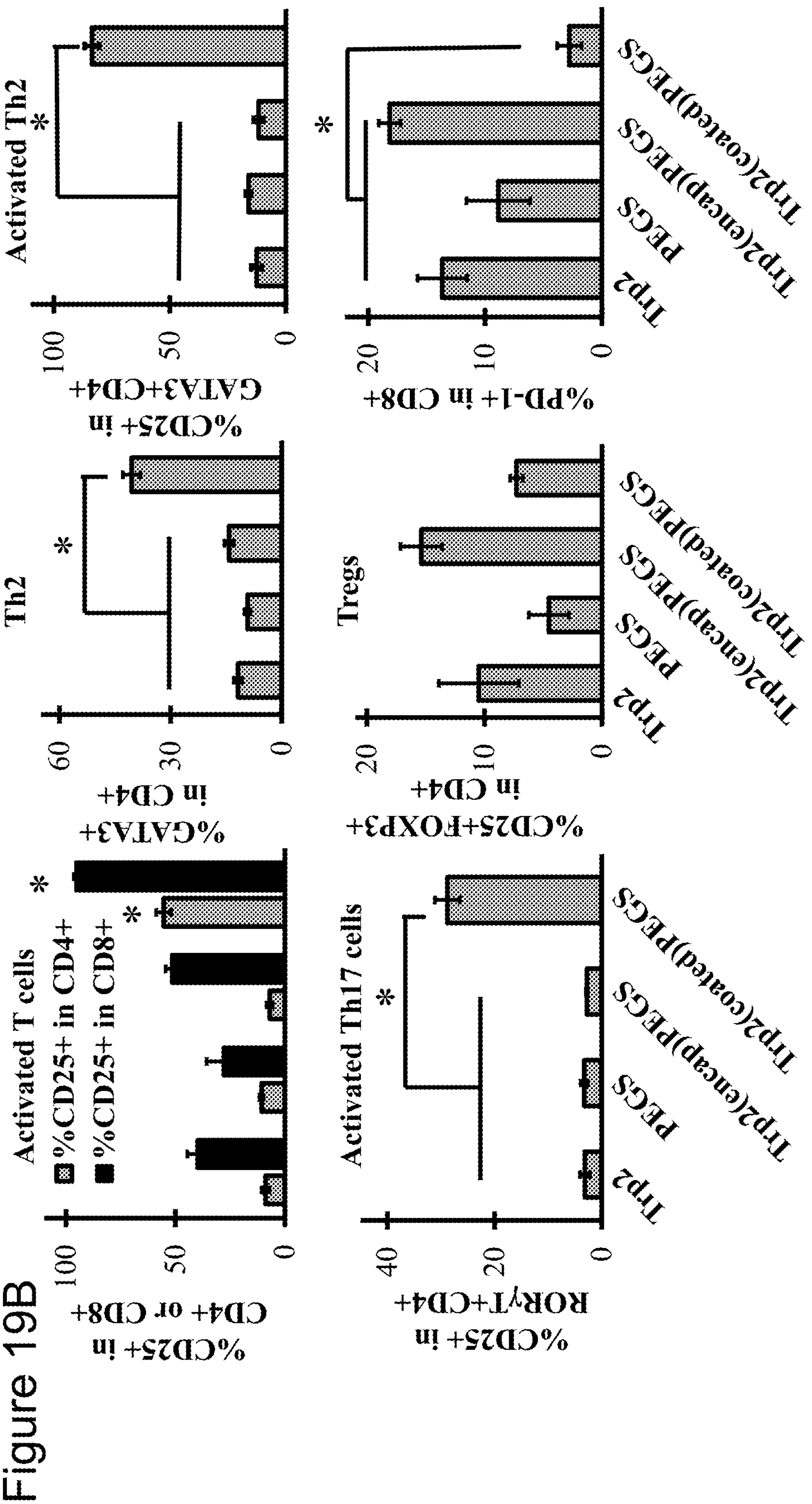
Figure 19C:
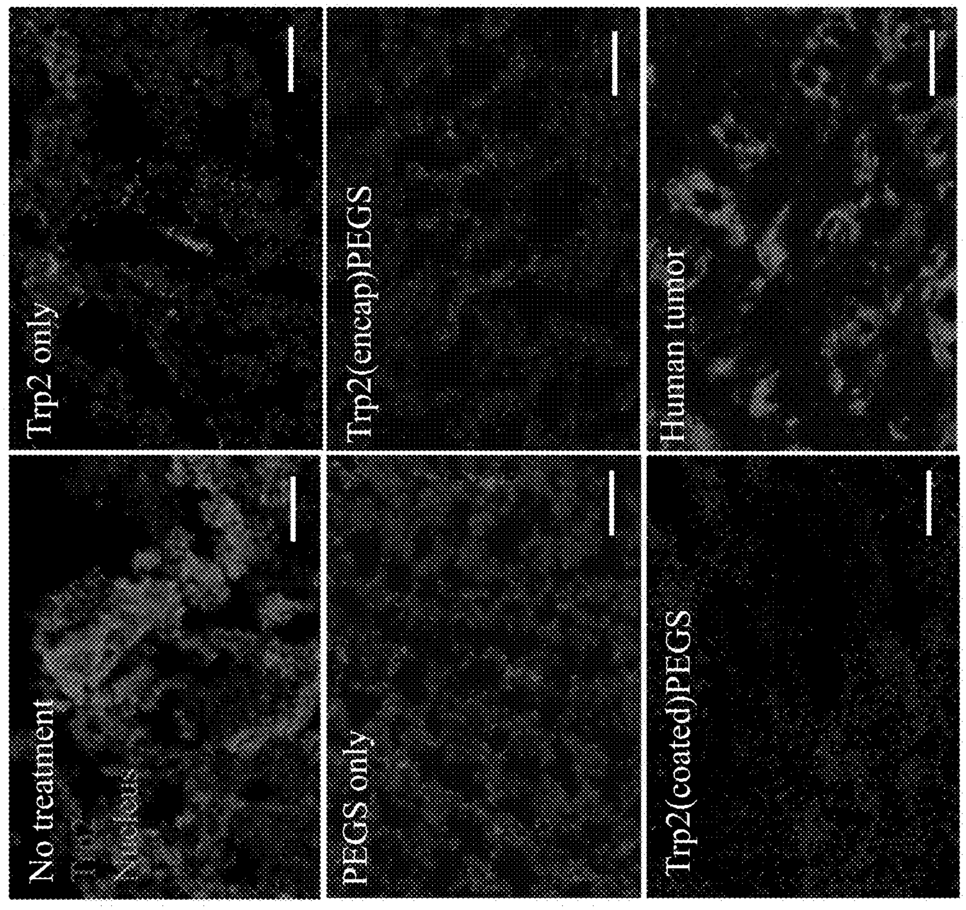
Figure 19D:
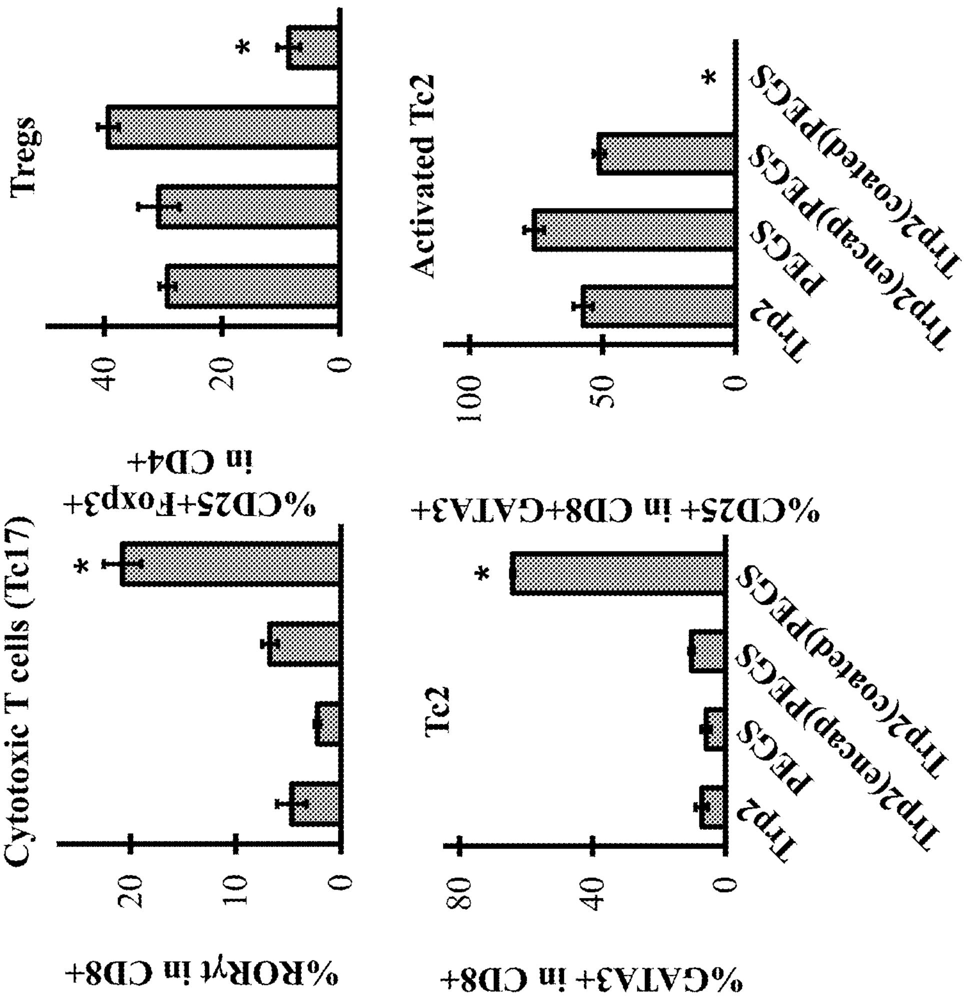
Figure 19D:
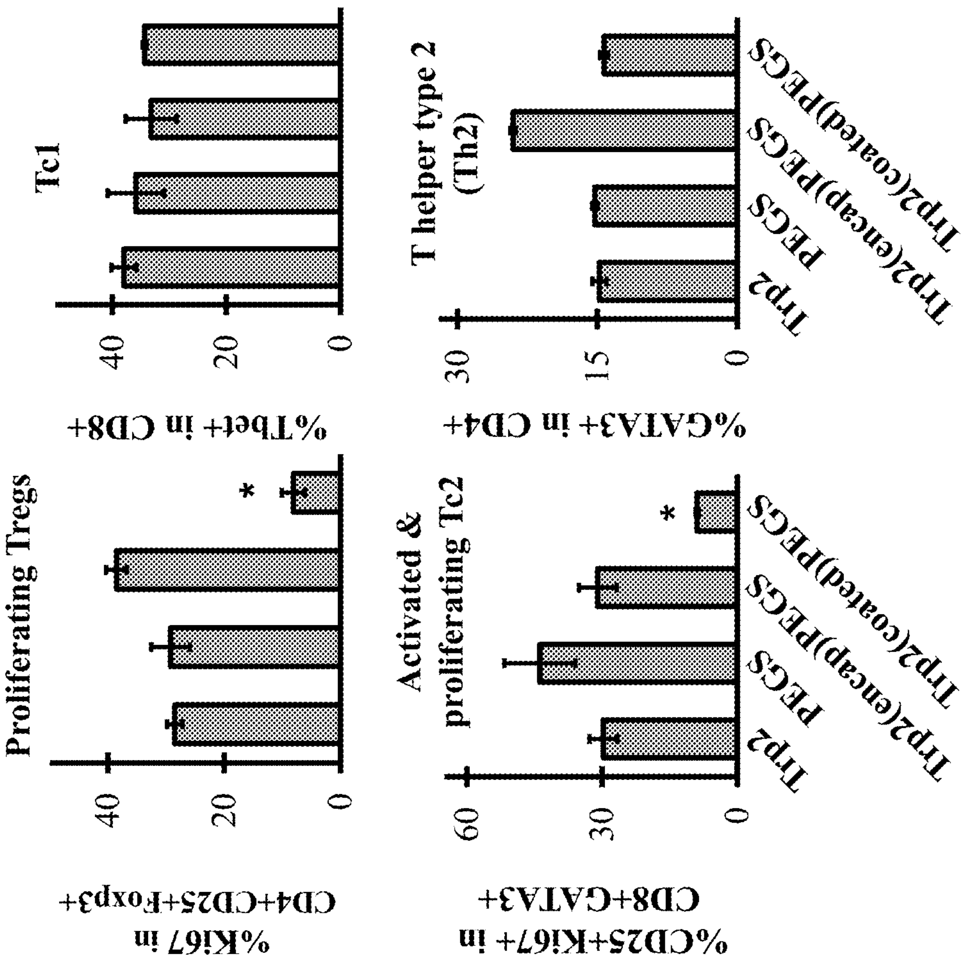
Figure 19D:
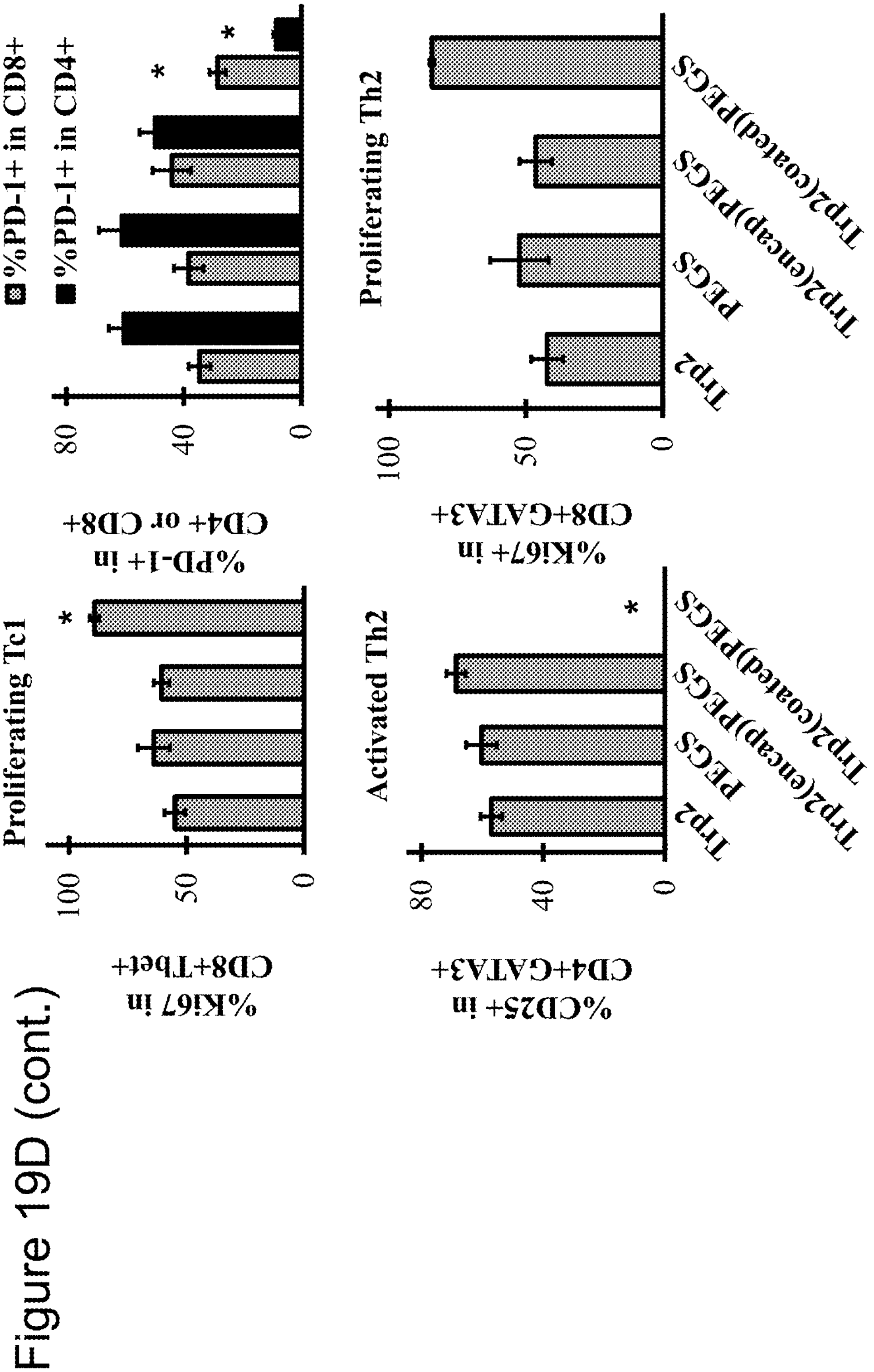

The herein disclosed studies demonstrate, for the first time, a technique that can control metabolism of immune cells in the presence of glycolysis and glutaminase inhibitors, which is highly beneficial in generating robust immune responses against melanoma or other types of cancers. The general mechanism by which immunometabolism modulating particles function is illustrated in FIG. 2 and FIG. 17.

The present invention stems, in part, from the following characteristics of the biomaterial system:

(1) Ability to rescue DCs from glycolysis inhibition in the presence of potent and specific glycolytic inhibitor, and generate vaccine responses.—This aspect is innovative because, for the first time, a metabolite delivery strategy is described and tested (data disclosed below), which has the capability of rescuing DCs from metabolic exhaustion. Moreover, this technology is able to deliver critical metabolite, F16BP, in the glycolysis pathway to DCs, thereby maintaining the activation state of DCs, and potentially inducing adaptive T cell responses (data disclosed below).

(2) Ability to rescue DCs from glutaminase inhibition in the presence of potent glutaminase inhibitor and generate vaccine responses—This aspect is innovative because, for the first time, sustained intracellular delivery of succinate is achieved, which is able to maintain activation of DCs in vitro and in vivo (data disclosed below). This project is also highly innovative because microparticles generated with succinate as the backbone are able to activate DCs and induce vaccine responses without the delivery of adjuvant.

PFK15 Prevents T Cell and Dendritic Cell Activation In Vitro

Figure 3:
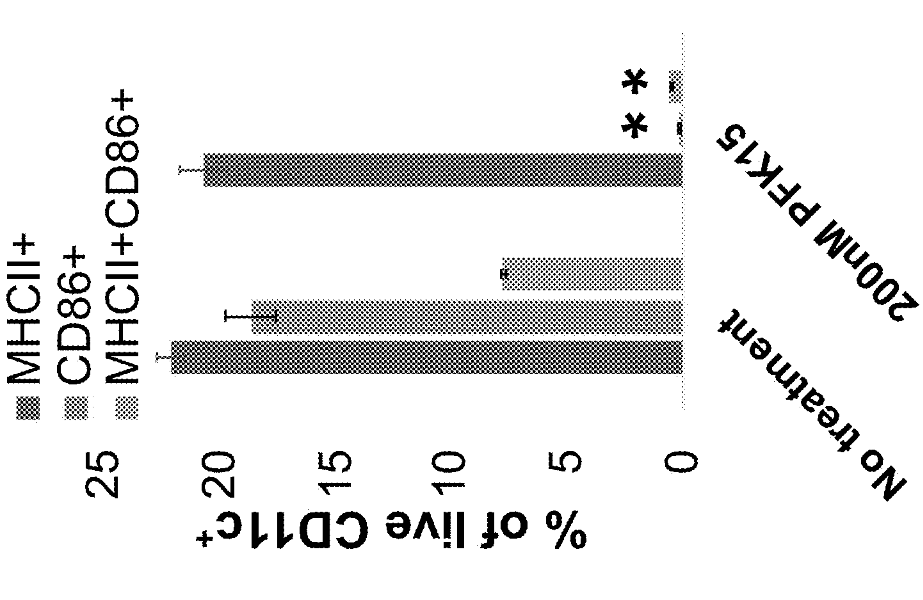
FIG. 3 depicts representative results demonstrating that glycolysis inhibition via PFK15 prevents dendritic cell activation. Incubation of bone marrow derived dendritic cells with 200 nM PFK15 significantly reduces activation in DCs as observed by lowering of CD86+ and MHCII+CD86+ populations in CD11c+ DCs. N=3-4±std. error; *=p<0.05

In order to test the effect of PFKFB3 inhibition on DC and T cell activation, PFK15 was employed. Specifically, DCs were isolated from bone marrow of C57BL/6j mice using GM-CSF, and incubated with different concentrations of PFK15 (50, 100, 200, 400, 800, 1600 nM) for 24 hours. These cells were then stained for MHCII, CD86 and CD 11c to determine activation profile. It was observed that at 200 nM and higher concentrations of PFK15 prevented the activation of DCs (FIG. 3—200 nM shown as example).

PFK15 Prevents Melanoma (YUMM1.1 and B16F10) Proliferation In Vitro

Figure 4:
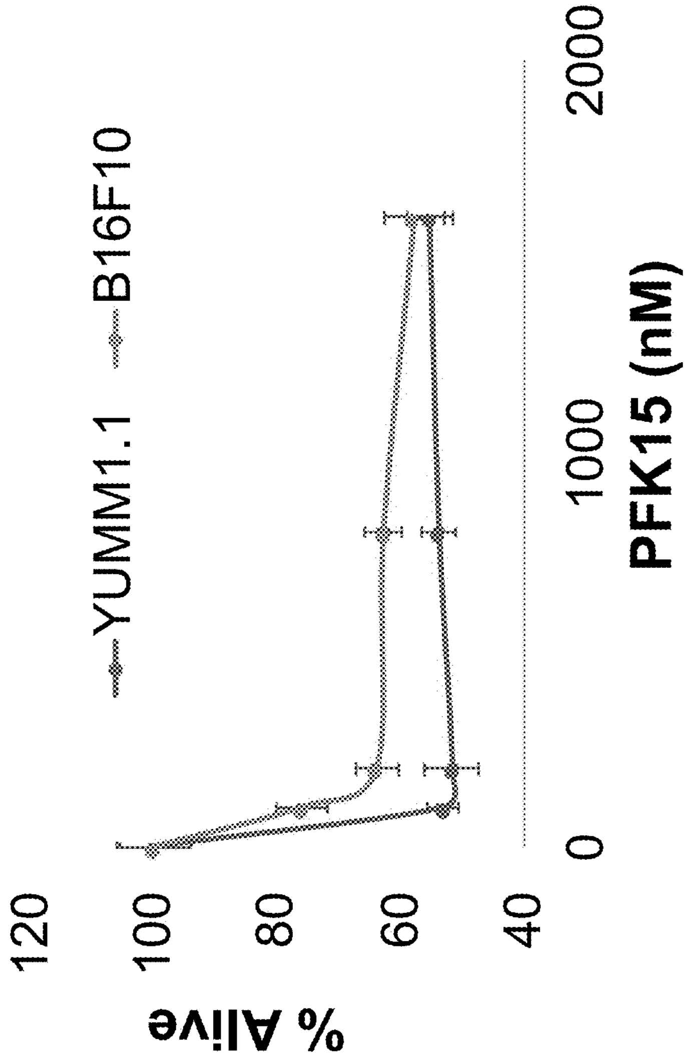
FIG. 4 depicts representative results demonstrating that PFK15, a glycolysis inhibitor, is effective in killing melanoma cells. PFK15 is able to kill both YUMM1.1 and B16F10 cell in vitro.

In order to determine if PFK15 prevents melanoma cell growth in vitro, two different mouse melanoma cells were utilized, namely YUMM1.1 (BrafV600E/wt, Pten−/− Cdkn2−/−MHClHi) and B16F10. Specifically, YUMM1.1 and B16F10 cells were cultured with different concentrations of PFK15, and the percentage cell viability was determined using MTT assay. It was observed that IC50 for PFK15 to prevent proliferation of YUMM1.1 cells was 100 nM, and that for B16F10 was 1600 nM. These data demonstrated that YUMM1.1 cells are more sensitive to glycolysis than B16F10 cells (FIG. 4).

Figure 5A:
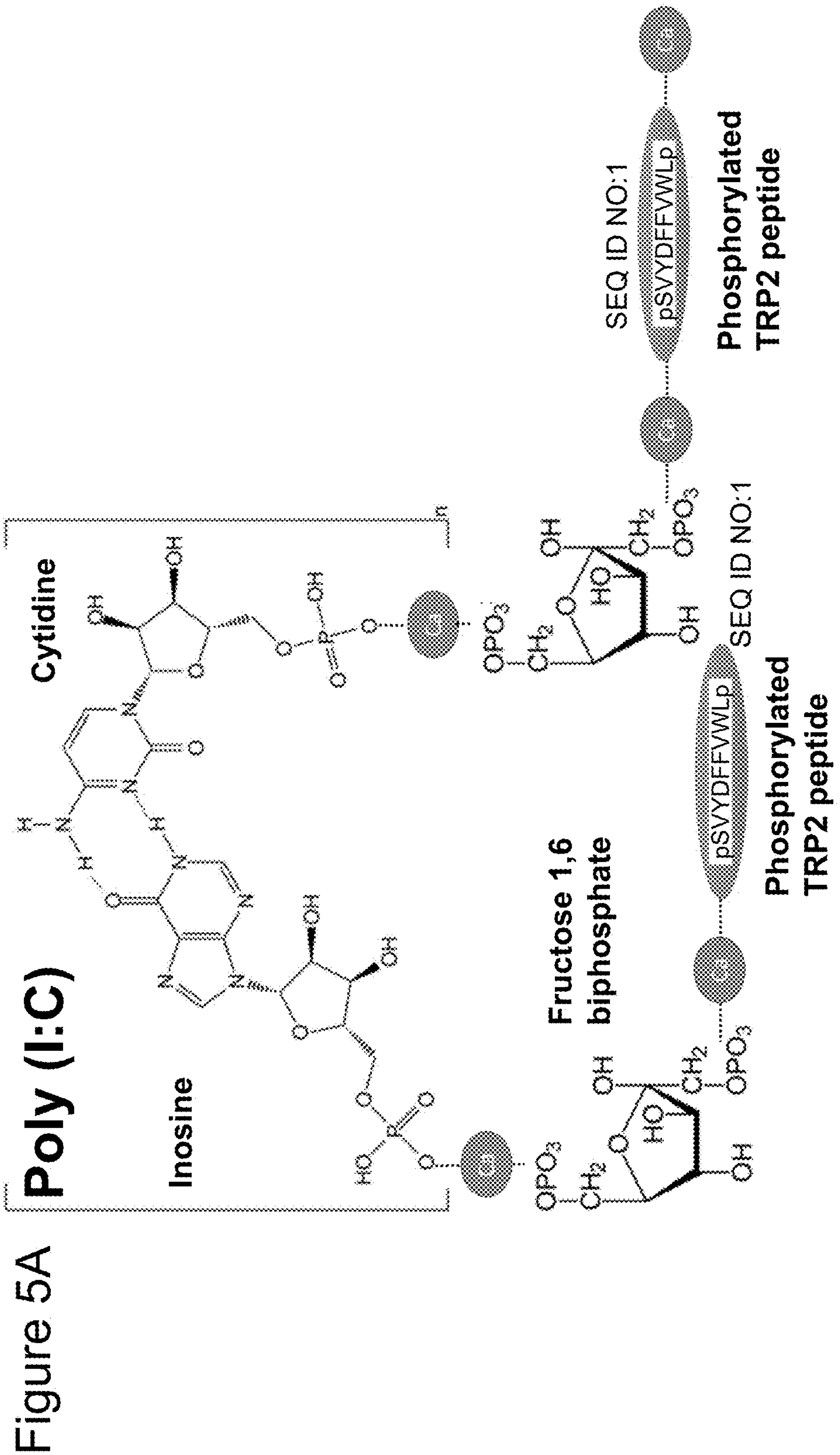
FIG. 5A through FIG. 5E, depicts F16BP particles characterization.
Figure 5C:
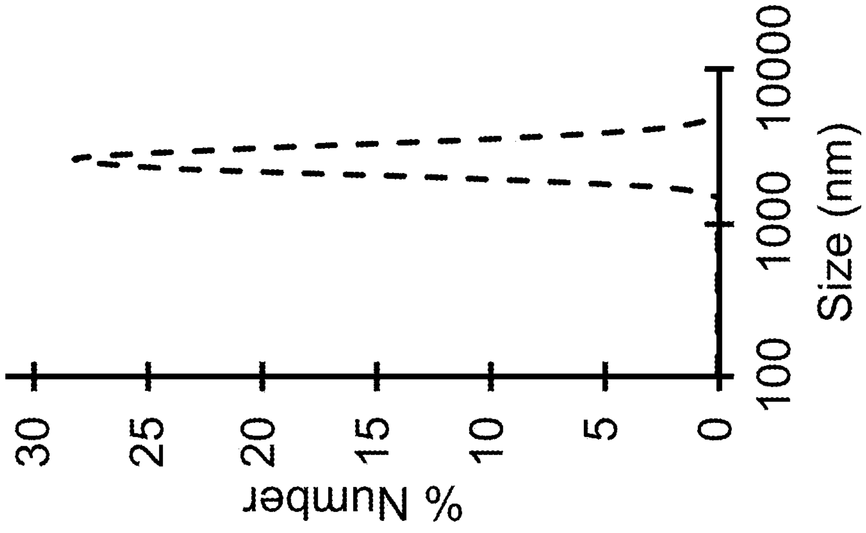
Figure 5B:
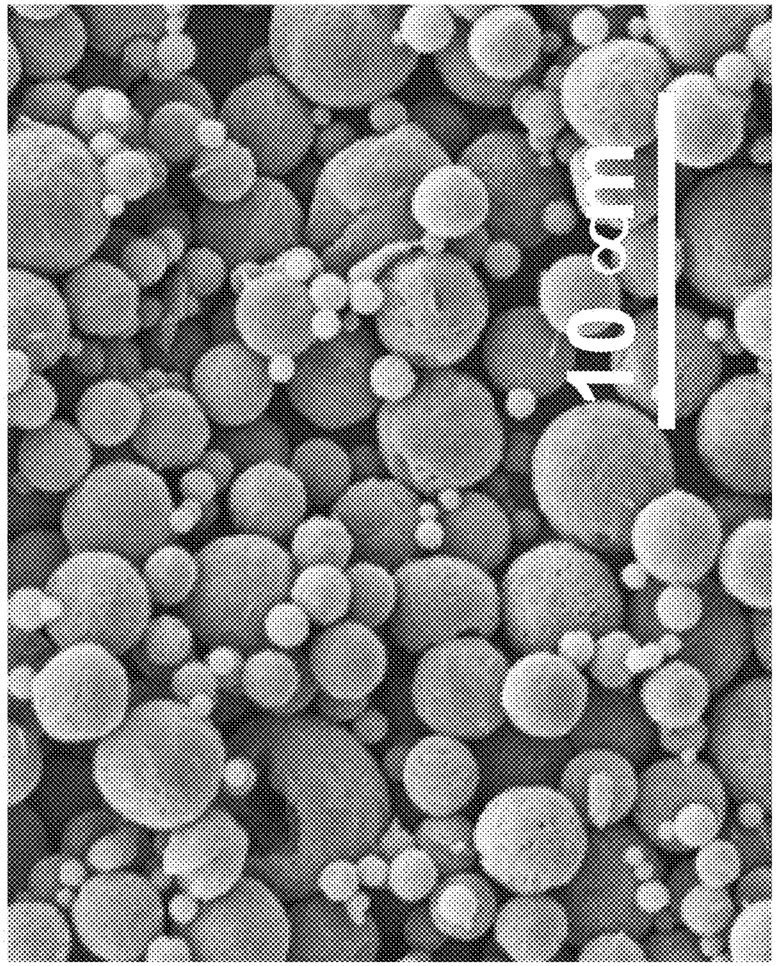
Figure 5D:
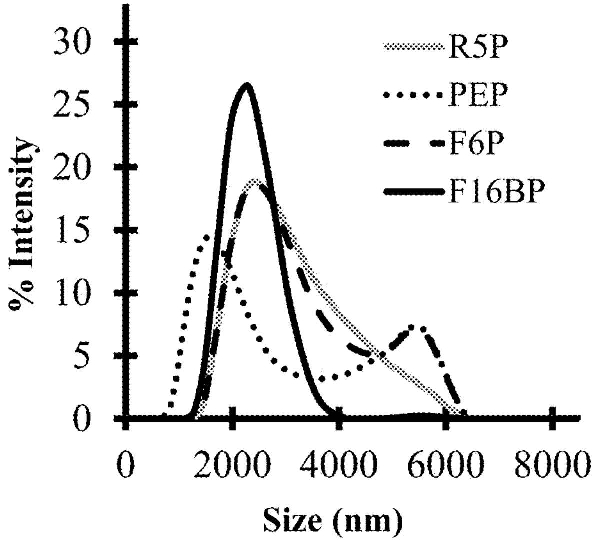
Figure 5E:
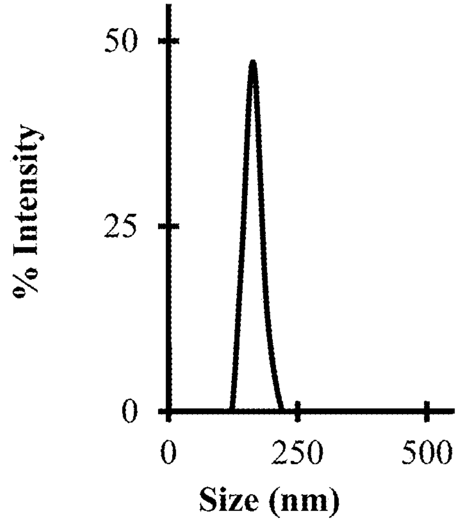

F16BP can be Formulated in Particles Incorporating Poly (I:C) as Adjuvants and TRP2 Peptide as the Antigen In order to encourage phagocytosis and ensure that the same cell gets both the antigen and the adjuvant, it is beneficial if the formulation is in a particle format, as this ensures delivery of peptide antigen and the adjuvant to the same cell. Moreover, this strategy also provides a way to indirectly target phagocytic cells, including DCs that can then drain to the lymph nodes and affect the tumor immune response. Therefore, particles were synthesized using calcium-phosphate ionic bond chemistry. Schematic of the polymer structure formed between the phosphate groups of poly(I:C). F16BP and TRP2 peptide (SVYDFFVWL—phospho-tyrosine on both ends) and calcium (FIG. 5A) is shown. The formation of the particles was confirmed using scanning electron microscopy (FIG. 5B). Also, it was confirmed that the particles were phagocytosable using dynamic light scattering analyses (average size=3 μm) (FIG. 5C through FIG. 5F).

F16BP Particles Rescues Glycolysis Even in the Presence of PFK15 in DCs

Figure 6B:
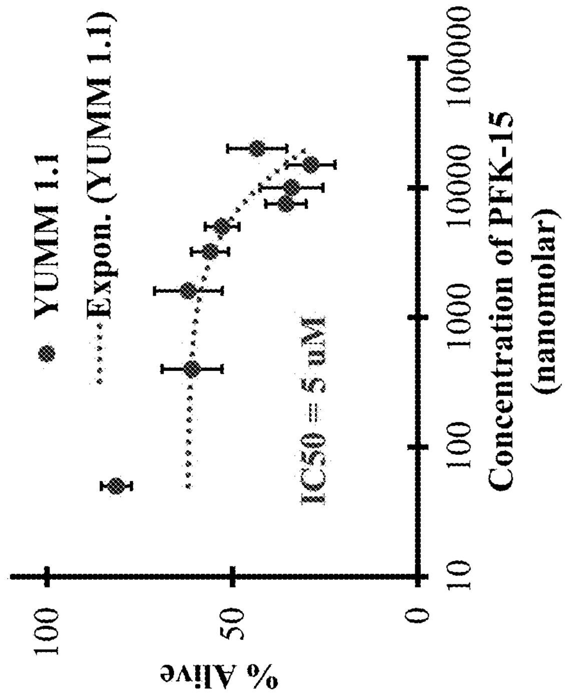
FIG. 6A through FIG. 6D, depicts representative results demonstrating that DC activation markers (MHCII and MHCII+CD86+) were downregulated upon addition of PFK-15 inhibitor and that F16BP particles rescue extracellular acidification rate (ECAR) of DCs in the presence of PFK15 glycolysis inhibitor PFK-15.
Figure 6A:
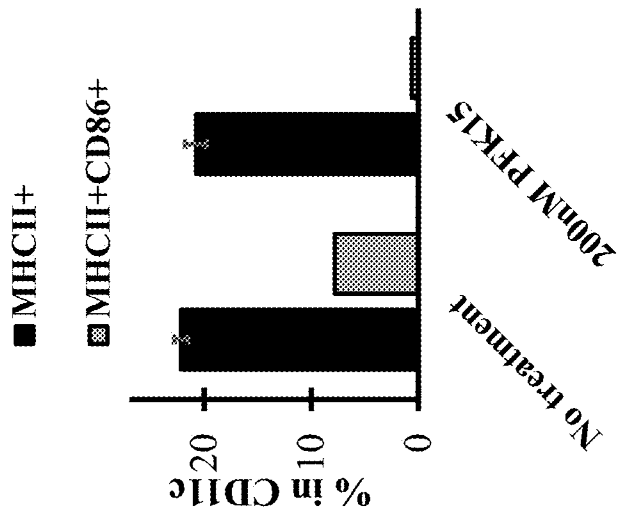
Figure 6D:
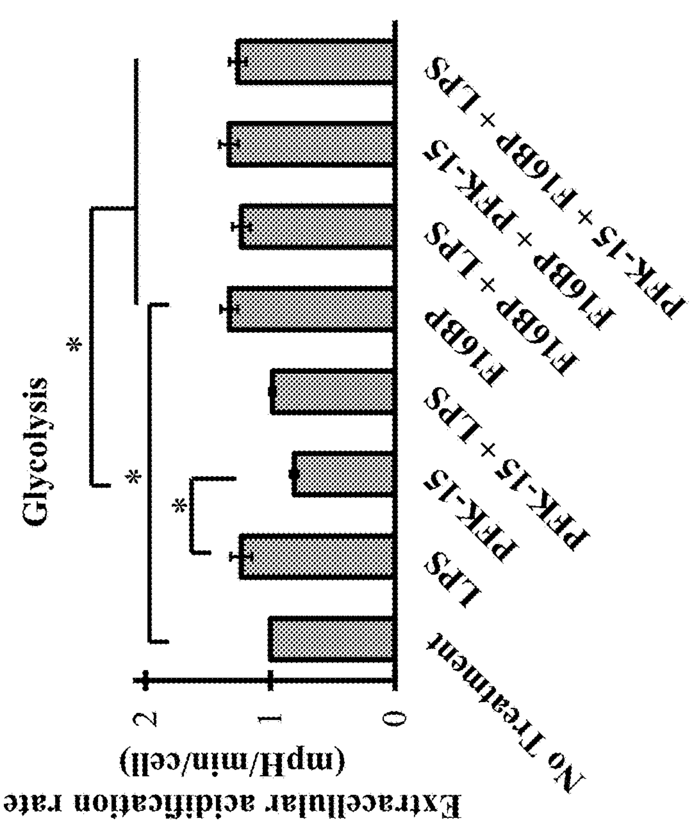
Figure 6C:
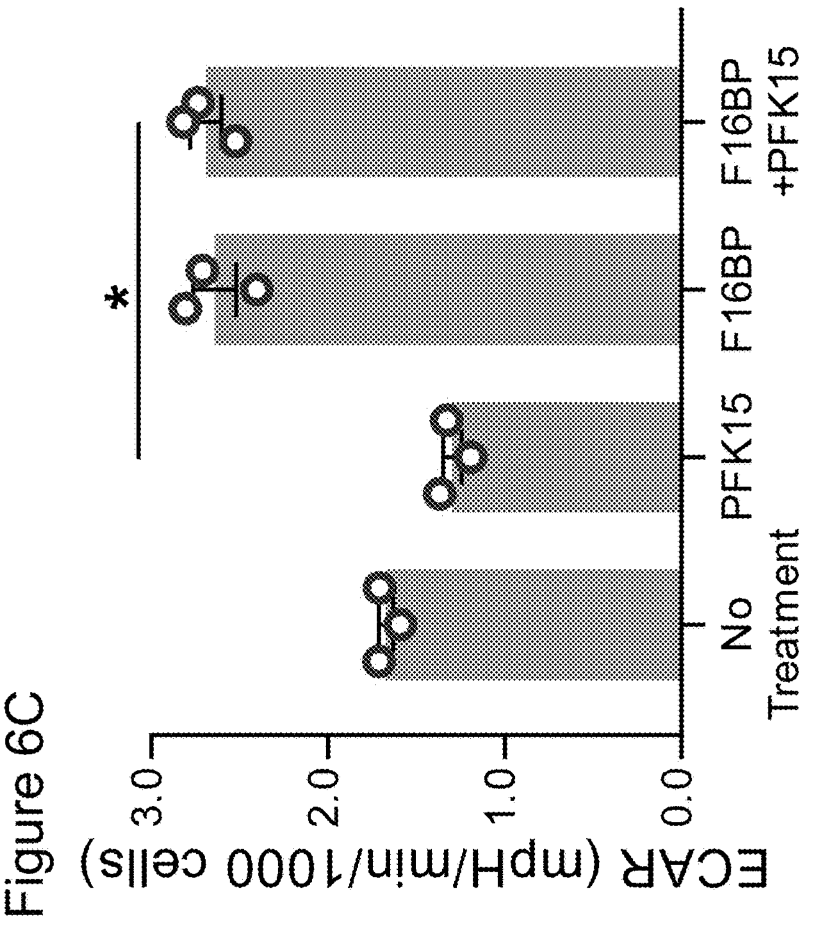

In order to test if F16BP particles can rescue DCs from exhaustion when cultured in the presence of PFK15, ECAR using Seahorse assays was utilized. Specifically, DCs were cultured with either PFK 15 (200 nM), F16BP (0.1 mg/mL) or PFK15+F16BP with or without LPS and ECAR measurements were obtained. It was observed that PFK15 when added to cells in the presence of LPS was able to maintain ECAR values similar to no treatment (FIG. 6). Notably, PFK15 without LPS brought the ECAR values even lower than the no treatment control (FIG. 6C and FIG. 6D). Importantly, when F16BP particles were added in the presence of PFK15, the ECAR values were significantly higher than PFK15 alone control. These data strongly demonstrated that F16BP particles can rescue the glycolysis in DCs in the presence of PFK15.

Figure 7A:
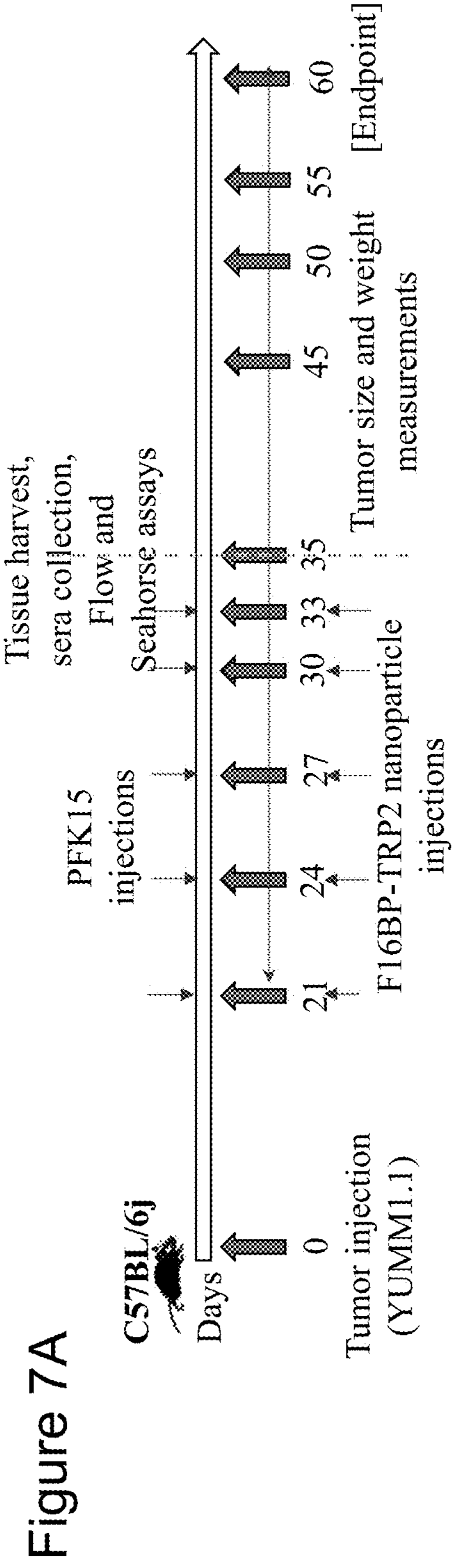
FIG. 7A through FIG. 7D, depicts representative results demonstrating that administration of F16BP particles with PFK15 significantly decreased tumor burden and delayed tumor growth in mice.
Figure 7B:
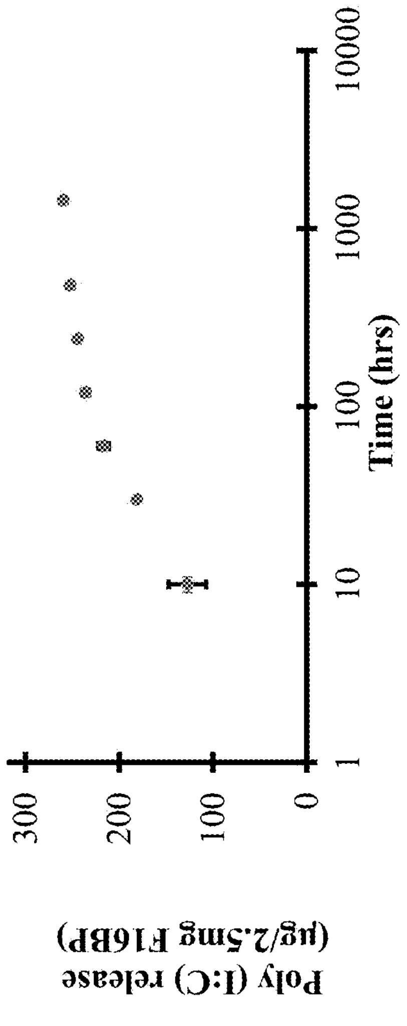
Figure 7C:
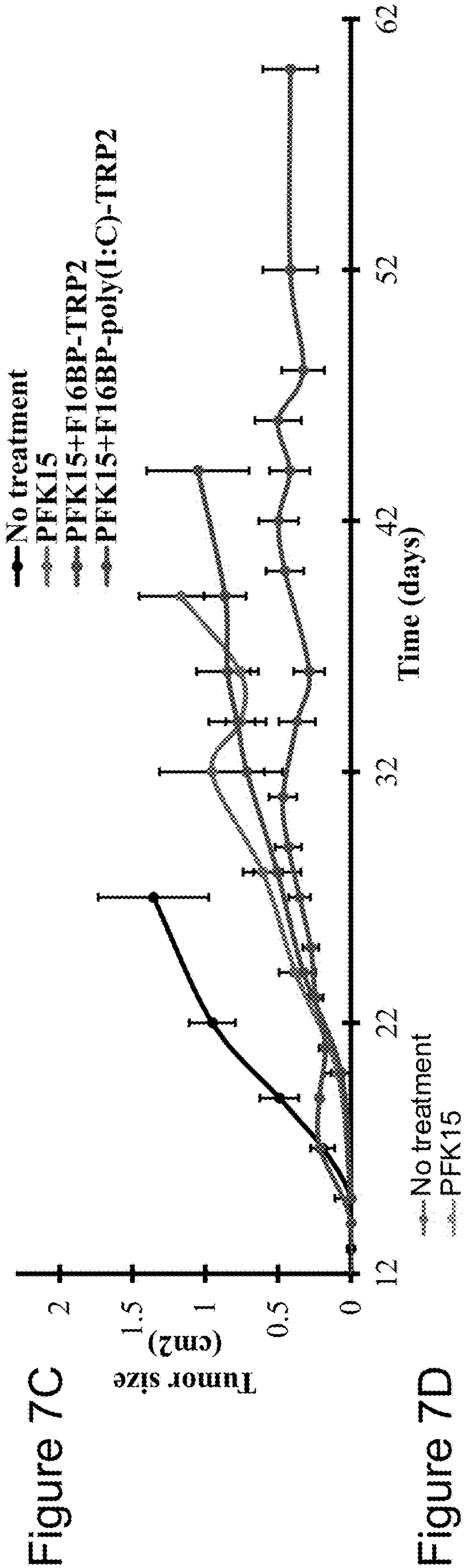
Figure 7D:
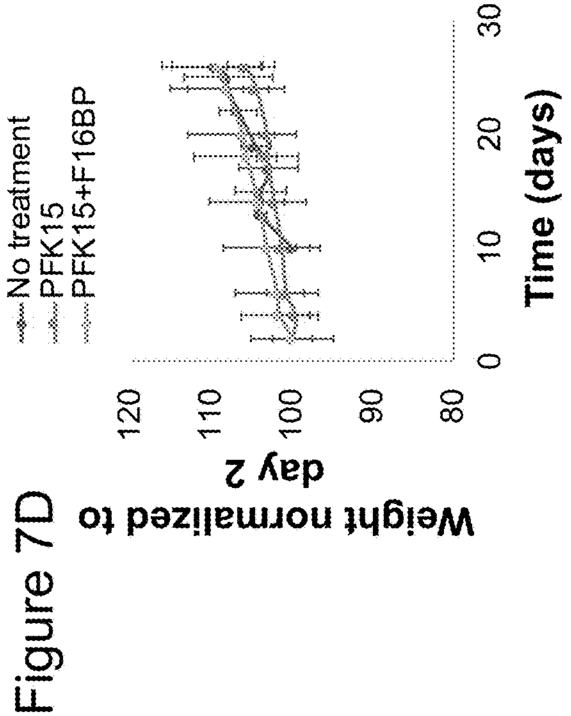

Glycolysis Modulation (PFK15+F16BP Particles-Based TRP2 Peptide Vaccines) Modulates the Tumor Burden in Mice In order to determine if the injection of F16BP particles in vivo can lead to longer survival in mice, study design shown in FIG. 7A and FIG. 7B was followed. Notably, PFK15 by itself improved the survival of mice by 15 days, and addition of F16BP vaccines+PFK15 led to significantly lower tumor growth (FIG. 7C). It was observed that the subcutaneous injections of F16BP particles did not lead to overall toxicity as observed by the weight changes in mice (FIG. 7D).

Figure 8A:
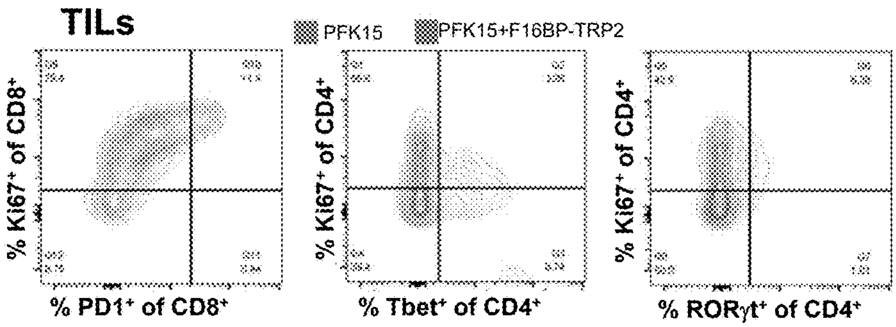
FIG. 8A and FIG. 8B, depicts representative results demonstrating that PFK15+F16BP particle treatment increases pro-inflammatory Th1 and Th17 cells, and decreases proliferation of Tregs and potentially exhausted CD8 T cells.
Figure 8B:
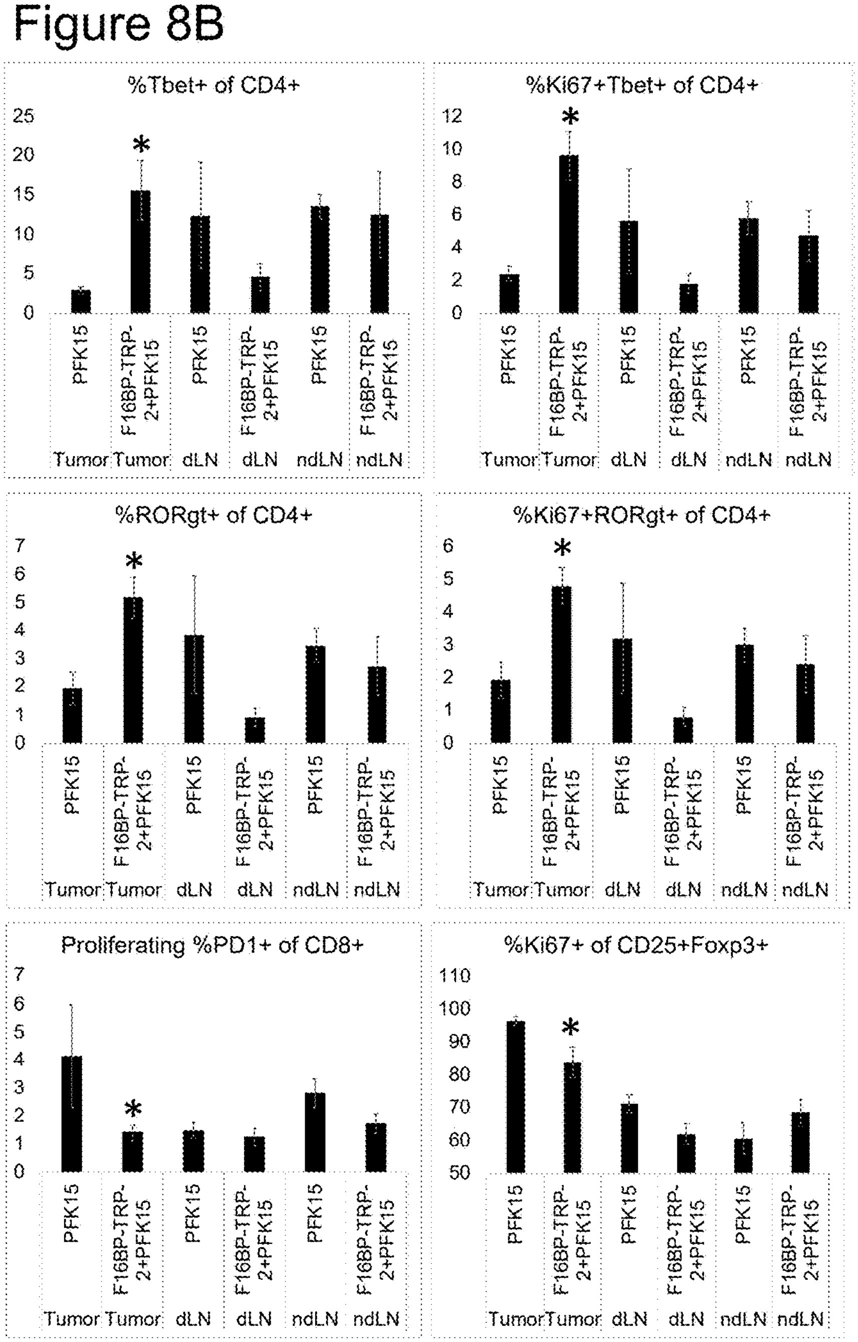
Figure 9:
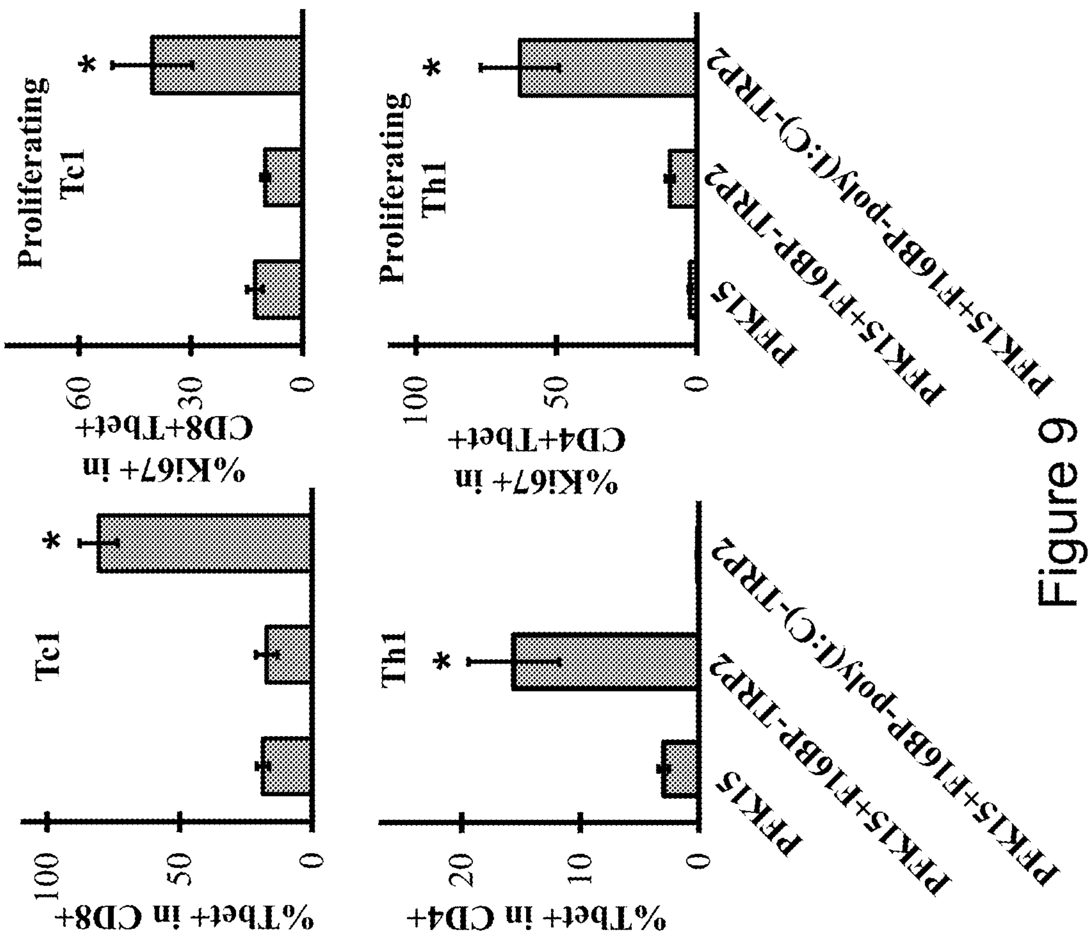
FIG. 9 depicts representative results demonstrating the modulation of tumor infiltrating lymphocytes (TILs) in mice treated with different treatment groups in vivo (n=5).
Figure 9:
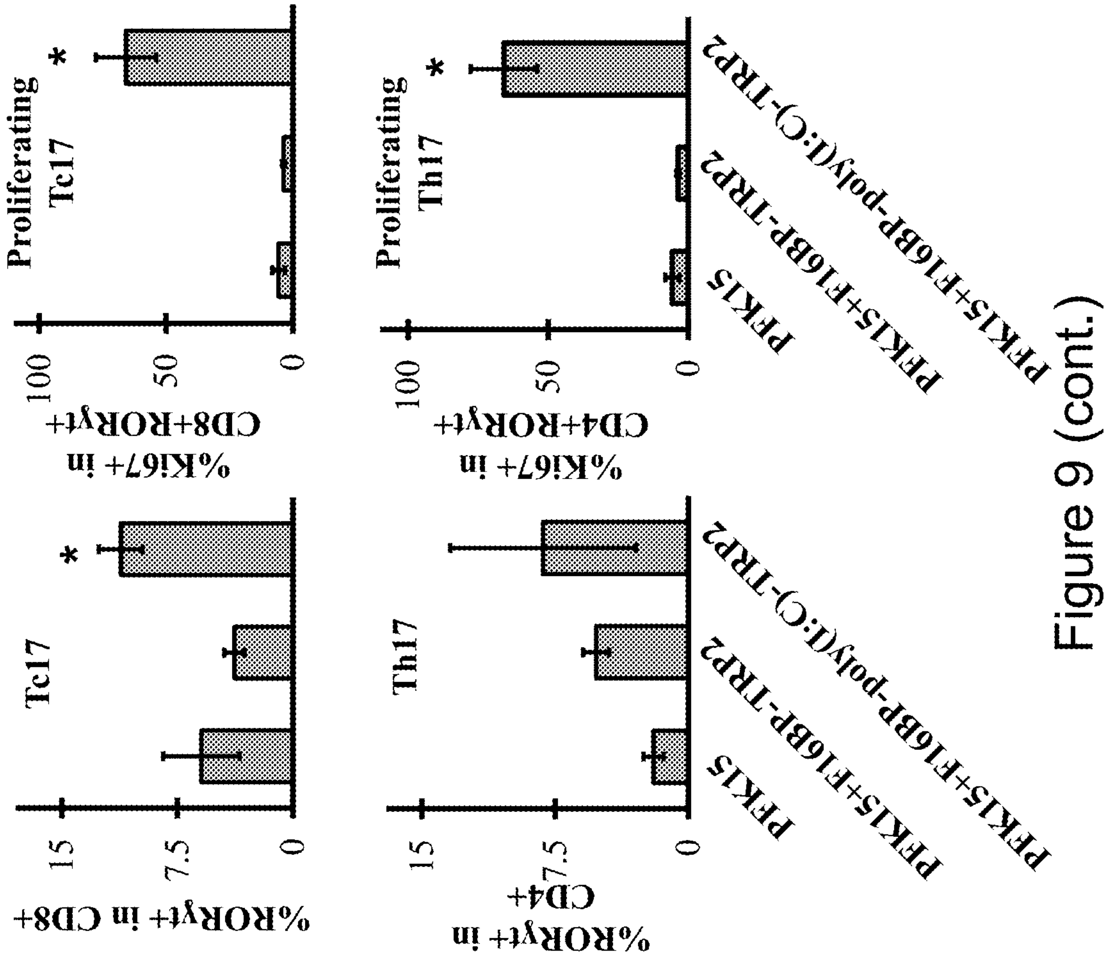
Figure 11:
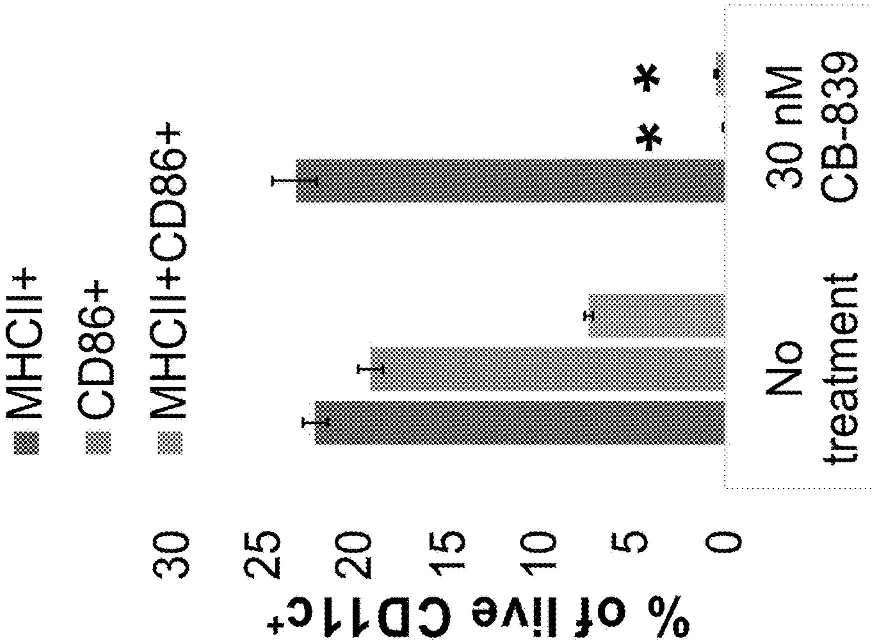
FIG. 11 depicts representative results demonstrating that glutaminase inhibition via CB-839 prevents dendritic cell activation. Incubation of bone marrow derived dendritic cells with 30 nM CB-839, significantly reduces activation in DCs as (lowering of CD86+ and MHCII+CD86+). N=6±std. error; *=p<0.05.

F16BP Particles-Based Vaccines Induce Robust Immune Responses in YUMM1.1 Tumor Model in Mice In order to test the efficacy of F16BP particles-based vaccines to reduce tumor growth in mice, C57BL/6j mice were utilized. Specifically, tumors were induced by injecting $0.75\times10^{6}$ cells in the back of the mice. From day 18 onwards, mice were injected with the F16BP based vaccines injected subcutaneously (0.5 mg/mouse) every 3 days (total 3 treatments—days 21, 24, 27) with PFK15 (5 mg/kg) injected every other day intraperitoneally (FIG. 7A—same study design as survival but mice euthanized day 28 for T cell analyses). Controls included PFK15 injections every alternate day, or no treatment. Mice were then sacrificed on day 26 and the tumors, draining lymph nodes, and non-draining contralateral lymph nodes were harvested. The cells were then stained for CD4, CD8, CD25, PD-1, Ki67, Foxp3, RORγt, Tbet, to identify frequency of Th1 (CD4+Tbet+), Th17(CD4+RORγt+), Tc1 (CD8+Tbet+), Treg (CD4+CD25+Foxp3+) and Tc17 (CD8+RORγt+) populations, and proliferation (Ki67). It was observed that within the tumor infiltrating lymphocytes (TILs) there was a significantly lower percentage of (CD8+PD1+Ki67+) T cells in F16BP vaccines group (blue—FIG. 8A and FIG. 9) as compared to PFK15 alone (red population), which might suggest higher level of exhaustion in PFK15 alone group, and decreased exhaustion in F16BP vaccine group. Moreover, both Th1 (CD4+Tbet+Ki67+) and Th17 (CD4+RORgt+Ki67+) cells proliferated at higher levels in the F16BP vaccine group as compared to PFK15 alone group (FIG. 8B and FIG. 9). Although, the total percentage of Treg populations within the tumor was much higher in F16BP vaccines as compared to PFK15 alone group, the percentage of proliferating Tregs was significantly lower. These data suggest that potentially the Tregs within the tumor might not be proliferating and might be less suppressive. Similar trend of cell populations was observed in the draining lymph node as the tumor. Notably, in non-draining lymph nodes (considered as systemic response) the two groups (vaccines versus PFK15 alone) were not significantly different from each other, and thus suggesting that F16BP particles act locally near the injection site.

CB-839 Prevent Melanoma (YUMM1.1 and B16F10) Proliferation In Vitro

Figure 10:
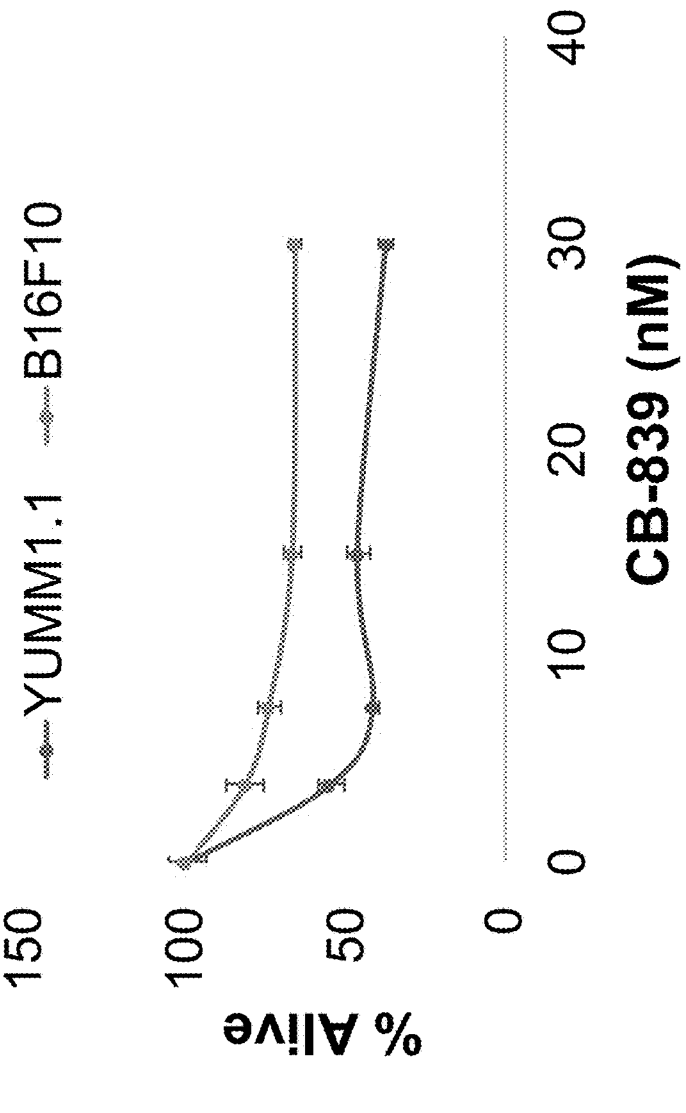
FIG. 10 depicts representative results demonstrating that CB-839, a glutaminase inhibitor, is effective in preventing melanoma cell proliferation. CB-839 is able to prevent proliferation of both YUMM1.1 and B16F10 cell in vitro with 3.75 nM and 30 nM IC50 respectively.

In order to determine if CB-839 prevents melanoma cell growth in vitro, two different mouse melanoma cells were utilized, namely YUMM1.1 and B16F10. Specifically, YUMM1.1 and B16F10 cells were cultured with different concentrations of PFK15, and the percentage cell viability was determined using MTT assay. It was observed that IC50 for PFK15 to prevent proliferation of YUMM1.1 cells was 3.75 nM, and that for B16F10 was 30 nM. These data suggest that YUMM1.1 cells are more sensitive to glycolysis than B16F10 cells (FIG. 10).

CB-839 Prevent DC Activation In Vitro

In order to test the effect of glutaminase inhibition on DC activation, bone marrow DCs were isolated from C57BL/6j mice and cultured with different concentrations of CB-839, a clinically validated molecule (0, 15, 30, 60, 120 nM) for 24 hours. These cells were then stained for MHCII, CD86, and CD11c to determine activation profile. It was observed that at 30 nM and higher concentrations of CB-839 prevented the activation of DCs (FIG. 11—30 nM is shown as a representative example).

Figure 12A:
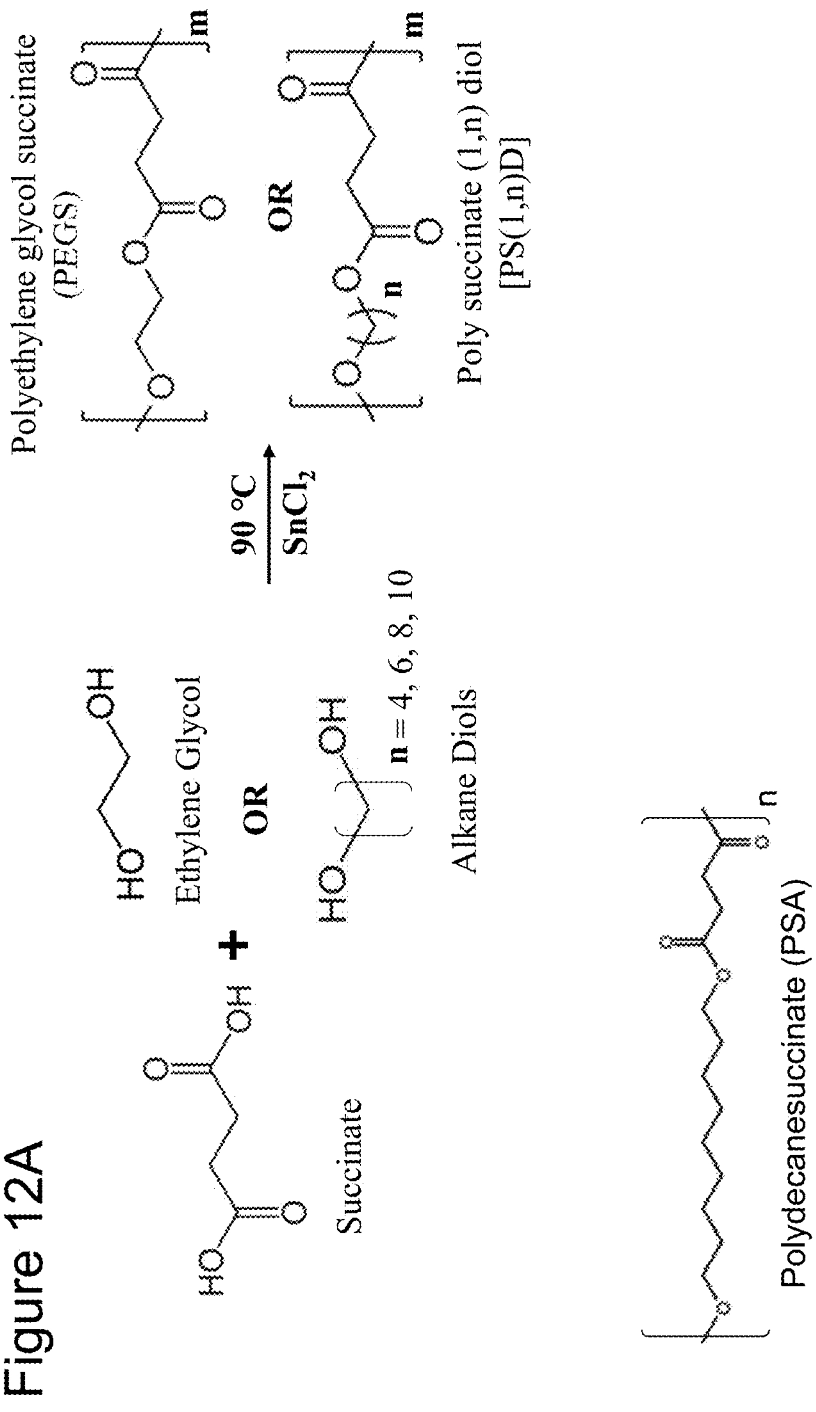
FIG. 12A through FIG. 12F, depicts characterization of succinate based polymeric microparticles.
Figure 12B:
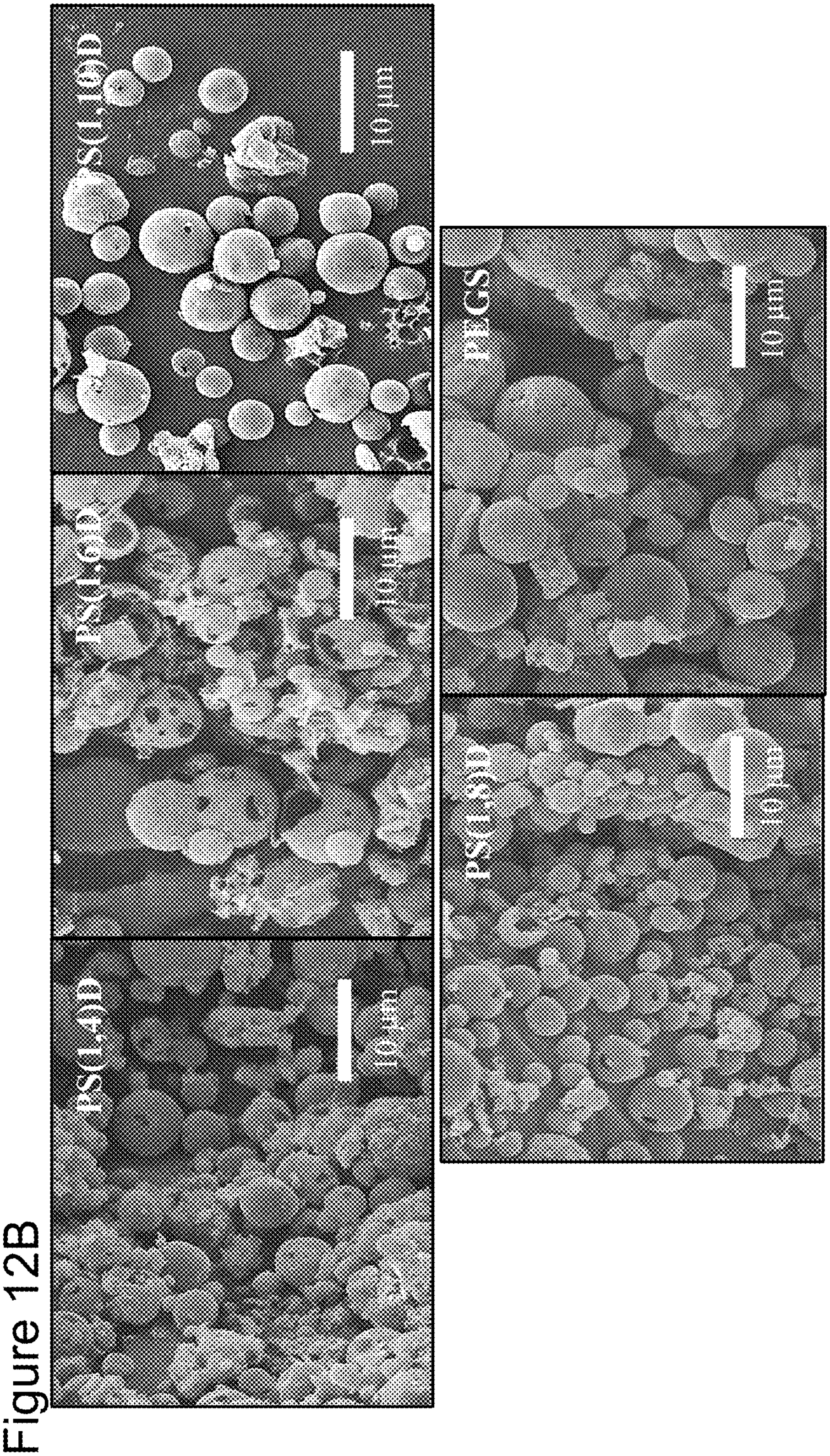
Figure 12C:
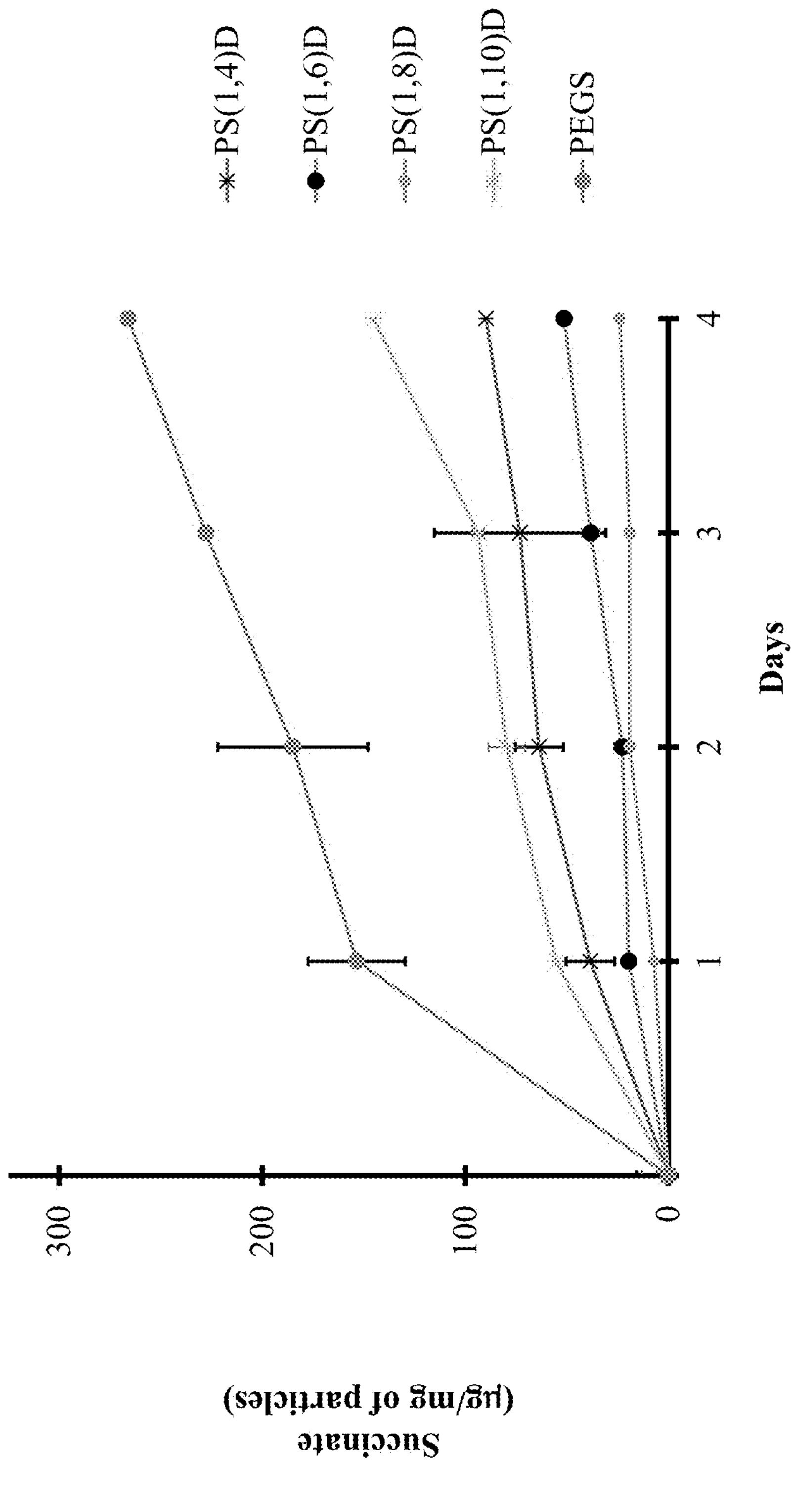
Figure 12D:
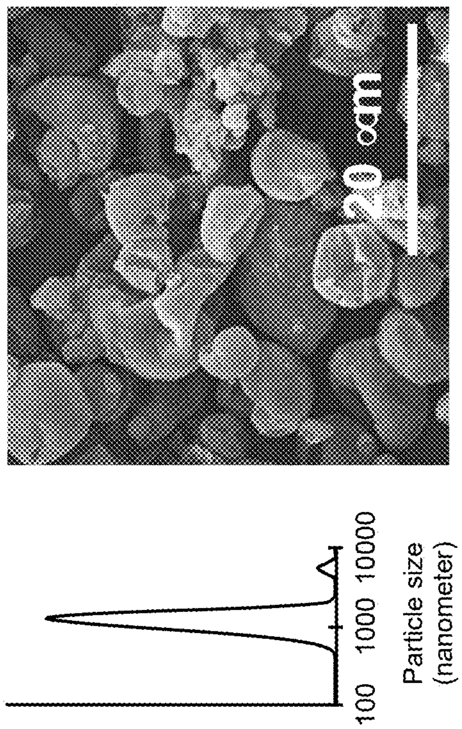
Figure 12E:
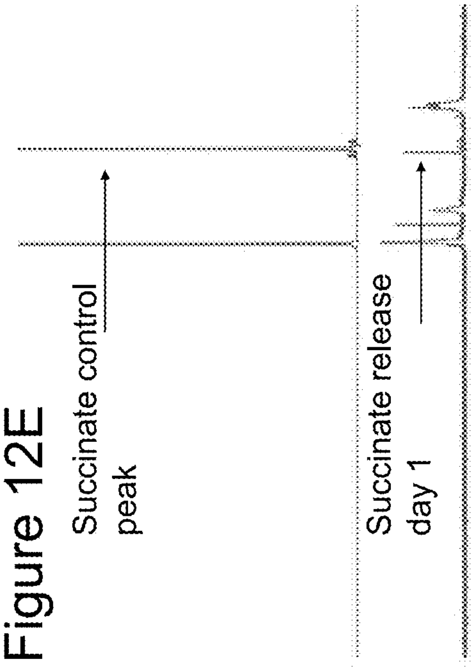

Succinate can be Formulated in Particles Incorporating TRP2 Peptide as the Antigen CB-839 by blocking glutaminase, prevents the mitochondrial oxidation, and thus may directly affect DC activation. Succinate, a key metabolite in the TCA cycle should be able to restart the TCA cycle, but will need to be provided intracellularly in a sustained manner for continuous feed to the TCA cycle. Therefore, succinate-based polymers were synthesized using condensation reactions, and particles from these polymers were generated using water/oil emulsions (FIG. 12A). Specifically, two different polymers were employed poly-succinic acid (PSA) and polyethylene glycol succinate (PEGS), which provide different release kinetics of succinate (PSA slower release as compared to PEGS). These particles were characterized using scanning electron microscopy and dynamic light scattering to determine the size of the particles. It was observed that the particles were approximately 1 μm in diameter (FIG. 12C and FIG. 12D). Moreover, it was also observed using 1H nuclear magnetic resonance that the PEGS particles were able to release succinate for 27 days in vitro in phosphate buffered saline (FIG. 12B and FIG. 12E—day 1 shown for clarity, day 27 smaller peaks).

Figure 12F:
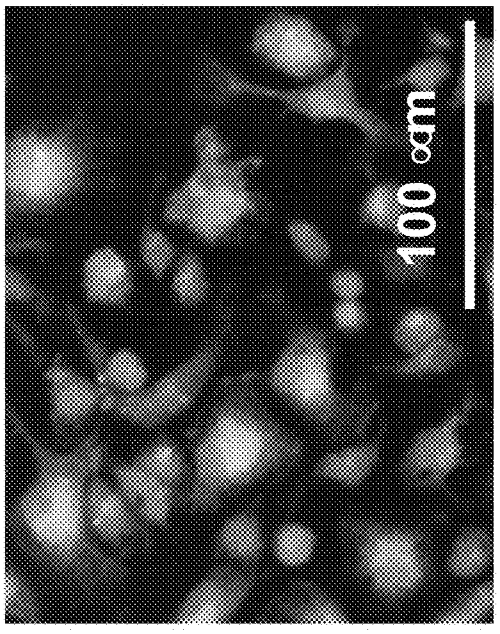

Next, PEGS particles encapsulating rhodamine fluorescent dye was generated to test if DCs are able to phagocytose these particles effectively. Specifically, BMDCs from C57BL/6j mice were incubated with PEGS-rhodamine particles for 2 hours, and then imaged using a fluorescent microscope. It was observed that the DCs were able to phagocytose these particles, and thus these particles will be able to deliver succinate in a sustained fashion intracellularly in DCs (FIG. 12F).

ECAR and OCR is Upregulated when DCs are Treated with PEGS Microparticles Even in the Presence of CB-839

Figure 13B:
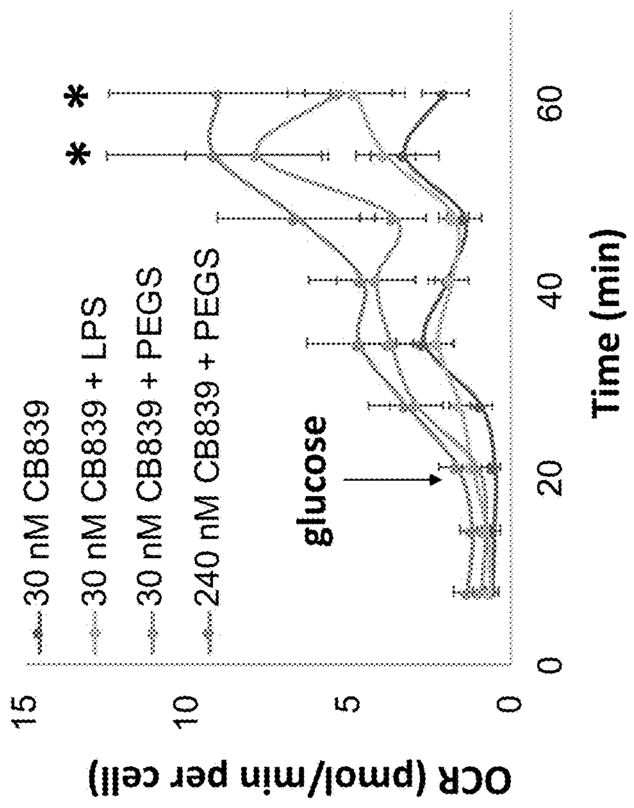
FIG. 13A and FIG. 13B, depicts representative results demonstrating that PEGS particles rescues ECAR and oxygen consumption rate (OCR) of DCs in the presence of glutaminase inhibitor CB-839. DCs cultured with CB-839 do not upregulate glycolysis or mitochondrial respiration even in the presence of LPS as observed by ECAR and OCR values, respectively.
Figure 13A:
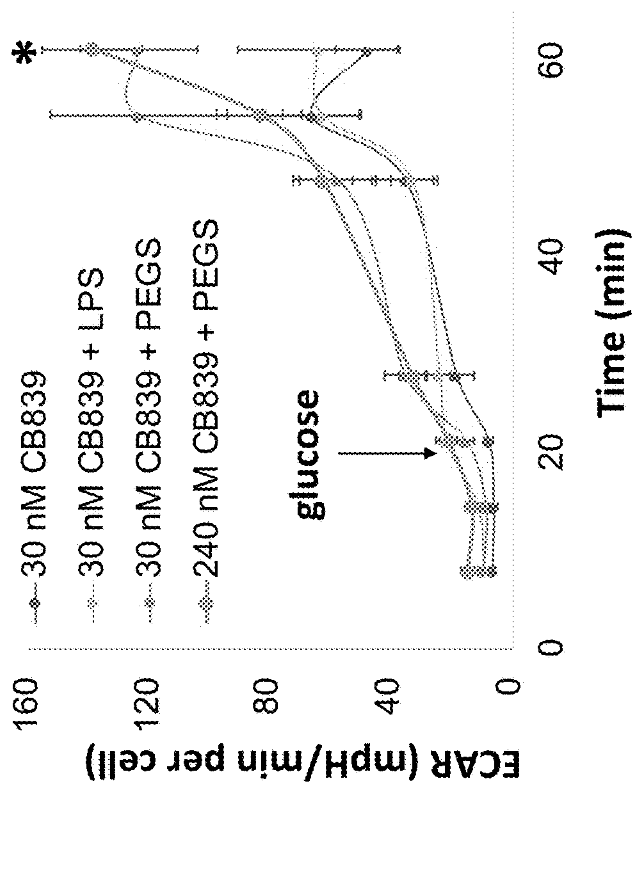

In order to evaluate if PEGS particles are able to modulate the glycolysis of DCs in the presence of CB-839, glycolysis stress test was performed and ECAR values were recorded. Specifically, immature DCs were obtained from C57BL/6j mice and cultured with PEGS (0.1 mg/mL) with or without CB-839 (30 nM or 240 nM) for 16 hours. After 16 hours of incubation, DCs were incubated in glucose free medium and ECAR and OCR values were recorded using Seahorse extracellular flux (XF) analyzer (glucose addition at 20 min). It was observed that 30 nM CB-839 was able to block glycolysis and mitochondrial respiration in DCs. Addition of PEGS particles rescued this inhibition as observed by increase in ECAR and OCR values after 60 minutes of data collection (FIG. 13).

DC Function is Rescued by PEGS Even in the Presence of CB-839

Figure 14:
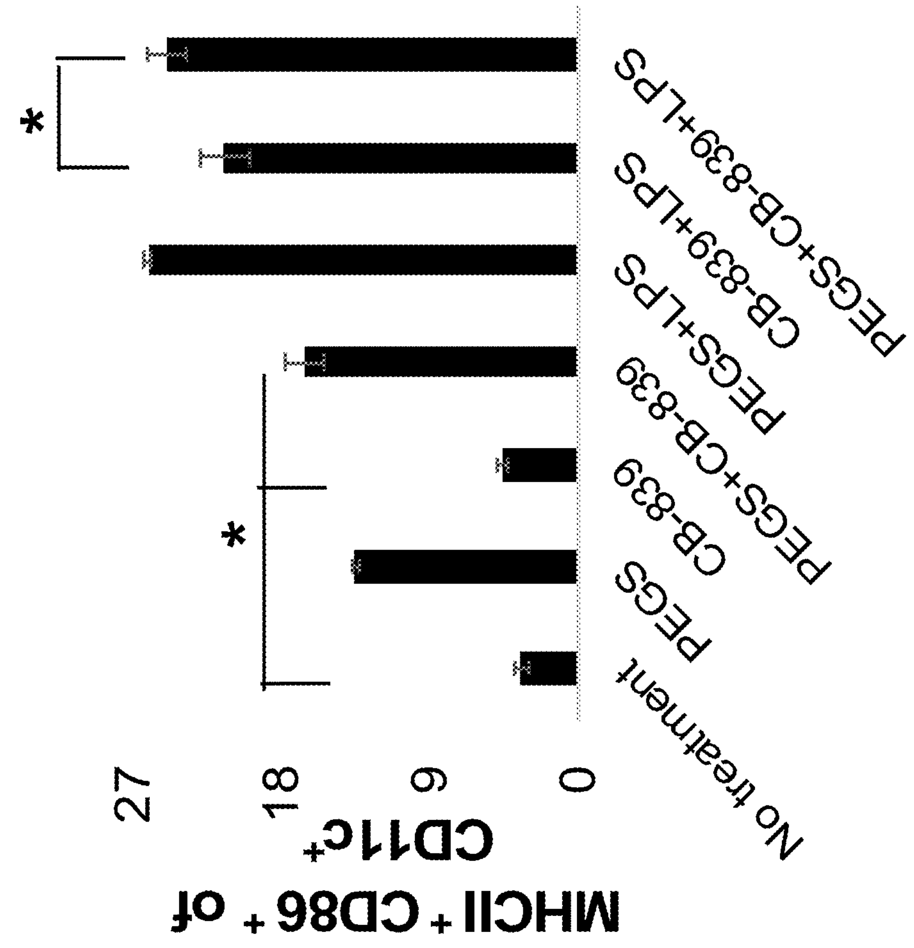
FIG. 14 depicts representative results demonstrating that PEGS particles rescues activation of DCs in the presence of CB-839. PEGS particles induced DC activation without any adjuvant and led to increase in the frequency of MHCI-ICD86 cells when stimulated with LPS even in the presence of CB-839 (30 nM). N=3±std. error; *=p<0.05.

Next, it was evaluated if PEGS particles can rescue the function of DCs in the presence of CB-839 in vitro. Specifically, DCs were cultured in the presence of CB-839 with or without PEGS (0.1 mg/mL) and with or without LPS (0.1 μg/mL) for 24 hours. Cells were then stained for MHC-II, CD86 and CD11c and analyzed using flow cytometry. It was observed that PEGS particles were able to maintain higher frequency of cells with CD86 expression even in the presence of 30 nM CB-839 with or without LPS (FIG. 14). This data clearly indicates that metabolites like succinate are required for rescue from metabolic exhaustion, and LPS alone may not be sufficient.

PEGS Particles-Based TRP2 Peptide Vaccines Induce Robust Immune Responses in B16F10 Tumor Models in Mice Even in the Presence of CB-839 and in the Absence of Adjuvant In order to test if PEGS without any adjuvants can induce vaccines responses in vivo in mice, B16F10 tumors were induced subcutaneously in C57BL/6j mice by injected $0.75\times10^6$ cells/mouse in the back. Starting on day 8, mice were injected with soluble TRP2, or PSA particles encapsulating TRP2 particles, or PEGS encapsulating TRP2 particles (0.1 mg) subcutaneously, twice a week for 3 weeks. Moreover, CB-839 (10 mg/kg) was injected intraperitoneally every other day for 3 weeks. Weight of the mice and tumor size was measured every other day. In order to analyze the infiltration of T cells in the tumor one cohort of mice (n=5 per group) were sacrificed on day 16, and tumor, draining inguinal lymph node, and non-draining contralateral inguinal lymph nodes were isolated. Cells were isolated from these organs and stained for CD4, CD8, CD25, Tbet, GATA3, RORγt, Foxp3, Ki67 to identify frequency of Th1 (CD4+Tbet+), Th17(CD4+RORγt+), Tc1 (CD8+Tbet+), Treg (CD4+CD25+Foxp3+) and Tc17 (CD8+RORγt+) populations, and proliferation (Ki67+) in these cells.

Figures 15A, 15B, 15C:
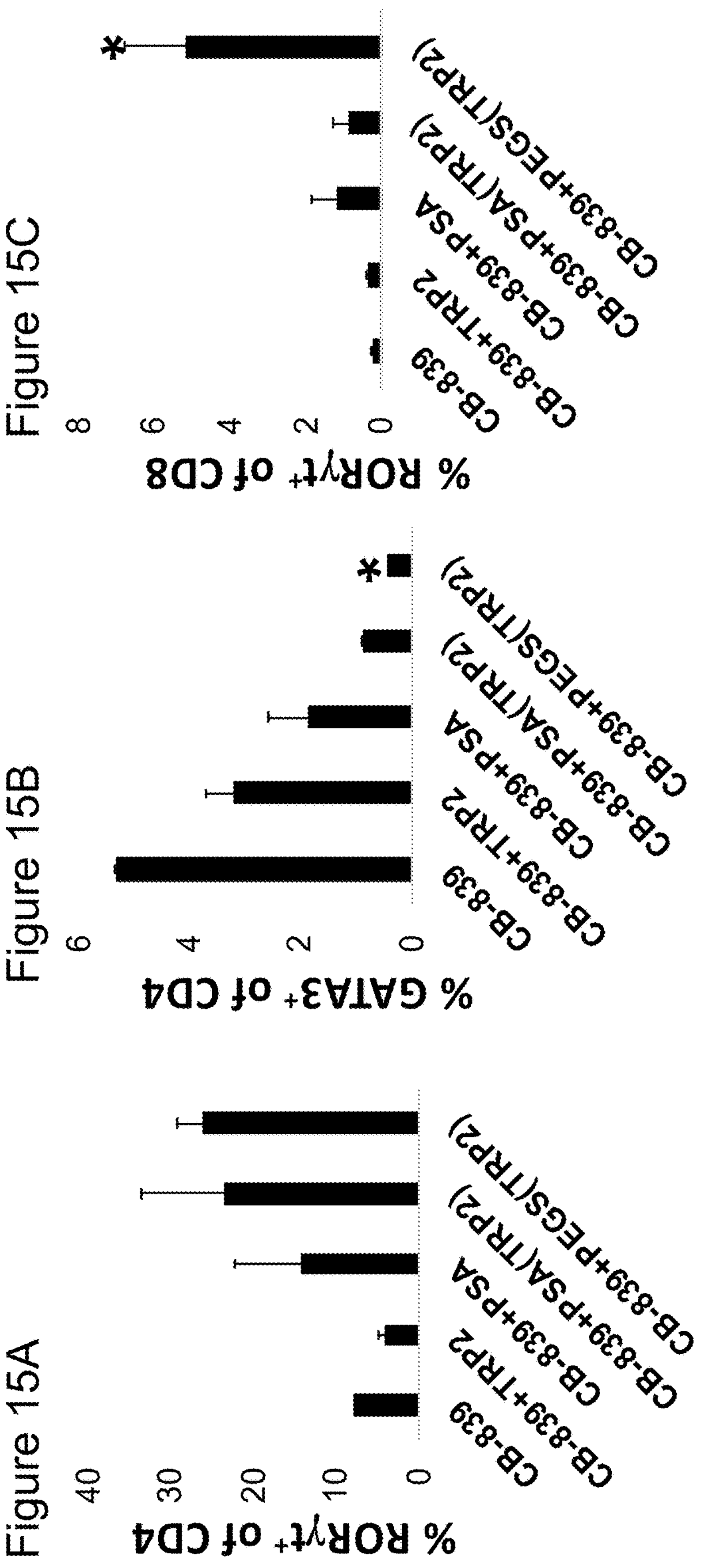
FIG. 15A through FIG. 15C, depicts representative results demonstrating that PEGS particles delivering TRP2 peptide induces increased levels of pro-inflammatory T cell responses in B16F10 tumors even in the presence of CB-839.

It was observed that the populations of Th1 and Tc1 cells in the draining lymph nodes was significantly higher than the non-draining lymph node in PSA(TRP2) and PEGS (TRP2) formulations, whereas Th1 and Tc1 populations for other conditions were similar to each other in draining and non-draining lymph nodes. In the tumor, it was observed that the (i) PEGS(TRP2) formulation induced 10-fold higher population of Tc17 cells as compared to all the other conditions; (ii) Treg population was not significantly different between the groups; (iii) Th1 and Tc1 population was 3-fold higher in PEGS(TRP2) group than PSA(TRP2), and these were higher than all the other conditions; (iv) Th2 population was significantly lower in PEGS(TRP2) group as compared to all the conditions; and (v) both PSA(TRP2) and PEGS(TRP2) had elevated Th17 cells as compared to all the other conditions. (FIG. 15A through FIG. 15C). Moreover, these treatments led to higher survival rate in PEGS(TRP2) cohort (35 days versus other groups last mice died at day 20). Lastly, the tumor burden was significantly decreased in PEGS(TRP2) group as compared to all the other conditions. Overall, these data demonstrated that faster and higher levels of succinate release from PEGS were instrumental in inducing higher frequency of pro-inflammatory T cells in the tumors, however, complete remission was not observed, which is a focus of present studies.

Figure 16C:
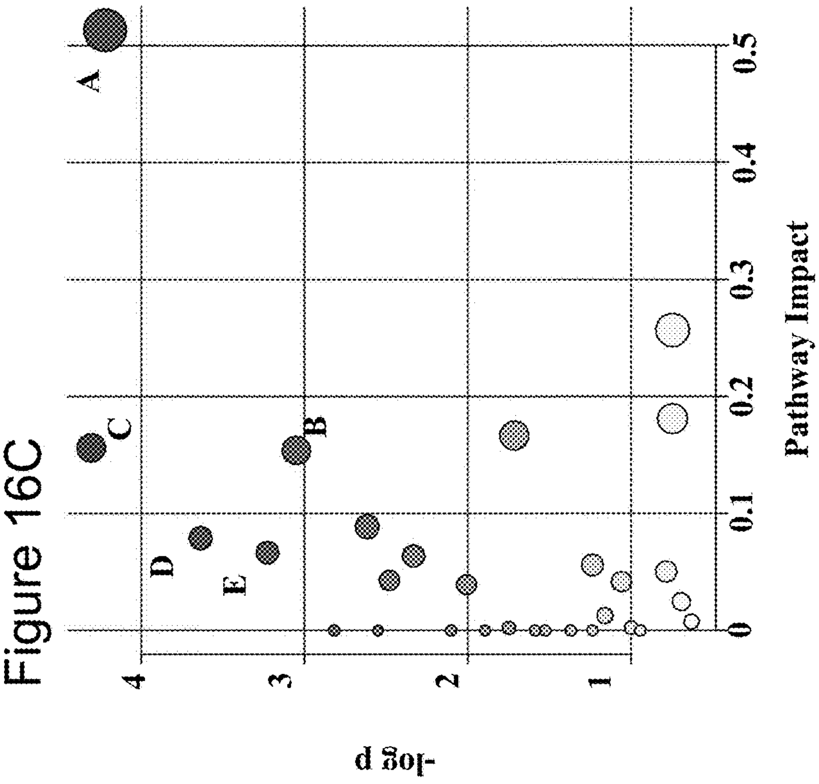
FIG. 16A through FIG. 16K, depicts representative results demonstrating the modulation of DC function by PEGS microparticles in vitro. Data shown as mean±SEM.
Figure 16B:
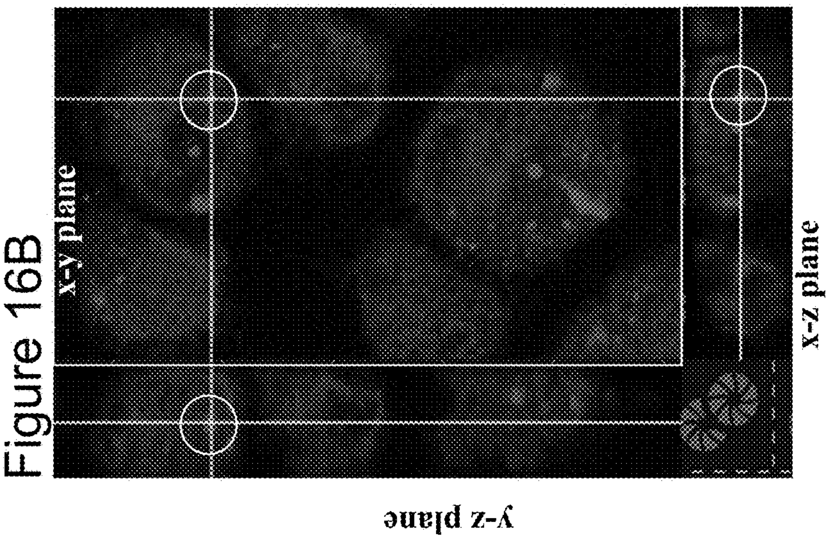
Figure 16A:
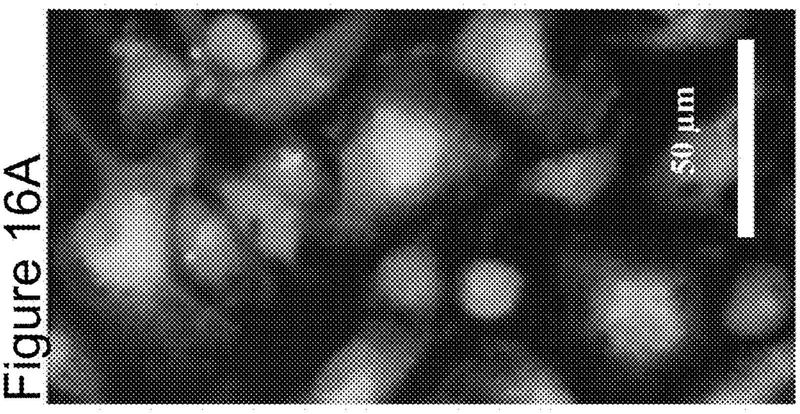
Figure 16E:
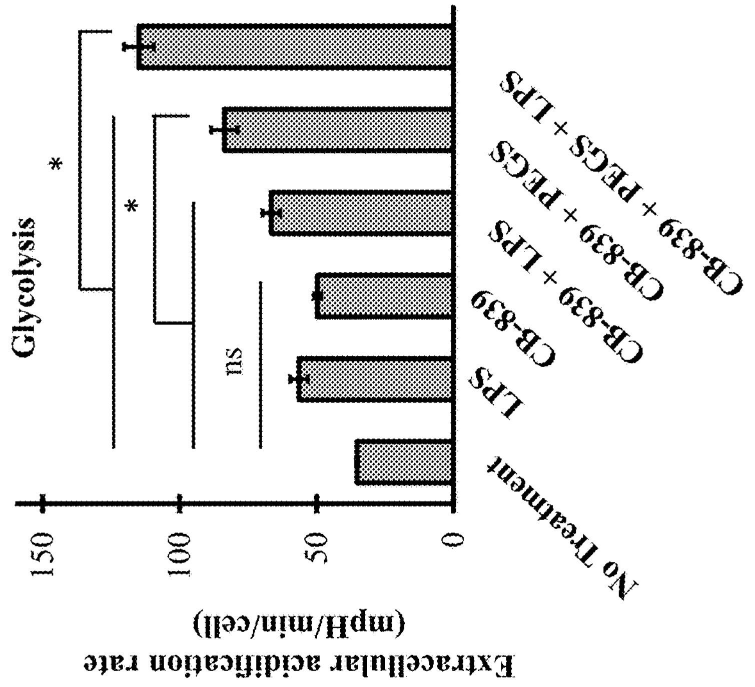
Figure 16D:
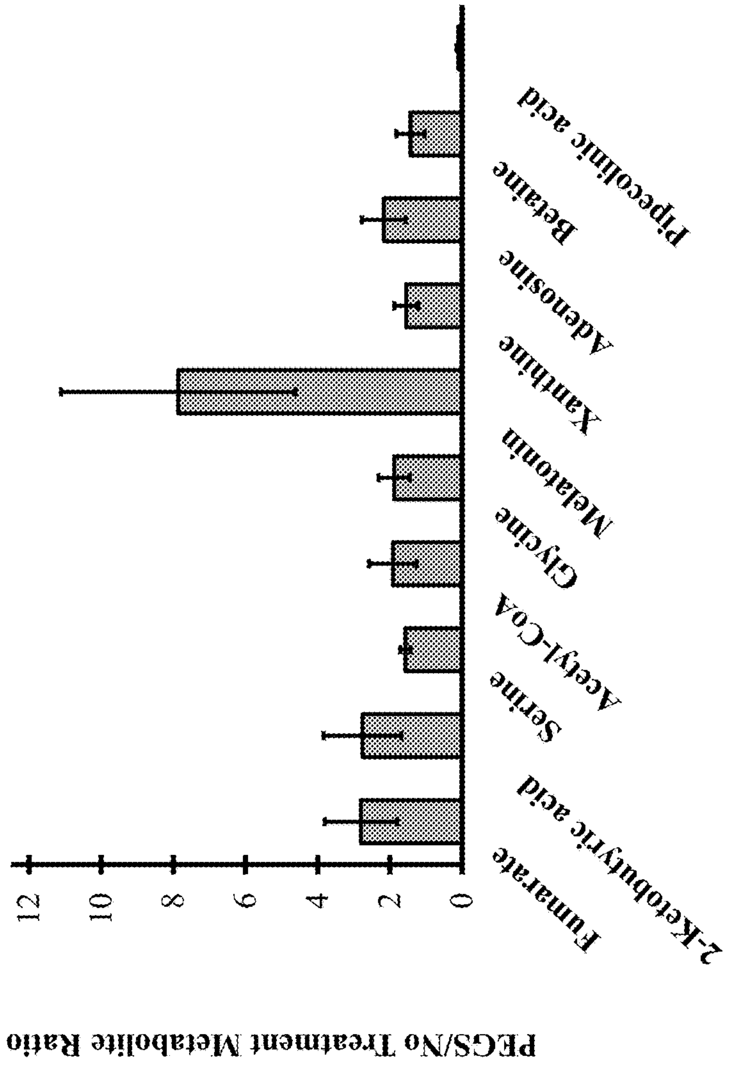
Figure 16G:
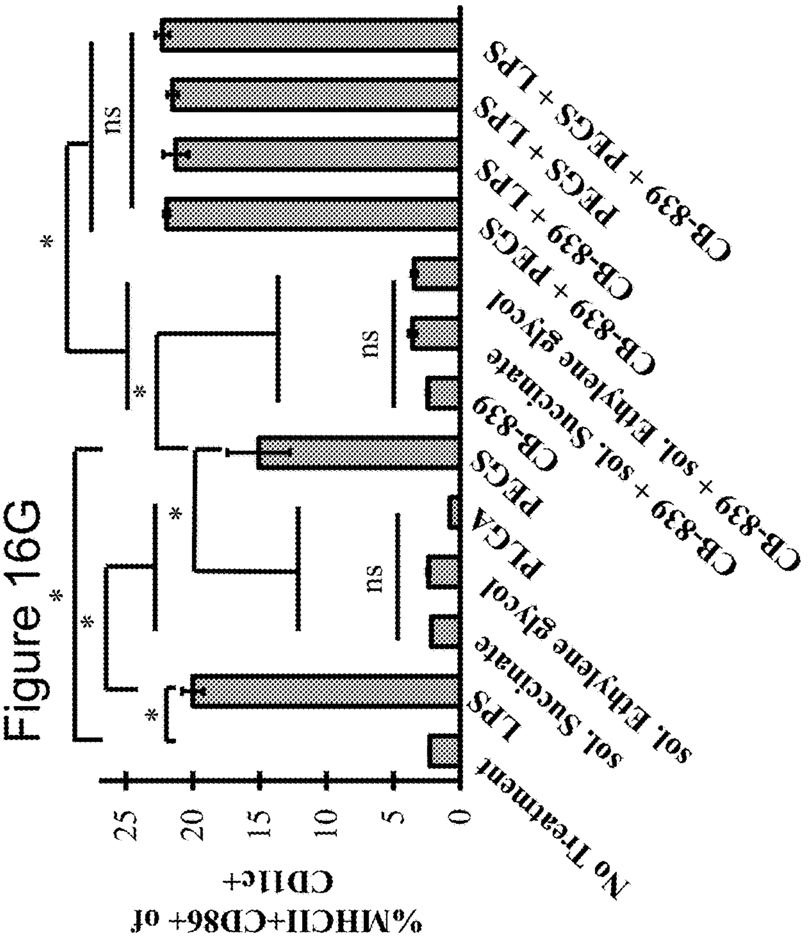
Figure 16F:
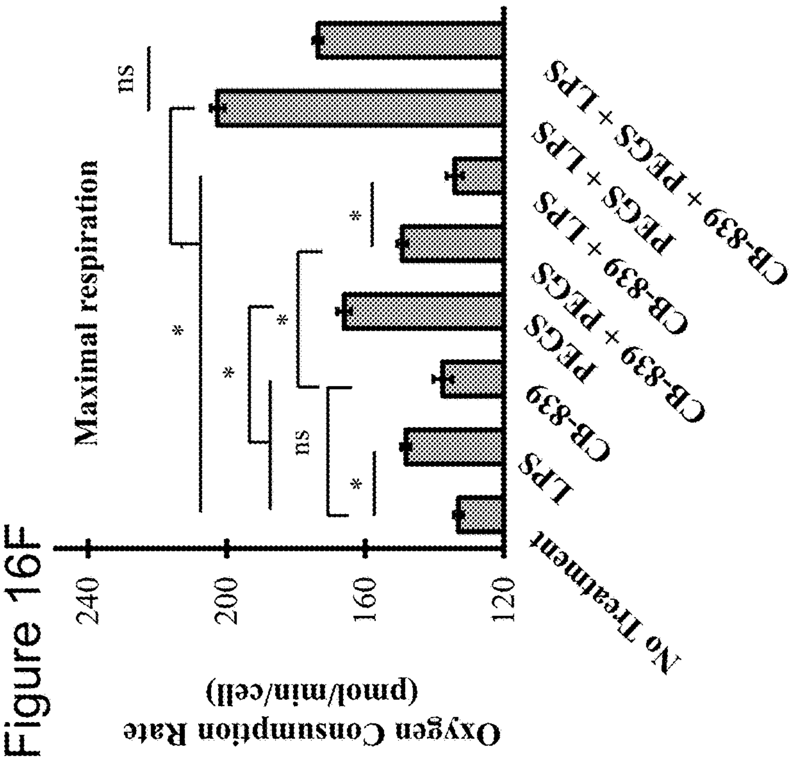
Figures 16H, 16I, 16J, 16K:
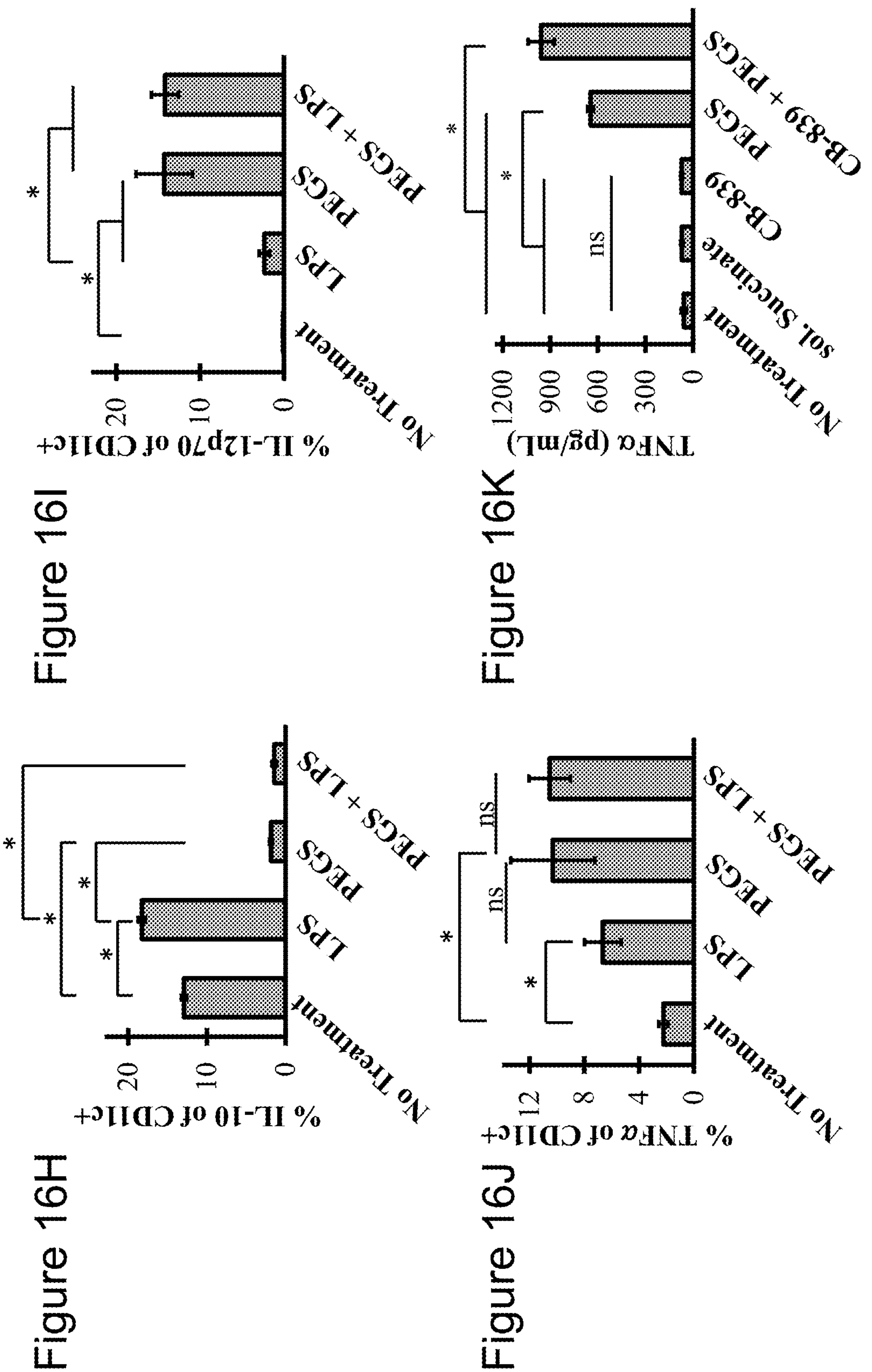

Furthermore, studies focused on the modulation of DC function by PEGS microparticles in vitro. Representative data demonstrated an effective modulation of DC pathways with PEGS microparticles and modulation of intracellular metabolites post treatment with PEGS microparticles (FIG. 16A through FIG. 16D). The data also demonstrated the effectiveness of the PEGS microparticles in the extracellular acidification rate and the maximal respiration of DCs upon treatment with PEGS microparticles (FIG. 16E and FIG. 16F). Further analyses using flow cytometry revealed the ability of the PEGS microparticles to modulate DC function (FIG. 16G) and various intracellular DC cytokinases, such as IL-10, IL-12p70, TNFa (FIG. 16H through FIG. 16J). The PEGS microparticles were also shown to effect the extracellular production of TNFa (FIG. 16G).

Figure 20:
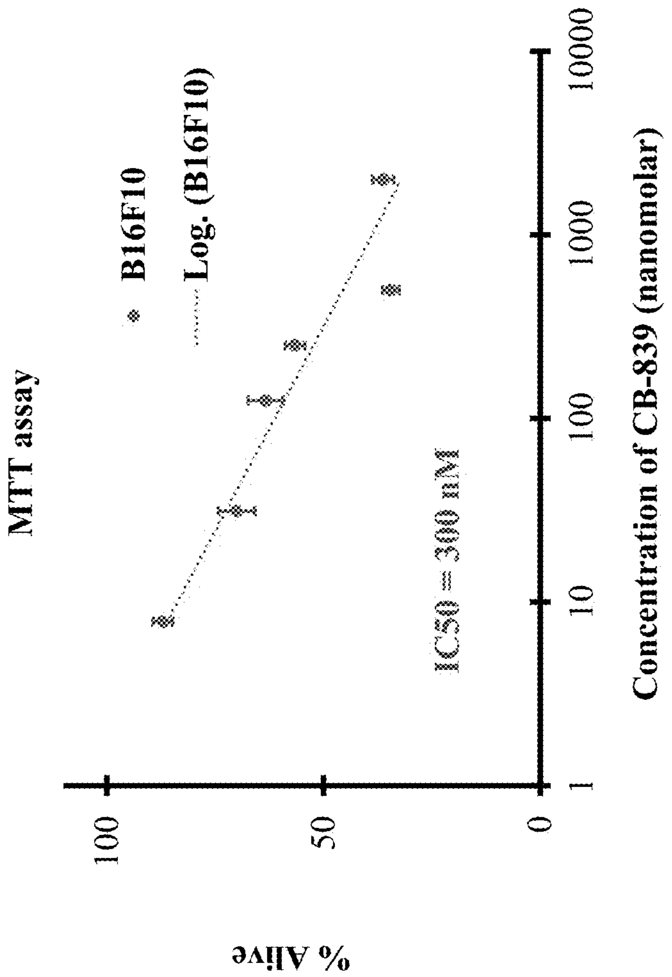
FIG. 20 depicts representative results demonstrating the data obtained using MTT assay indicating the IC50 of B16F10 melanoma cells using CB-839 (IC50=300 nM) (n=6).
Figure 21:
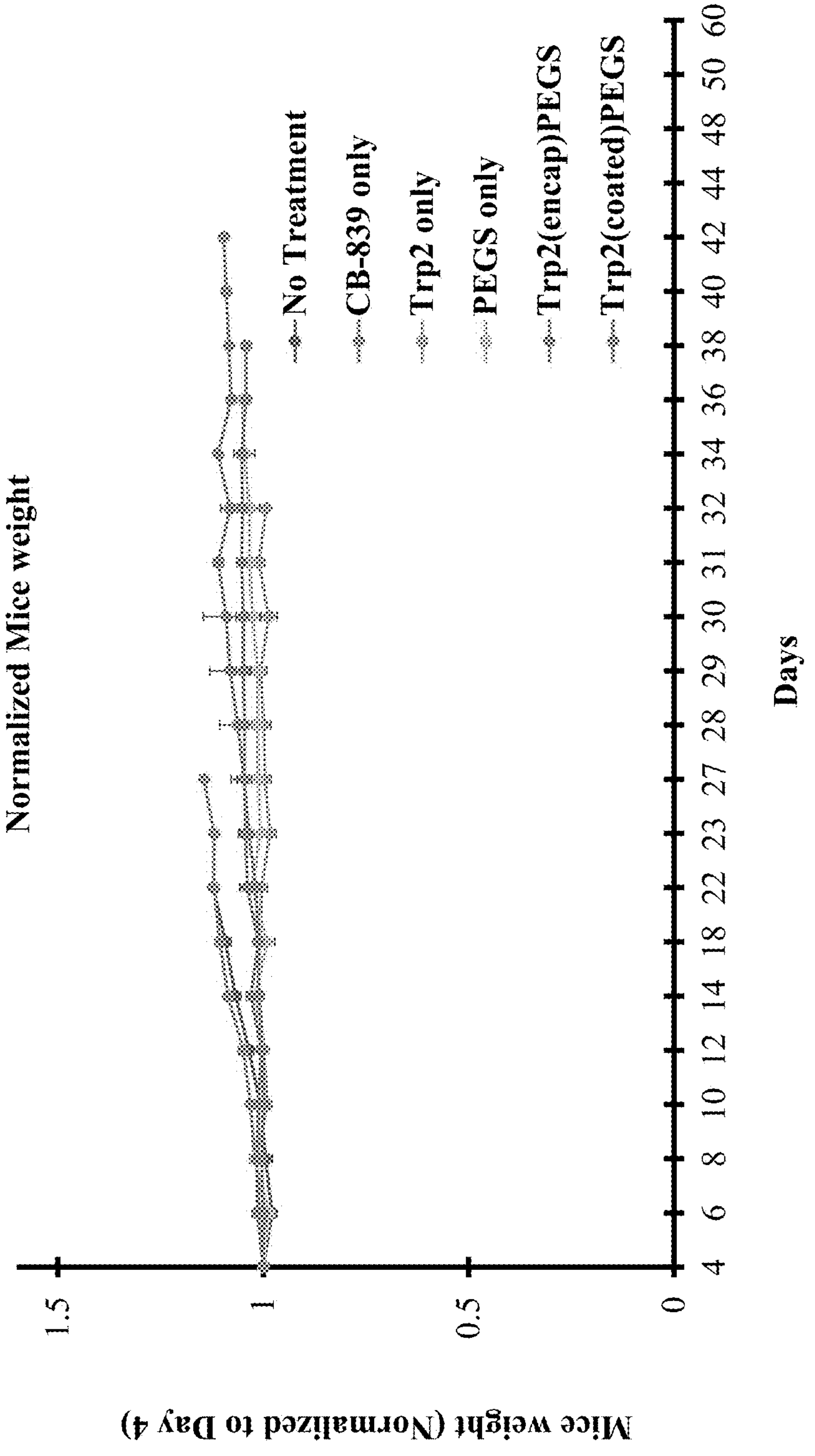
FIG. 21 depicts representative normalized tumor mice weights for all treatment groups (n=5). Data presented as mean±SEM.
Figure 22:
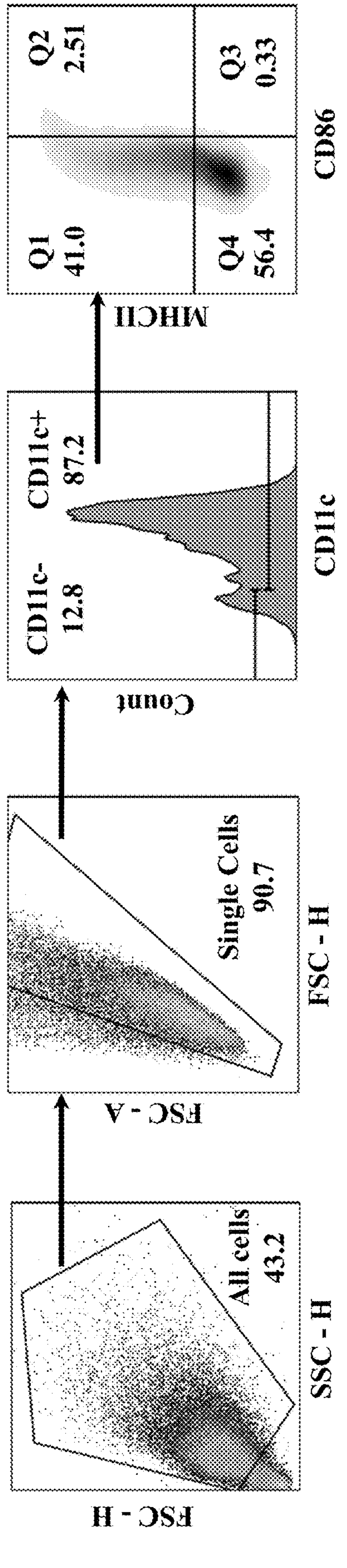
FIG. 22 depicts representative images of analyses of DCs using flow cytometry.
Figure 23:
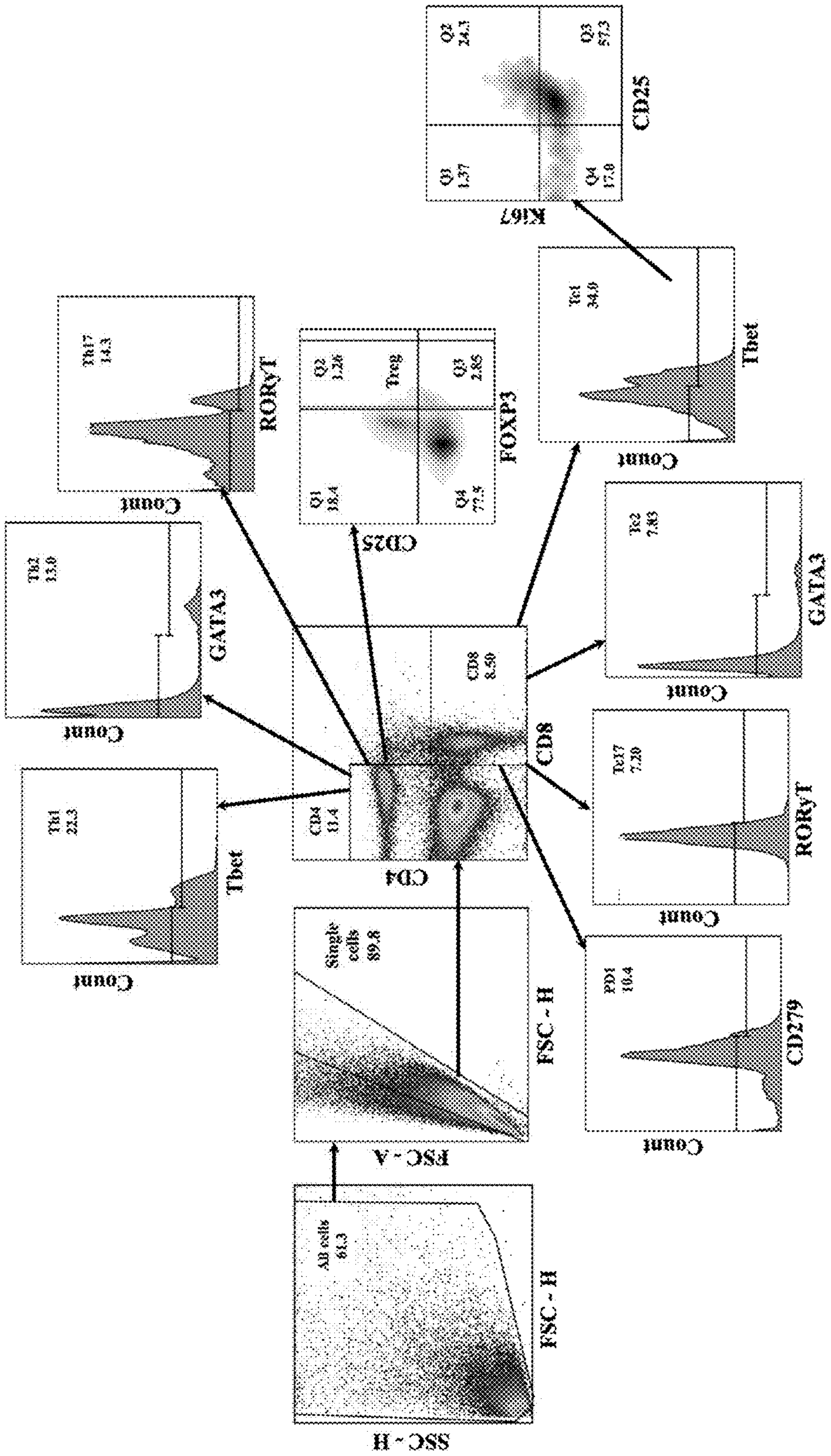
FIG. 23 depicts representative images of analyses of T cell using flow cytometry.

Accordingly, additional studies focused on delaying tumor growth in mice using Trp2 coated- and Trp2 encapsulated-PEGS microparticles (FIG. 18A through FIG. 18D and FIG. 21). Furthermore, succinate based microparticles were demonstrated to modulate DC and T cell function in vivo (FIG. 19A through FIG. 19D, FIG. 22, and FIG. 23). Additional data obtained using MTT assay indicated the IC50 of B16F10 in melanoma cells using CB-839 (FIG. 20).

In summary, the above disclosed data demonstrate various compositions and methods of use thereof to rescue immune cells (e.g., dendritic cells and T cells) from metabolic inhibition. The compositions comprise polymers of fructose 1,6, biphosphate, polyethyleneglycol-succinate with or without a TRP2 peptide or poly I:C. Through in vitro and in vivo experiments, the above disclosed data have shown that F16BP particles can rescue activation and glycolysis of dendritic cells in the presence of PFK15, a glycolysis pathway inhibitor. Similarly, PEGS particles can rescue activation, mitochondrial respiration, and glycolytic capacity of dendritic cells from effect of CB-839, a glutaminase1-mitochondrial respiration inhibitor. Administering the particles in a mouse model of melanoma in conjunction with metabolic inhibitors leads to increase in proinflammatory immune response, decrease in anti-inflammatory immune response and reduced tumor size. The compositions of the present invention can be used in conjunction with metabolic inhibitors for cancer therapy; and in a condition where increased metabolism of immune cells is desirable.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition comprising a particle, wherein the particle is a nanoparticle or microparticle; and wherein the particle comprises a compound having the structure of Formula (IV)

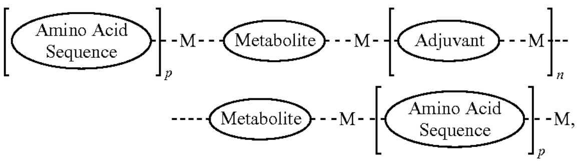

Formula (V)

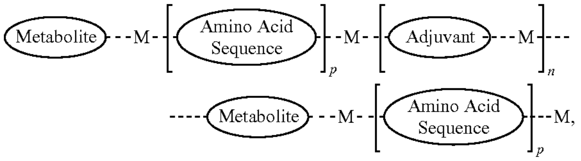

Formula (VI)

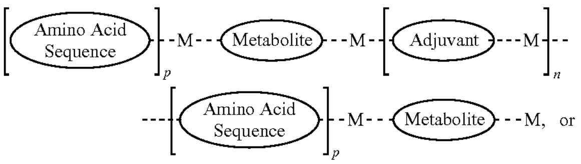

Formula (VII)

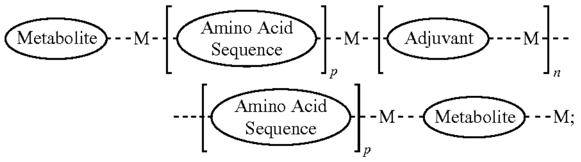

wherein each occurrence of M is independently selected from the group consisting of: Ca, Mg, Na, K, Sr, Zn, Fe, Co, and Cu;

each occurrence of n is independently an integer from 1 to 1000; and each occurrence of p is independently an integer represented by 0 or 1; and wherein a) each occurrence of metabolite independently comprises at least one selected from the group consisting of phosphoenolpyruvate, glucono-lactone-6-phosphate, gluconate-6-phosphase, sedoheptulose-7-phosphate, ribulose, ribulose-5-phosphate, xylulose, xylulose-5-phosphate, fructose-1,6-biphosphate, fructose-2,6-biphosphate, glycerate-2-phosphate, glucerate-3-phosphate, malate, fumarate, succinate, isocitrate, citrate, cis-aconitate, malonyl-CoA, acetyl COA, 3-methylbutyryl CoA, 2-methylbutyryl CoA, 3-ketoacyl CoA, 3-hydroxyacyl CoA, enoyl CoA, 3-ketoacyl functionalized metabolite, 3-hydroxyacyl functionalized metabolite, enoyl functionalized metabolite, fatty acids, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, and docosahexaenoic acid;

b) each occurrence of amino acid sequence independently comprises at least one selected from the group consisting of an isolated protein or fragment thereof, isolated peptide or fragment thereof, antigen or a fragment thereof, tyrosinase-related protein or fragment thereof, tyrosinase-related protein 1 (TRP1) or fragment thereof, tyrosinase-related protein 2 (TRP2) or fragment thereof, phosphorylated tyrosinase-related protein or fragment thereof, phosphorylated TRP1 or fragment thereof, and phosphorylated TRP2 or fragment thereof;

c) each occurrence of adjuvant independently comprises at least one selected from polyinosinic: polycytidylic acid (poly (I:C)) or analog thereof, muramyl dipeptide derivatives (MDP) or analog thereof, Alum and Emulsions, complete Freund's adjuvant (CFA), incomplete Freund's adjuvant (IFA), pattern recognition receptor (PRR) ligands, cyclic guanosine monophosphate-adenosine monophosphate (2'3'-cGAMP), bis-(3'-5') -cyclic dimeric adenosine monophosphate (c-di-AMP), Rp,Rp-isomer of the 2'3'-bisphosphorothioate analog of 3'3'-cyclic adenosine monophosphate (2'3'-c-di-AM (PS)2 (Rp,Rp)), cyclic diguanylate monophosphate-stimulator of interferon genes (c-di-GMP STING)-based vaccine adjuvant, CL401, CL413, CL429, Flagellin, Imiquimod, lipopolysaccharide (LPS) from the gram-negative bacteria E. coli 0111:B4 (LPS-EB), monophosphoryl lipid A from Salmonella minnesota R595 lipopolysaccharide (MPLA-SM), synthetic monophosphoryl lipid A (MPLA), oligodeoxynucleotides (ODN) 1585, ODN 1826, ODN 2006, ODN 2395, Pam3CSK4, Resiquimod (R848), and trehalose-6,6-dibehenate (TDB); or d) any combination of a) through c).

2. The composition of claim 1, wherein each occurrence of the amino acid sequence is independently selected from the group consisting of: an isolated protein or fragment thereof, isolated peptide or fragment thereof, antigen or a fragment thereof, tyrosinase-related protein or fragment thereof, tyrosinase-related protein 1 (TRP1) or fragment thereof, tyrosinase-related protein 2 (TRP2) or fragment thereof, phosphorylated tyrosinase-related protein or fragment thereof, phosphorylated TRP1 or fragment thereof, phosphorylated TRP2 or fragment thereof, and any combination thereof.

3. The composition of claim 1, wherein each occurrence of the metabolite is independently selected from the group consisting of:

phosphoenolpyruvate, glucono-lactone-6-phosphate, gluconate-6-phosphase, sedoheptulose -7-phosphate, ribulose, ribulose-5-phosphate, xylulose, xylulose-5-phosphate, fructose-1,6-biphosphate, fructose-2,6-biphosphate, glycerate-2-phosphate, glucerate-3-phosphate, malate, fumarate, succinate, isocitrate, citrate, cis-aconitate, malonyl-CoA, acetyl COA, 3-methylbutyryl CoA, 2-methylbutyryl CoA, 3-ketoacyl CoA, 3-hydroxyacyl CoA, enoyl CoA, 3-ketoacyl functionalized metabolite, 3-hydroxyacyl functionalized metabolite, enoyl functionalized metabolite, fatty acids, caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and any combination thereof.

4. The composition of claim 1, wherein each occurrence of the adjuvant is independently selected from the group consisting of polyinosinic: polycytidylic acid (poly (I:C)) or analog thereof, muramyl dipeptide derivatives (MDP) or analog thereof, Alum and Emulsions, complete Freund's adjuvant (CFA), incomplete Freund's adjuvant (IFA), pattern recognition receptor (PRR) ligands, cyclic guanosine monophosphate-adenosine monophosphate (2'3'-cGAMP), bis-(3'-5')-cyclic dimeric adenosine monophosphate (c-di-AMP), Rp,Rp-isomer of the 2'3'-bisphosphorothioate analog of 3'3'-cyclic adenosine monophosphate (2'3'-c-di-AM(PS) 2(Rp,Rp)), cyclic diguanylate monophosphate-stimulator of interferon genes (c-di-GMP STING)-based vaccine adjuvant, CL401, CL413, CL429, Flagellin, Imiquimod, lipopolysaccharide (LPS) from the gram-negative bacteria E. coli 0111:B4 (LPS-EB), monophosphoryl lipid A from Salmonella minnesota R595 lipopolysaccharide (MPLA-SM), synthetic monophosphoryl lipid A (MPLA), oligodeoxynucleotides (ODN) 1585, ODN 1826, ODN 2006, ODN 2395, Pam3CSK4, Resiquimod (R848), trehalose-6,6-dibehenate (TDB), and any combination thereof.

5. A composition comprising a particle, wherein the particle is a nanoparticle or microparticle; and wherein the particle comprises a compound having the structure of Formula (IV)

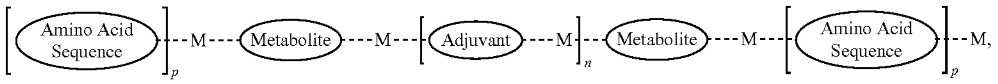

wherein the compound having the structure of Formula (IV) is a compound having the structure of Formula (VIII)

Formula (VIII)
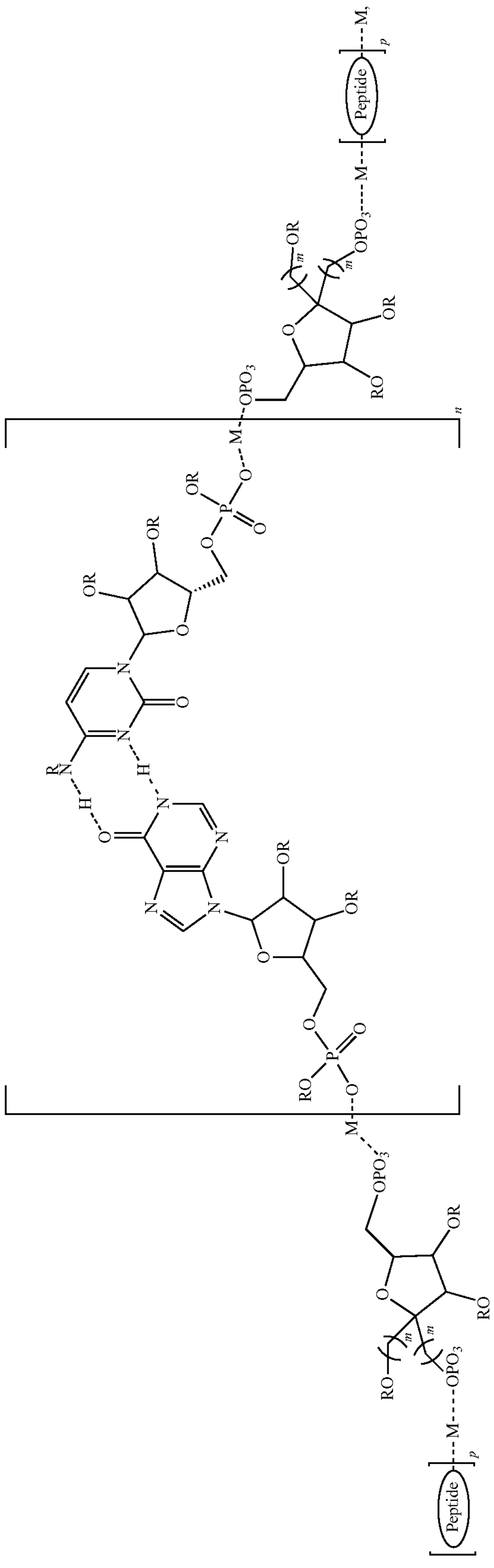

each occurrence of M is independently selected from the group consisting of: Ca, Mg, Na, K, Sr, Zn, Fe, Co, and Cu;

each occurrence of metabolite is independently a metabolite or derivative thereof;

each occurrence of R is independently selected from the group consisting of hydrogen, hydroxyl, carboxyl, alkyl, cycloalkyl, heterocycloalkyl, aryl, and heteroaryl;

each occurrence of m is independently an integer represented by 0 or 1;

each occurrence of n is independently an integer from 1 to 1000; and each occurrence of p is independently an integer represented by 0 or 1.

6. The composition of claim 1, further comprising a therapeutic agent.

7. A method of inducing an immune response in a subject, wherein the method comprises administering a therapeutically effective amount of the composition of claim 1 to the subject.

8. The method of claim 7, wherein method further comprises administering one or more metabolic inhibitors to the subject prior to, simultaneously, or after administering the therapeutically effective amount of the composition to the subject.

9. A method of preventing or treating a metabolic inhibition of at least one cell in a subject in need thereof, wherein the method comprises administering a therapeutically effective amount of the composition of claim 1 to the subject.

10. The method of claim 9, wherein method further comprises administering one or more metabolic inhibitors to the subject prior to, simultaneously, or after administering the therapeutically effective amount of the composition to the subject.

11. The method of claim 9, wherein the at least one cells is an immune cell.

12. The method of claim 9, wherein the composition induces at least one selected from the group consisting of: a glycolysis, tricarboxylic acid (TCA) cycle, pentose phosphate pathway (PPP), activation of the at least one cell, extracellular acidification rate (ECAR), oxygen consumption rate (OCR), mitochondrial respiration, release of a metabolite, pro-inflammatory response, BRAF inhibitors, and cancer cell suppression.

13. The method of claim 9, wherein the composition:

a) decreases the level of at least one immune suppressive cell;

b) increases the level of at least one selected from the group consisting of: a T cell, type 1 CD8+ T cell (Tc1), type 2 CD8+ T cell (Tc2), IL-17-producing CD8+ T cell (Tc17), T helper cell (Th), Th1, Th17, and effector T cell (Teff); or c) both a) and b).

14. The method of claim 9, wherein the composition:

a) reduces a cancer cell proliferation;

b) reduces or inhibits a tumor growth;

c) stops a tumor growth;

d) stops at least one cancer cell from metastasizing; or any combination thereof.

* * * * *